US012728181B2

(12) United States Patent
Daristotle et al.

(10) Patent No.: US 12,728,181 B2
(45) Date of Patent: Sep. 8, 2026

(54) SOLUTION BLOW SPUN POLYMER CONSTRUCTS, COMPOSITIONS AND METHODS OF FABRICATIONS AND USES RELATING THERETO

(71) Applicants:, College Park, MD (US); Children's National Medical Center, Washington, DC (US)

(72) Inventors: John Daristotle, Bel Air, MD (US); Shadden Zaki, Bethesda, MD (US); Peter Kofinas, North Bethesda, MD (US); Anthony Sandler, Bethesda, MD (US); Lung Lau, Washingtron, DC (US); Leopoldo Torres, Greenbelt, MD (US)

(73) Assignees: University of Maryland, College Park, College Park, MD (US); Children's National Medical Center, Washington, DC (US)

( * ) Notice: Subject to any disclaimer, the term of this patent is extended or adjusted under 35 U.S.C. 154(b) by 924 days.

(21) Appl. No.: 17/437,280

(22) PCT Filed: Mar. 10, 2020

(86) PCT No.: PCT/US2020/021879
§ 371 (c)(1),
(2) Date: Sep. 8, 2021

(87) PCT Pub. No.: WO2020/185771
PCT Pub. Date: Sep. 17, 2020

(65) Prior Publication Data

US 2022/0160929 A1 May 26, 2022

Related U.S. Application Data

(60) Provisional application No. 62/816,568, filed on Mar. 11, 2019.

(51) Int. Cl.
*A61L 24/00* (2006.01)
*A61L 24/04* (2006.01)
*A61L 26/00* (2006.01)

(52) U.S. Cl.
CPC ....... *A61L 24/0015* (2013.01); *A61L 24/0073* (2013.01); *A61L 24/046* (2013.01);
(Continued)

(58) Field of Classification Search
CPC ............. A61L 24/0015; A61L 24/0073; A61L 24/046; A61L 26/0019; A61L 26/0066; A61L 26/0076; A61L 24/0089
See application file for complete search history.

(56) References Cited

U.S. PATENT DOCUMENTS

2003/0069369 A1* 4/2003 Belenkaya ........... D01D 5/0038 525/437
2016/0325010 A1* 11/2016 Liebler ................... A61L 24/08

OTHER PUBLICATIONS

Behrens et al. "Biodegradable Polymer Blend Based Surgical Sealant with Body Temperature Mediated Adhesion" Adv. Mater. Dec. 2015 2022; 27 (48): 8056-8061 (Year: 2015).*

(Continued)

*Primary Examiner* — Andrew J. Oyer
(74) *Attorney, Agent, or Firm* — HYLTON-RODIC LAW PLLC

(57) ABSTRACT

The present disclosure relates to a biocompatible composition comprising a solution of low molecular weight polymer and high molecular weight polymer. The present disclosure also relates to biocompatible compositions comprising poly (lactic-co-glycolic acid) (PLGA) and poly(ethylene glycol) (PEG), and additionally including a suspension of silica particles and/or a therapeutic agent. The present disclosure is also directed to biocompatible polymer fiber constructs formed from the disclosed compositions, methods of fabri-
(Continued)

cation thereof, and uses of such constructs and compositions.

14 Claims, 43 Drawing Sheets

(52) U.S. Cl.
CPC ....... *A61L 26/0019* (2013.01); *A61L 26/0066* (2013.01); *A61L 26/0076* (2013.01)

(56) References Cited

OTHER PUBLICATIONS

Ahn, B. K. (2017) "Perspectives on Mussel-Inspired Wet Adhesion," J. Am. Chem. Soc. 139(30):10166-10171.
Alleyne, C. H. et al. (1998) "Efficacy and Biocompatibility of a Photopolymerized, Synthetic, Absorbable Hydrogel as a Dural Sealant in a Canine Craniotomy Model," J. Neurosurg. 88(2):308-313.
Annabi, N. et al. (2014) "Surgical materials: Current challenges and nano-enabled solutions," Nano Today 9:574-589.
Annabi, N. et al. (2015) "Elastic sealants for surgical applications," European Journal of Pharmaceutics and Biopharmaceutics, 95:27-39.
Annabi, N. et al. (2017) "Engineering a Highly Elastic Human Protein-Based Sealant for Surgical Applications," Sci. Transl. Med. 9(410):eaai7466.
Annabi, N. et al. (2017) "Engineering a sprayable and elastic hydrogel adhesive with antimicrobial properties for wound healing," Biomaterials 139:229-243.
Argon, A.S. et al. (2003) "Toughenability of polymers," Polymer 44:6013-6032.
Artzi, N. et al. (2009) "Characterization of Star Adhesive Sealants Based On PEG/Dextran Hydrogels," Macromol. Biosci. 9(8):754-765.
Artzi, N. et al. (2011) "Tuning adhesion failure strength for tissue-specific applications," Acta Biomater 7:67-74.
Arung, W. et al. (2011) "Pathophysiology and Prevention of Postoperative Peritoneal Adhesions," World J. Gastroenterol. WJG 17(41):4545-4553.
Assmann, A. et al. (2017) "A highly adhesive and naturally derived sealant," Biomaterials 140:115-127.
Auxenfans C. et al. (2015) "Cultured autologous keratinocytes in the treatment of large and deep burns: A retrospective study over 15 years," Burns 41:71-9.
Ayala-Nunez, N. et al. (2009) "Silver Nanoparticles Toxicity and Bactericidal Effect against MEthicillin Resistant *Staphylococcus aureus*: Nanoscale Does Matter," Nanobiotechnology 5:2-9.
Bachler, G. et al. (2013) "A physiologically based pharmacokinetic model for ionic silver and silver nanoparticles," Int J Nanomedicine 8(1):3365-3382.
Baït, N. et al. (2011) "Hydrogel nanocomposites as pressure-sensitive adhesives for skin-contact applications," Soft Matter 7:2025-2032.
Balouiri M. et al. (2016) "Methods for in vitro evaluating antimicrobial activity: A review," J Pharm Anal 6:71-9.
Barnett A. et al. (1983) "Comparison of Synthetic Adhesive Moisture Vapor Permeable And Fine Mesh Gauze Dressings for Split-Thickness Skin Graft Donor Sites," Am J Surg 145(3):379-381.
Barrett, D.G. et al. (2013) "Mechanically robust, negatives welling, mussel-inspired tissue adhesives," Adv. Healthc. Mater. 2:745-755.
Behrens, A. M. et al. (2016) "Rapid Fabrication of Poly(DL-Lactide) Nanofiber Scaffolds with Tunable Degradation for Tissue Engineering Applications by Air-Brushing," Biomed. Mater. 11(3):035001.
Behrens, A.M. et al. (2014) "Blood-aggregating hydrogel particles for use as a hemostatic agent," Acta Biomater 10(2):701-708.
Behrens, A.M. et al. (2014) "Hemostatic strategies for traumatic and surgical bleeding: Hemostatic Strategies for Traumatic and Surgical Bleeding," Journal of Biomedical Materials Research Part A, 102:4182-4194.
Behrens, A.M. et al. (2014) "In Situ Deposition of PLGA Nanofibers via Solution Blow Spinning," ACS Macro Lett 3(3):249-254.
Behrens, A.M. et al. (2015) "Biodegradable-polymer-blend-based surgical sealant with body-temperature-mediated adhesion," Adv. Mater. 27:8056-8061.
Berman B. et al. (2017) "Keloids and Hypertrophic Scars: Pathophysiology, Classification, and Treatment," Dermatol Surg 43 Suppl 1:S3-S18.
Borde, A. et al. (2012) "Increased Water Transport in PDMS Silicone Films by Addition of Excipients," Acta Biomater. 8(2):579-588.
Bouten, P.J.M. et al.(2014) "The chemistry of tissue adhesive materials," Progress in Polymer Science 39:1375-1405.
Bruggmann, D. et al. (2010) "Intra-Abdominal Adhesions," Dtsch. Ärztebl. Int. 107(44):769-775.
Bu, Y. et al. (2019) "Tetra-PEG Based Hydrogel Sealants for In vivo Visceral Hemostasis," Adv. Mater. 31(28):1901580.
Caetano G.F. et al. (2016) "Comparison of collagen content in skin wounds evaluated by biochemical assay and by computer-aided histomorphometric analysis," Pharm Biol 54:2555-9.
Calcaterra, J. et al. (2013) "Recombinant human fibrinogen that produces thick fibrin fibers with increased wound adhesion and clot density," Biomacromolecules 14:169-178.
Canesso M.C. et al. (2014) "Skin wound healing is accelerated and scarless in the absence of commensal microbiota," J Immunol 193:5171-80.
Carlson, M.A. et al. (2014) "A totally recombinant human fibrin sealant," J. Surg. Res. 187:334-342.
Cassidy C. et al. (2005) "Biobrane versus duoderm for the treatment of intermediate thickness burns in children: A prospective, randomized trial," Burns 31:890-3.
Cencer, M. et al. (2014) "Effect of PH on the Rate of Curing and Bioadhesive Properties of Dopamine Functionalized Poly(Ethylene Glycol) Hydrogels," Biomacromolecules 15(8):2861-2869.
Chan, L.W. et al. (2015) "A synthetic fibrin cross-linking polymer for modulating clot properties and inducing hemostasis," Sci. Transl. Med. 7:277ra29.
Chereddy K.K. et al. (2018) "PLGA: from a classic drug carrier to a novel therapeutic activity contributor," J Control Release 289:10-13.
Cheshire P.A. et al. (2016) "Artificial dermal templates: A comparative study of NovoSorb™ Biodegradable Temporising Matrix (BTM) and Integra® Dermal Regeneration Template (DRT)," Burns 42:1088-96.
Chittmittrapap, S. et al. (1992) "Anastomotic leakage following surgery for esophageal atresia," Journal of Pediatric Surgery, 27:29-32.
Church D. et al. (2006) "Burn wound infections," Clin Microbiol Rev 19:403-34.
Creton, C. et al. (2009) "Large-Strain Mechanical Behavior of Model Block Copolymer Adhesives," Macromolecules 42(20):7605-7615.
Cross S.E. and Roberts M.S. (1999) "Defining a model to predict the distribution of topically applied growth factors and other solutes in excisional full-thickness wounds," J Invest Dermatol 112(1)36-41.
Czech, Z. et al. (2013) "Biodegradable Self-Adhesive Tapes with Starch Carrier," Int. J. Adhes. Adhes. 44:195-199.
Damour O. et al. (1992) "Cytotoxicity evaluation of antiseptics and antibiotics on cultured human fibroblasts and keratinocytes," Burns 18(6):479-85.
Daristotle, J. L. et al. (2016) "A Review of the Fundamental Principles and Applications of Solution Blow Spinning," ACS Appl. Mater. Interfaces 8(51):34951-34963.
Davies, P. et al. (2008) "Evidence Review: The Clinical Benefits of Safetac Technology in Wound Care," J. Wound Care Suppl, 3-31.
Deng, W. et al. (2016) "Absorptive Supramolecular Elastomer Wound Dressing Based on Polydimethylsiloxane-(Polyethylene Glycol)-Polydimethylsiloxane Copolymer: Preparation and Characterization," RSC Adv. 6(57):51694-51702.

(56) References Cited

OTHER PUBLICATIONS

Deng, X. (2018) "Progress on Rubber-Based Pressure-Sensitive Adhesives," J. Adhes. 94(2):77-96.
Doloff, J.C. et al. (2017) "Colony stimulating factor-1 receptor is a central component of the foreign body response to biomaterial implants in rodents and non-human primates," Nature Materials 16(6):671-680.
Schäfer, K. et al. (1989) "Disorders of microcirculation in colon anastomoses and their significance for the pathogenesis of suture dehisence," Langenbecks Arch Chir. 375: 24-32.
Vakalopoulos, K.A. et al. (2015). "Mechnical strength and rheological properties of tissue adhesives with regard to colorectal anastomosis: an ex vivo study," Ann. Surg. 261: 323-331.
Mizrahi, B. et al. (2011) "Elasticity and safety of alkoxyethyl cyanoacrylate tissue adhesives," Acta Biomaterialia 7:3150-3157.
Morones-Ramirez J.R. et al. (2013) "Silver enhances antibiotic activity against gram-negative bacteria," Sci Transl Med 5:190ra81.
Mottas, I. et al. (2019) "Amphiphilic nanoparticle delivery enhances the anticancer efficacy of a TLR7 ligand via local immune activation," Biomaterials 190-191, 111-120.
Nasiri, M. et al. (2018) "Enhanced Mechanical and Adhesion Properties in Sustainable Triblock Copolymers via Non-Covalent Interactions," Macromolecules 51(7):2456-2465.
Nunez Lopez O. et al. (2017) "Predicting and managing sepsis in burn patients: current perspectives," Ther Clin Risk Manag 13:1107-17.
Okada, M. et al. (2017) "Biocompatible nanostructured solid adhesives for biological soft tissues," Acta Biomater. 57:404-413.
Oliveira J.E. et al. (2011) "Nano and submicrometric fibers of poly(D,L-lactide) obtained by solution blow spinning: Process and solution variables," J Applied Polym Sci 122:3396-405.
O'Shaughnessy K.D. et al. (2009) "Homeostasis of the epidermal barrier layer: a theory of how occlusion reduces hypertrophic scarring," Wound Repair Regen. 17(5):700-708.
Ostomel, T.A. et al. (2007) "Metal Oxide Surface Charge Mediated Hemostasis," Langmuir 23:11233-11238.
Pandey, N. et al. (2017) "Biodegradable nanoparticles enhanced adhesiveness of mussel-like hydrogels at tissue interface," Adv. Healthc. Mater. 7(7):e1701069.
Percival, S.L. et al. (2005) "Bacterial resistance to silver in wound care," J Hosp Infect 60:1-7.
Porporato, P.E. et al. (2012) "Lactate stimulates angiogenesis and accelerates the healing of superficial and ischemic wounds in mice," Angiogenesis 15(4):581-592.
Pourshahrestani, S. et al. (2019) "Well-ordered mesoporous silica and bioactive glasses: promise for improved hemostasis," Biomater. Sci. 7:31-50.
Pukki, T. et al. (2010) "Assessing Mepilex® Border in Post-Operative Wound Care," Wounds UK 6(1):30-40.
Rai M. et al. (2009) "Silver nanoparticles as a new generation of antimicrobials," Biotechnol Adv 27:76-83.
Reish R.G. et al. (2009) "Modulation of scarring in a liquid environment in the Yorkshire pig," Wound Repair Regen 17:806-16.
Rhee, C. et al., (2017) "CDC Prevention Epicenter Program, Incidence and Trends of Sepsis in US Hospitals Using Clinical vs Claims Data," JAMA 318(13):1241-1249.
Richardson T.P. et al. (2001) "Polymeric system for dual growth factor delivery," Nat Biotechnol. 19(11):1029-1034.
Rippon, M. et al. (2007) "Skin Adhesives and Their Role in Wound Dressings," Wounds UK 3(4):76-86.
Rittigstein, P. and Torkelson, J.M. (2006) "Polymer-nanoparticle interfacial interactions in polymer nanocomposites: Confinement effects on glass transition temperature and suppression of physical aging," Journal of Polymer Science Part B: Polymer Physics, 44:2935-2943.
Röhrig, M. et al. (2012) "3D Direct Laser Writing of Nano- and Microstructured Hierarchical Gecko-Mimicking Surfaces," Small 8:3009-3015.
Rose, S. et al. (2013) "Nanoparticle solutions as adhesives for gels and biological tissues," Nature 505:382-385.
Sahu, D. et al. (2016) "In vitro Cytotoxicity of Nanoparticles: A Comparison between Particle Size and Cell Type," Journal of Nanoscience, vol. 2016, ID 4023852.
Saini, P. et al. (2016) "Poly(Lactic Acid) Blends in Biomedical Applications," Adv. Drug Deliv. Rev. 107:47-59.
Samudrala, S. (2008) "Topical Hemostatic Agents in Surgery: A Surgeon's Perspective," AORN J. 88(3):S2-S11.
Ensari, C.O. et al. (2010) "Effects of N-butyl-2-cyanoacrylate on high-level jejunojejunostomy," Eur Surg Res, 44 (2010) 13-16.
Schwarze H. et al. (2007) "Suprathel, a new skin substitute, in the management of donor sites of split-thickness skin grafts: results of a clinical study," Burns 33:850-4.
Scola, M.R. et al. (2012) "A review of current methods for assessing hemostasis in vivo and introduction to a potential alternative approach," Thromb Res 129:S57-S61.
Shin, J. et al. (2011) "Pressure-Sensitive Adhesives from Renewable Triblock Copolymers," Macromolecules 44(1):87-94.
Silecchia, G. et al. (2008) "The use of fibrin sealant to prevent major complications following laparoscopic gastric bypass: results of a multicenter, randomized trial," Surgical Endoscopy, 22:2492-2497.
Sood, A. et al. (2014) "Wound Dressings and Comparative Effectiveness Data," Adv. Wound Care 3(8):511-529.
Sorrell J.M. and Caplan A.I. (2004) "Fibroblast heterogeneity: more than skin deep," J Cell Sci 117:667-75.
Spotnitz, W. D. (2001) "Commercial Fibrin Sealants in Surgical Care," Am. J. Surg. 182(2, Supp 1):S8-S14.
Spotnitz, W.D. et al., (2008) "Hemostats, sealants, and adhesives: components of the surgical toolbox," Transfusion, 48:1502-1516.
Srinivasan S. et al,. (2011) "Solution spraying of poly(methyl methacrylate) blends to fabricate microtextured, superoleophobic surfaces," Polymer 52:3209-18.
Stöber, W. et al. (1968) "Controlled growth of monodisperse silica spheres in the micron size range," Journal of Colloid and Interface Science, 26:62-69.
Strehin, I. et al. (2010) "A Versatile PH Sensitive Chondroitin Sulfate-PEG Tissue Adhesive and Hydrogel," Biomaterials 31(10):2788-2797.
Sun G. et al. (2011) "Dextran hydrogel scaffolds enhance angiogenic responses and promote complete skin regeneration during burn wound healing," Proc Natl Acad Sci U S A 108:20976-81.
Sun S. et al. (2017) "Lactic acid: no longer an inert and end product of glycolysis," Phys Ther 32(6):453-463.
Feldman, D. L. Et al. (1991) "A prospective trial comparing Biobrane, Duoderm and xeroform for skin graft donor sites," Surgery, Gynecology & Obstetrics 173: 1-5.
Toussaint J. et al. (2015) "Topical antibiotic ointment versus silver-containing foam dressing for second-degree burns in swine," Acad Emerg Med 22(8):927-33.
Tribble D.R. et al. (2018) "Epidemiology of Trauma-Related Infections among a Combat Casualty Cohort after Initial Hospitalization: The Trauma Infectious Disease Outcomes Study," Surg Infect (Larchmt) 19:494-503.
Trott A., Wound Dressing and Bandaging Techniques, Wounds and Lacerations: Emergency Care and Closure, Philadelphia, PA: Elsevier; 2012:266-81.
Uhlig C. et al. (2007) "Suprathel®—An innovative, resorbable skin substitute for the treatment of burn victims," Burns 33:221-9.
Widman, T. J. et al. (2008) "Allergic Contact Dermatitis from Medical Adhesive Bandages in Patients Who Report Having a Reaction to Medical Bandages," Dermatitis 19(1): 1-10.
Van der Ham, A.C. et al., (1991) "Effect of fibrin sealant on the healing colonic anastomosis in the rat," Br J Surg, 78:49-53.
Vendamme, R. et al. (2014) "Recent Synthetic Approaches and Emerging Bio-Inspired Strategies for the Development of Sustainable Pressure-Sensitive Adhesives Derived from Renewable Building Blocks," J. Appl. Polym. Sci. 131(17.
Vloemans A.F. et al. (2014) "Optimal treatment of partial thickness burns in children: a systematic review," Burns 40:177-90.
Vuocolo, T. et al. (2012) "A Highly elastic and adhesive gelatin tissue sealant for gastrointestinal surgery and colon anastomosis," J. Gastrointest. Surg. 16:744-752.

(56) References Cited

OTHER PUBLICATIONS

Vural, M. et al. (2018) "Spray-Processed Composites with High Conductivity and Elasticity," ACS Appl. Mater. Interfaces, 10(16):13953-13962.
Falsafi, A. et al. (2000) "Compositional Effects on the Adhesion of Acrylic Pressure Sensitive Adhesives," Langmuir 16 (4):1816-1824.
Teepe, R.G. et al. (1993) "Cytotoxic effects of topical antimicrobial and antiseptic agents on human keratinocytes in vitro," J Trauma 35(1): 8-19.
Fu, C. et al. (2013) "The absorption, distribution, excretion and toxicity of mesoporous silica nanoparticles in mice following different exposure routes," Biomaterials 34:2565-2575.
Galandakova A. et al. (2016) "Effects of silver nanoparticles on human dermal fibroblasts and epidermal keratinocytes," Hum Exp Toxicol 35:946-57.
Geim, A.K. et al. (2003) "Microfabricated adhesive mimicking gecko foot-hair," Nat Mater 2:461-463.
Greenwood J.E. et al. (2009) "Experience With Biobrane: Uses and Caveats for Success," Eplasty 9:e25.
Greiner, C. et al. (2009) "Hierarchical Gecko-Like Adhesives," Adv. Mater 21:479-482.
Gurtner G.C. et al. (2008) "Wound repair and regeneration," Nature 453:314-321.
Hammond, J. et al. (2014) "The Burden of Gastrointestinal Anastomotic Leaks: an Evaluation of Clinical and Economic Outcomes," Journal of Gastrointestinal Surgery, 18:1176-1185.
Heher, P. et al. (2018) "An Overview of Surgical Sealant Devices: Current Approaches and Future Trends," Expert Rev. Med. Devices 15(10):747-755.
Henise, J. et al. (2016) "Surgical sealants with tunable swelling, burst pressures, and biodegradation rates," J. Biomed. Mater. Res. B Appl. Biomater. 105:1602-1611.
Hidalgo E. et al. (1998) "Silver nitrate: antimicrobial activity related to cytotoxicity in cultured human fibroblasts," Skin Pharmacol Appl Skin Physiol 11(3):140-51.
Hotaling, N.A. et al. (2015) "DiameterJ: A validated open source nanofiber diameter measurement tool," Biomaterials 61:327-338.
Houston, K.A. & Rotstein, O.D., (1988) "Fibrin sealant in high-risk colonic anastomoses," Arch Surg, 123 230-234.
Huber, G. et al. (2005) "Evidence for capillarity contributions to gecko adhesion from single spatula nanomechanical measurements," PNAS 102:16293-16296.
Huber-Lang M. et al. (2018) "Innate immune responses to trauma," Nat Immunol 19:327-41.
Imre, B. and Pukánszky, B. (2013) "Compatibilization in Bio-Based and Biodegradable Polymer Blends," Eur. Polym. J. 49(6):1215-1233.
Jeong, S. I. et al. (2004) "In vivo Biocompatibilty and Degradation Behavior of Elastic Poly(I-Lactide-Co-ϵ-Caprolactone) Scaffolds," Biomaterials 25(28):5939-5946.
Jeong, S. I. et al. (2004) "Manufacture of Elastic Biodegradable PLCL Scaffolds for Mechano-Active Vascular Tissue Engineering," J. Biomater. Sci. Polym. Ed. 15(5):645-660.
Johnsen, B.B. et al. (2007) "Toughening mechanisms of nanoparticle-modified epoxy polymers," Polymer 48(2):530-541.
Jordan, J et al. (2005) "Experimental trends in polymer nanocomposites—a review," Materials Science and Engineering: A, 393:1-11.
Kamel, R. M. (2010) "Prevention of Postoperative Peritoneal Adhesions," Eur. J. Obstet. Gynecol. Reprod. Biol. 150 (2):111-118.
Katti D.S. et al. (2004) "Bioresorbable nanofiber-based systems for wound healing and drug delivery: optimization of fabrication parameters," J Biomed Mater Res B Appl Biomater 70:286-96.
Kern N.G. et al. (2017) "Solution blow spun polymer: A novel preclinical surgical sealant for bowel anastomoses," J Pediatr Surg 52(8):1308-1312.
Ketelson, H.A. et al. (1996) "Colloidal Stability of Stöber Silica in Acetone," Langmuir 12(5):1134-1140.
Kheirabadi, B.S. et al. (2002) "Comparative Study of the Efficacy of the Common Topical Hemostatic Agents with Fibrin Sealant in a Rabbit Aortic Anastomosis Model," Journal of Surgical Research, 106:99-107.
Kim J.S. et al. (2007) "Antimicrobial effects of silver nanoparticles," Nanomedicine 3:95-101.
Kim, I.Y. et al. (2015) "Toxicity of silica nanoparticles depends on size, dose, and cell type, Nanomedicine: Nanotechnology," Biology and Medicine 11:1407-1416.
King, A. et al. (2014) "Dressings and Products in Pediatric Wound Care," Adv. Wound Care 3(4):324-334.
Kong H. and Jang J. (2008) "Antibacterial properties of novel poly(methyl methacrylate) nanofiber containing silver nanoparticles," Langmuir 24:2051-6.
Konieczynska, M. D. et al. (2016) "On-Demand Dissolution of a Dendritic Hydrogel-Based Dressing for Second-Degree Burn Wounds through Thiol-Thioester Exchange Reaction," Angew. Chem. Int. Ed. 55(34):9984-9987.
Lang, N. et al. (2014) "A Blood-Resistant Surgical Glue for Minimally Invasive Repair of Vessels and Heart Defects," Sci. Transl. Med. 6(218):218ra6.
Lantin, A. et al. (2016) "Mepilex XT in Practice: Results of a Study in German Specialist Wound Care Centres," Wound Intl. 7(2):20-24.
Lao, L. L. et al. (2008) "Modeling of Drug Release from Biodegradable Polymer Blends," Eur. J. Pharm. Biopharm. 70(3):796-803.
Lara H.H. et al. (2010) "Bactericidal effect of silver nanoparticles against multidrug-resistant bacteria," World Journal of Microbiology and Biotechnology 26:615-21.
Lee, B. K. et al. (2017) "Silicone-Based Adhesives with Highly Tunable Adhesion Force for Skin-Contact Applications," Adv. Healthc. Mater. 6(22):1700621.
Lee, B.P. et al. (2011) "Mussel-Inspired Adhesives and Coatings," Annual Review of Materials Research, 41:99-132.
Lee, M.-G. M. and Jones, D. (2005) "Applications of Fibrin Sealant in Surgery," Surg. Innov. 12(3):203-213.
Li J. et al. (2003) "Angiogenesis in wound repair: angiogenic growth factors and the extracellular matrix," Microsc Res Tech. 60(1):107-114.
Li, J. et al. (2017) "Tough adhesives for diverse wet surfaces," Science 357:378-381.
Li, T. et al. (2016) "Toughening Glassy Poly(Lactide) with Block Copolymer Micelles," ACS Macro Lett. 5(3):359-364.
Liu, X. et al. (2013) "Mussel-Inspired Polydopamine: A Biocompatible and Ultrastable Coating for Nanoparticles in vivo," ACS Nano 7(10):9384-9395.
Liu, Y. et al. (2017) "A Moldable Nanocomposite Hydrogel Composed of a Mussel-Inspired Polymer and a Nanosilicate as a Fit-to-Shape Tissue Sealant," Angew. Chem. Int. Ed. 56(15):4224-4228.
Maciver, A. H. et al. (2011) "Intra-Abdominal Adhesions: Cellular Mechanisms and Strategies for Prevention," Int. J. Surg. 9(8):589-594.
Manas, D.M. et al. (2016) "Expert opinion on advanced techniques for hemostasis in liver surgery," Eur. J. Surg. Oncol. 42:1597-1607.
Mandell, S. P. and Gibran, N. S. (2014) "Fibrin Sealants: Surgical Hemostat, Sealant and Adhesive," Expert Opin. Biol. Ther. 14(6):821-830.
Mazzeo, F. A. (2002) "Characterization of Pressure Sensitive Adhesives by Rheology," TA Instrum. Rep. RH082, 1-8.
Mecham, S. et al. (2010) "Amphiphilic Silicone Copolymers for Pressure Sensitive Adhesive Applications," J. Appl. Polym. Sci. 116(6):3265-3270.
Menzies, D. (1993) "Postoperative Adhesions: Their Treatment and Relevance in Clinical Practice," Ann. R. Coll. Surg. Engl. 75(3):147-153.
Mir, M. et al., (2017) "Recent Applications of PLGA Based Nanostructures in Drug Delivery," Colloids Surf. B Biointerfaces 159:217-231.
Wang, H. et al. (2017) "Rheology of Nanosilica-Compatibilized Immiscible Polymer Blends: Formation of a "Heterogeneous Network" Facilitated by Interfacially Anchored Hybrid Nanosilica," Macromolecules, 50:9494-9506.

(56) References Cited

OTHER PUBLICATIONS

Waring, M. et al. (2011) "An Evaluation of the Skin Stripping of Wound Dressing Adhesives," J. Wound Care 20(9):412-422.
White, R. (2005) "Evidence for Atraumatic Soft Silicone Dressing Use," Wounds UK 1(3):104-109.
Zhao X. et al. (2017) "Cell infiltrative hydrogel fibrous scaffolds for accelerated wound healing," Acta Biomater 49:66-77.
Wiegand, C. et al. (2019) "Effect of Non-Adhering Dressings on Promotion of Fibroblast Proliferation and Wound Healing in vitro," Sci. Rep. 9(1):1-10.
Yang, B. et al. (2016) "Switch of Surface Adhesion to Cohesion by Dopa-Fe3+ Complexation, in Response to Microenvironment at the Mussel Plaque/Substrate Interface," Chem. Mater. 28(21):7982-7989.
Yuk, H. et al. (2016) "Tough bonding of hydrogels to diverse non-porous surfaces," Nature Materials 15(2):190-196.
Yun H.C. et al. (2016) "Infection After Orthopaedic Trauma: Prevention and Treatment," J Orthop Trauma 30 Suppl 3: S21-S6.
Zahedi P. et al. (2010) "A review on wound dressings with an emphasis on electrospun nanofibrous polymeric bandages," Polym Adv Tehcnol 21:77-95.
Zaulyanov L. and Kirsner R.S. (2007) "A review of a bi-layered living cell treatment (Apligraf®) in the treatment of venous leg ulcers and diabetic foot ulcers," Clinical interventions in aging 2:93.
Zhao G. and Stevens S.E., Jr. (1998) "Multiple parameters for the comprehensive evaluation of the susceptibility of *Escherichia coli* to the silver ion," Biometals 11(1)27-32.
Zhao X. et al. (2016) "Photocrosslinkable Gelatin Hydrogel for Epidermal Tissue Engineering," Adv Healthc Mater 5:108-18.
Eming S.A. (2012) In: Jean L. Bolognia JVS, Lorenzo Cerroni, ed. Dermatology. 3rd ed: Elsevier; 2012: 2313-1325.

* cited by examiner

A
Heat Flow (mW/g)
exo up
Temperature (°C)
PLGA
PLGA-PEG
P-20
P-180
P-620
B
Young's Modulus (Pa)
Room Temp.
Body Temp.
PLGA/PEG
P-20
P-180
P-620
C
Failure Strain (%)
D
Toughness (J/m³)
E
Ultimate Tensile Strength (Pa)

C
Coagulation Time (min)
15
10
5
0
>15 min
*
Control
PLGA
PLGA/PEG
P-20
P-620
D
Sealed PLGA/PEG
E
Sealed P-620
F
Removed after 10 minutes
G
Removed after 10 minutes

Molecular Weight (kDa)

0 10 20 30 40 50 60 70

$M_n$ $M_w$

PLGA

HMW PLCL

LMW PLCL

90:10

70:30

LMW:HMW PLCL

70:30

LMW:HMW PLCL:PLGA

C
TNF-α (pg/mL)
0
5
10
15
20
Saline
PLGA
100:0
70:30
0:100
70:30
LMW:HMW PLCL Ratio
LMW:HMW PLCL:PLGA
D
IFN-γ (pg/mL)
0.0
0.5
1.0
1.5
2.0
2.5
3 Day
10 Day

Figure 23

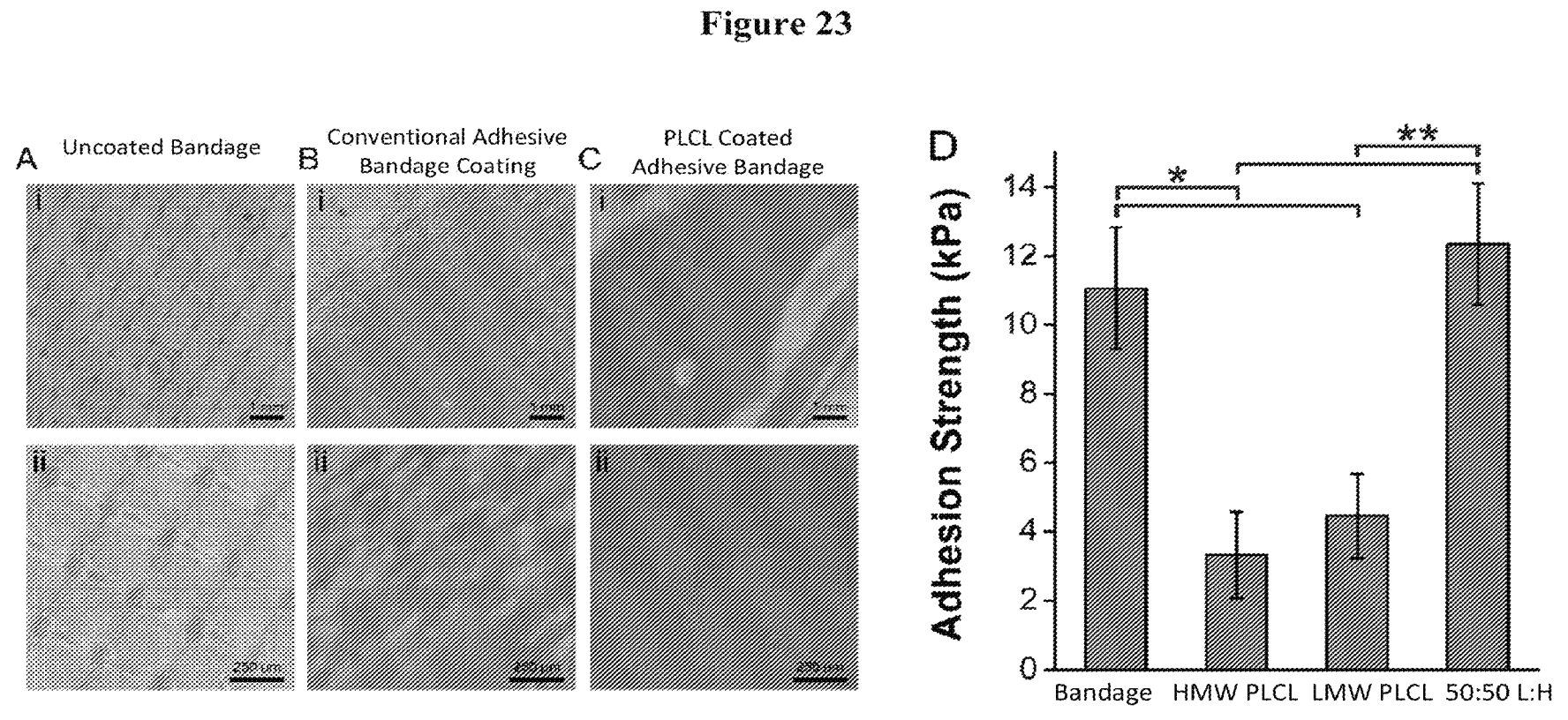

A Uncoated Bandage
i
ii

B Conventional Adhesive Bandage Coating
i
ii

C PLCL Coated Adhesive Bandage
i
ii

D Adhesion Strength (kPa)
0
2
4
6
8
10
12
14
Bandage
HMW PLCL
LMW PLCL
50:50 L:H
*
**

Figure 24

$AgNO_3$ Concentration 0 mg/mL
0.5 mg/mL
1 mg/mL
5 mg/mL

SBS Solvent

Acetone
(a) (b) (c) (d)

Ethyl Acetate
(e) (f) (g) (h)

Figure 32

SOLUTION BLOW SPUN POLYMER CONSTRUCTS, COMPOSITIONS AND METHODS OF FABRICATIONS AND USES RELATING THERETO

CROSS-REFERENCE TO RELATED APPLICATIONS

This application is a § 371 National Stage Application of PCT/US2020/021879, filed Mar. 10, 2020, which application is based on U.S. Provisional Patent Application Ser. No. 62/816,568, entitled "Polymer Blends with Improved Performance in Health Care Applications," filed Mar. 11, 2019, each of which applications application is incorporated herein by reference in its entirety and to which priority is claimed.

STATEMENT REGARDING FEDERALLY SPONSORED RESEARCH OR DEVELOPMENT

This invention was made with government support under R01 EB019963 awarded by the National Institutes of Health. The government has certain rights in the invention.

FIELD

The present disclosure relates to biocompatible polymer compositions, fiber constructs formed from such compositions, methods of fabrication, and uses of such constructs and compositions for treating a tissue defect site.

BACKGROUND

The treatment of tissue wounds and defects from injury and surgical procedures poses a number of challenges for clinicians. Infection in a defect site results in longer healing time and increased morbidity, particularly in large total body surface area (TBSA) wounds. For example, patients with burn wounds covering greater than 40% TBSA have a 75% greater risk of mortality due to infection (Church D. et al. (2006) *Burn wound infections*, Clin Microbiol Rev 19:403-34). Orthopedic trauma and surgery conducted in low resource settings have an extraordinarily high risk of infection (Tribble D. R. et al. (2018) *Epidemiology of Trauma-Related Infections among a Combat Casualty Cohort after Initial Hospitalization: The Trauma Infectious Disease Outcomes Study*, Surg Infect (Larchmt) 19:494-503; Yun H. C. et al. (2016) *Infection After Orthopaedic Trauma: Prevention and Treatment*, J Orthop Trauma 30 Suppl 3:S21-S6). Exposure to infectious agents can cause sepsis and contribute to harmful immune response (Huber-Lang M. et al. (2018) *Innate immune responses to trauma*, Nat Immunol 19:327-41; Nunez Lopez O. et al. (2017) *Predicting and managing sepsis in burn patients: current perspectives*, Ther Clin Risk Manag 13:1107-17).

Conformal bandages are commonly used in treating smaller external wounds, although they are unsuitable for use on large TBSA wounds or wounds irregular in shape and depth. Such bandages are often coated with a pressure-sensitive adhesive (PSA) and can be affixed to a surface by applying pressure to the interface without any curing event. Such PSAs may be composed of acrylic, polyisobutylene (PIB), or poly(styrene-butadiene-styrene) (SBS) block copolymers blended with a phenolic tackifying resin (Deng, X. (2018) *Progress on Rubber-Based Pressure-Sensitive Adhesives*, J. Adhes. 94(2):77-96; Shin, J. et al. (2011) *Pressure-Sensitive Adhesives from Renewable Triblock Copolymers*, Macromolecules 44(1):87-94; Falsafi, A. et al. (2000) *Compositional Effects on the Adhesion of Acrylic Pressure Sensitive Adhesives*, Langmuir 16(4):1816-1824). These PSAs can adhere effectively to skin, which is dry and hydrophobic unlike the wet tissue surfaces of internal tissues. However, they are non-degradable, have been shown to cause allergic dermatitis, and may strip the healing wound of newly deposited tissue (Widman, T. J. et al. (2008) *Allergic Contact Dermatitis from Medical Adhesive Bandages in Patients Who Report Having a Reaction to Medical Bandages*, Dermatitis 19(1):32-37; Waring, M. et al. (2011) *An Evaluation of the Skin Stripping of Wound Dressing Adhesives*, J. Wound Care 20(9):412-422; Wiegand, C. et al. (2019) *Effect of Non-Adhering Dressings on Promotion of Fibroblast Proliferation and Wound Healing in vitro*, Sci. Rep. 9(1):1-10). Moreover, such bandages must be changed frequently to prevent hematoma formation and exudate buildup. Removal can be painful, disrupts the healing epidermis, and increases the risk of infection (Vloemans A. F. et al. (2014) *Optimal treatment of partial thickness burns in children: a systematic review*, Burns 40:177-90; Trott A., Wound Dressing and Bandaging Techniques, Wounds and Lacerations: Emergency Care and Closure, Philadelphia, PA: Elsevier; 2012:266-81). Despite their limitations, PSA bandages are widely used as wound dressings (Rippon, M. et al. (2007) *Skin Adhesives and Their Role in Wound Dressings*, Wounds UK 3(4):76-86; King, A. et al. (2014) *Dressings and Products in Pediatric Wound Care*, Adv. Wound Care 3(4):324-334).

Attempts to improve medical PSAs have focused on reducing damage to the wound during removal, developing switchable chemistries, improving water permeability, and using biologically-derived materials. Formulations such as silicone adhesives have been developed in an attempt to reduce the adherence of healing skin tissue to the adhesive during bandage removal (Pukki, T. et al. (2010) *Assessing Mepilex® Border in Post-Operative Wound Care*, Wounds UK 6(1):30-40; White, R. (2005) *Evidence for Atraumatic Soft Silicone Dressing Use*, Wounds UK 1(3):104-109; Davies, P. et al. (2008) *Evidence Review: The Clinical Benefits of Safetac Technology in Wound Care*, J. Wound Care Suppl, 3-31; Lantin, A. et al. (2016) *Mepilex XT in Practice: Results of a Study in German Specialist Wound Care Centres*, Clin. Pract. 7(2):4; Lee, B. K. et al. (2017) *Silicone-Based Adhesives with Highly Tunable Adhesion Force for Skin-Contact Applications*, Adv. Healthc. Mater. 6(22):1700621). Other formulations have been developed in an attempt to improve water absorption, exudate control, and water transport (Borde, A. et al. (2012) *Increased Water Transport in PDMS Silicone Films by Addition of Excipients*, Acta Biomater. 8(2):579-588; Mecham, S. et al. (2010) *Amphiphilic Silicone Copolymers for Pressure Sensitive Adhesive Applications*, J. Appl. Polym. Sci. 116(6):3265-3270; Deng, W. et al. (2016) *Absorptive Supramolecular Elastomer Wound Dressing Based on Polydimethylsiloxane—(Polyethylene Glycol)—Polydimethylsiloxane Copolymer: Preparation and Characterization*, RSC Adv. 6(57):51694-51702). Other adhesive formulations have been developed in an attempt to enhance biocompatibility (Nasiri, M. et al. (2018) *Enhanced Mechanical and Adhesion Properties in Sustainable Triblock Copolymers via Non-Covalent Interactions*, Macromolecules 51(7):2456-2465; Czech, Z. et al. (2013) *Biodegradable Self-Adhesive Tapes with Starch Carrier*, Int. J. Adhes. Adhes. 44:195-199). However, such developments have yielded only limited success, with effectiveness highly dependent on the specific characteristics of the particular wound in clinical studies (Sood, A. et al. (2014) *Wound Dressings and Comparative Effectiveness Data*, Adv. Wound Care 3(8):511-529).

Hydrogel dressings attempt to address the limitations associated with conventional bandages. Hydrogel dressings provide a moist wound healing environment that can be delivered as soft, moldable material (Sun G. et al. (2011) *Dextran hydrogel scaffolds enhance angiogenic responses and promote complete skin regeneration during burn wound healing*, Proc Natl Acad Sci USA 108:20976-81; Zhao X. et al. (2016) *Photocrosslinkable Gelatin Hydrogel for Epidermal Tissue Engineering*, Adv Healthc Mater 5:108-18). When removal is necessary, they can be dissolved on-demand by exchanging crosslinks (Konieczynska M. D. et al. (2016) *On-Demand Dissolution of a Dendritic Hydrogel-based Dressing for Second-Degree Burn Wounds through Thiol-Thioester Exchange Reaction*, Angewandte Chemie International Edition 55:9984-7). They also provide improved absorption of wound exudate and oxygen permeation because of their high porosity, but are typically pre-fabricated using electrospinning (Zahedi P. et al. (2010) *A review on wound dressings with an emphasis on electrospun nanofibrous polymeric bandages*, Polym Adv Tehenol 21:77-95; Katti D. S. et al. (2004) *Bioresorbable nanofiber-based systems for wound healing and drug delivery: optimization of fabrication parameters*, J Biomed Mater Res B Appl Biomater 70:286-96; Zhao X. et al. (2017) *Cell infiltrative hydrogel fibrous scaffolds for accelerated wound healing*, Acta Biomater 49:66-77). While such attempts have provide some advantages, limitations remain with regard the need for wound contact, adequate exudate absorption, and/or adhesive properties.

In addition to conventional bandages, surgical adhesives or sealants are also used to supplement conventional wound closure devices by covering or filling the gaps of a closed wound with a layer of adhesive material (N. Annabi et al. (2015) *Elastic sealants for surgical applications*, European Journal of Pharmaceutics and Biopharmaceutics, 95:27-39). Surgical sealants may be used in addition to sutures to repair or close tissues that are at risk for leak, infection, or blood loss. Sealants may also be used to reduce tissue damage, e.g., by securing organs or biomedical devices non-invasively, potentially eliminating the need for sutures or staples in some surgical procedures.

Tissue sealing is necessary following many surgical procedures or traumatic injuries. Resections, biopsies, and accidental trauma may damage tissue and its vasculature and may require surgical reconstruction and hemostasis. Conventional wound closure devices like sutures are limited in their ability to seal some wounds due to tissue gaps, suture failure, or suture dehiscence (K. Schäfer et al. (1989) *Disorders of microcirculation in colon anastomoses and their significance for the pathogenesis of suture dehiscence*, Langenbecks Arch Chir. 375:24-32; N. Annabi et al. (2014) *Surgical materials: Current challenges and nano-enabled solutions*, Nano Today 9:574-589). For example, in defined procedures such as bowel anastomosis, leaks occur at a rate of 5-17% depending on patient characteristics (J. Hammond et al. (2014) *The Burden of Gastrointestinal Anastomotic Leaks: an Evaluation of Clinical and Economic Outcomes*, Journal of Gastrointestinal Surgery, 18:1176-1185; S. Chittmittrapap et al. (1992) *Anastomotic leakage following surgery for esophageal atresia*, Journal of Pediatric Surgery, 27:29-32). Leaks can cause sepsis, a systemic infection with high morbidity and mortality rates, and therefore pose a challenging heath care issue for both diagnosis and treatment (C. Rhee et al., *CDC Prevention Epicenter Program, Incidence and Trends of Sepsis in US Hospitals Using Clinical vs Claims Data,* 2009-2014, JAMA (2017)). Similarly, achieving hemostasis remains an unavoidable and difficult challenge in tissue injury, especially for at-risk patients (A. M. Behrens et al. (2014) *Hemostatic strategies for traumatic and surgical bleeding: Hemostatic Strategies for Traumatic and Surgical Bleeding*, Journal of Biomedical Materials Research Part A, 102:4182-4194).

Many conventional tissue adhesives, such as fibrin glue, rely on a curing step to become sticky (B. S. Kheirabadi et al. (2002) *Comparative Study of the Efficacy of the Common Topical Hemostatic Agents with Fibrin Sealant in a Rabbit Aortic Anastomosis Model*, Journal of Surgical Research, 106:99-107). Commercial packages of fibrin glue contain a solution of fibrinogen and a solution of thrombin that are loaded into a dual-barrel syringe (Mandell, S. P. and Gibran, N. S. (2014) *Fibrin Sealants: Surgical Hemostat, Sealant and Adhesive*, Expert Opin. Biol. Ther. 14(6):821-830). Other examples of tissue adhesives with two-component mixing and gelation include various synthetic hydrogels, which crosslink upon mixing (Cencer, M. et al. (2014) *Effect of PH on the Rate of Curing and Bioadhesive Properties of Dopamine Functionalized Poly(Ethylene Glycol) Hydrogels*, Biomacromolecules 15(8):2861-2869; Barrett, D. G. et al. (2013) *Mechanically Robust, Negative-Swelling, Mussel-Inspired Tissue Adhesives*, Adv. Healthc. Mater. 2(5):745-755; Konieczynska, M. D. et al. (2016) *On-Demand Dissolution of a Dendritic Hydrogel-Based Dressing for Second-Degree Burn Wounds through Thiol-Thioester Exchange Reaction*, Angew. Chem. Int. Ed. 55(34):9984-9987; Bu, Y. et al. (2019) Tetra-PEG Based Hydrogel Sealants for In vivo Visceral Hemostasis, Adv. Mater. 31(28):1901580). Cyanoacrylate glues polymerize at the interface with tissue and rapidly solidify (C. O. Ensari et al. (2010) *Effects of N-butyl-2-cyanoacrylate on high-level jejunojejunostomy*, Eur Surg Res, 44 (2010) 13-16). Some one-component, light-cured tissue adhesives have been developed to simplify deposition in an attempt to control timing of the curing step (Annabi, N. et al. (2017) *Engineering a Highly Elastic Human Protein-Based Sealant for Surgical Applications*, Sci. Transl. Med. 9(410):eaai7466; Annabi, N. et al. (2017) *Engineering a Sprayable and Elastic Hydrogel Adhesive with Antimicrobial Properties for Wound Healing*, Biomaterials 139:229-243; Alleyne, C. H. et al. (1998) *Efficacy and Biocompatibility of a Photopolymerized, Synthetic, Absorbable Hydrogel as a Dural Sealant in a Canine Craniotomy Model*, J. Neurosurg. 88(2):308-313; Lang, N. et al. (2014) *A Blood-Resistant Surgical Glue for Minimally Invasive Repair of Vessels and Heart Defects*, Sci. Transl. Med. 6(218):218ra6).

To allow for the curing step, the tissue adhesive precursors in all such conventional adhesives must be deposited as liquids onto the surgical site, which makes them difficult to apply effectively because they are prone to dripping off vertical structures and/or into adjacent tissue spaces. The application of such adhesives is particularly difficult in minimally invasive procedures where specialized applicators are required (Lee, M.-G. M. and Jones, D. (2005) *Applications of Fibrin Sealant in Surgery*, Surg. Innov. 12(3):203-213; Heher, P. et al. (2018) *An Overview of Surgical Sealant Devices: Current Approaches and Future Trends*, Expert Rev. Med. Devices 15(10):747-755). Inaccurate application may lead to longer surgery times or cause unforeseen complications, such as thromboembolism (Samudrala, S. (2008) *Topical Hemostatic Agents in Surgery: A Surgeon's Perspective*, AORN J. 88(3):S2-S11; Spotnitz, W. D. (2001) *Commercial Fibrin Sealants in Surgical Care*, Am. J. Surg. 182(2, Supp 1):S8-S14). Additionally, water and protein present on the surface of internal tissues prevents sufficient adhesion of such conventional materials for internal applications (N. Lang et al. (2014) *A Blood-Resistant Surgical Glue for Minimally Invasive Repair of Vessels and Heart Defects*, Sci Transl Med 6:218ra6; see also Ahn, B. K. (2017) *Perspectives on Mussel-Inspired Wet Adhesion*, J. Am. Chem. Soc. 139(30):10166-10171; Yang, B. et al. (2016) *Switch of Surface Adhesion to Cohesion by Dopa-Fe3+ Complexation, in Response to Microenvironment at the Mussel Plaque/Substrate Interface*, Chem. Mater. 28(21):7982-7989). However, conventional tissue adhesives lack cohesive properties that promote strong adhesive bonding.

Attempts to enhance tissue adhesion in sealants have primarily focused on the formation of covalent bonds with tissue proteins and curing materials in situ (P. J. M. Bouten et al. (2014) *The chemistry of tissue adhesive materials*, Progress in Polymer Science 39:1375-1405). Some tissue adhesives incorporate functional groups to bond to tissue, such as dopamine via oxidation, chitosan via electrostatics, N-hydroxysuccinimide, which reacts with amines in tissue, or oxidized dextran, also via amines (Liu, Y. et al. (2017) *A Moldable Nanocomposite Hydrogel Composed of a Mussel-Inspired Polymer and a Nanosilicate as a Fit-to-Shape Tissue Sealant*, Angew. Chem. Int. Ed. 56(15):4224-4228; J. Li et al. (2017) *Tough adhesives for diverse wet surfaces*, Science 357:378-381; Strehin, I. et al. (2010) *A Versatile PH Sensitive Chondroitin Sulfate-PEG Tissue Adhesive and Hydrogel*, Biomaterials 31(10):2788-2797; Artzi, N. et al. (2009) *Characterization of Star Adhesive Sealants Based On PEG/Dextran Hydrogels*, Macromol. Biosci. 9(8):754-765). However, such attempts have resulted in increased cytotoxicity, swelling, and poor biodegradability (B. Mizrahi et al. (2011) *Elasticity and safety of alkoxyethyl cyanoacrylate tissue adhesives*, Acta Biomaterialia 7:3150-3157; J. Henise et al. (2016) *Surgical sealants with tunable swelling, burst pressures, and biodegradation rates*, Journal of Biomedical Materials Research Part B: Applied Biomaterials 105:1602-1611).

Conventional surgical sealants have therefore produced mixed results in clinical applications due to their limitations, often failing to improve patient outcomes over other conventional techniques (A. C. van der Ham et al., *Effect of fibrin sealant on the healing colonic anastomosis in the rat*, Br J Surg, 78 (1991) 49-53; K. A. Houston & O. D. Rotstein, *Fibrin sealant in high-risk colonic anastomoses*, Arch Surg, 123 (1988) 230-234). Accordingly, there is a need for biocompatible compositions suitable for use as surgical sealants and wound dressings that solve one or more of the limitations associated with conventional techniques.

SUMMARY OF THE DISCLOSURE

The present disclosure relates to polymer compositions suitable for use as surgical sealants, adhesives, hemostatic materials and/or scaffolding materials, e.g., on the wound or target tissue of a subject.

In accordance with disclosed embodiments, a biocompatible composition comprises a solution comprising: (i) between about 1% and about 20% weight per volume (w/v) low molecular weight (LMW) polymer; and (ii) between about 1% and about 20% w/v high molecular weight (HMW) polymer. In some implementations, the HMW polymer is poly(lactide-co-caprolactone) (PLCL). In other implementations, the HMW polymer is poly(lactide-co-glycolide) (PLGA). In some embodiments, the HMW polymer and/or the LMW polymer is poly(lactide-co-caprolactone) (PLCL).

In some embodiment, the composition, after deposition (e.g., after the composition has been sprayed and dried), yields a solid adhesive comprising a ratio of the LMW polymer to the HMW polymer ranging from 90:10 to 20:80 by weight. In some embodiments, the composition, after deposition (e.g., after the composition has been sprayed and dried), yields a solid adhesive comprising a ratio of LMW polymer to HMW polymer ranging from 80:20 to 30:70 by weight (given all or substantially all of the solvent in the solution, e.g., acetone, evaporates and is not present in the resulting solid adhesive). In some embodiments, the weight ratio of the LMW polymer to the HMW polymer of the solid adhesive is about 50:50 by weight. In some embodiments, the weight ratio of the LMW polymer to the HMW polymer of the solid adhesive is about 70:30 by weight.

In some embodiments, the composition additionally comprises a suspension of between about 1% and about 20% w/v silica particles based on the volume of the solution. In some implementations, the suspension comprises between about 1% and about 10% w/v silica particles based on the volume of the solution, or about 5% silica particles based on the volume of the solution. In some implementations, the silica particles have an average diameter of between about 1 nanometer (nm) and about 1000 nm, or between about 10 nm and about 800 n. In some implementations, the silica particles have an average diameter of: i) between about 10 nm and about 30 nm; or ii) between about 150 nm and about 250 nm; or iii) between about 500 nm and about 700 n.

In some embodiments, the solution additionally comprises between about 0.01% and about 1% w/v therapeutic agent based on the volume of the solution. In some implementations, the therapeutic agent is a protein, a peptide, an amine, an aliphatic compound and/or an antibiotic. In some implementations, the solution comprises an antibiotic, e.g., which is silver nitrate. In some implementations, the solution comprises between about 0.05% and about 0.5% w/v silver nitrate. In some implementations, the solution comprises about 0.1% w/v silver nitrate.

The present disclosure is also directed to a composition comprising a solution comprising (i) between about 1% and about 20% weight per volume (w/v) poly(lactic-co-glycolic acid) (PLGA); and (ii) between about 1% and about 20% w/v poly(ethylene glycol) (PEG); and a suspension of between about 1% and about 20% w/v silica particles based on the volume of the solution. In some implementations, the suspension comprises between about 1% and about 15% w/v silica particles based on the volume of the solution, or between about 3% and about 10% w/v silica particles based on the volume of the solution, or about 5% w/v silica particles based on the volume of the solution.

In some embodiments, the PLGA/PEG/silica composition comprises silica particles having an average diameter of between about 1 nanometer (nm) and about 1000 nm, preferably between about 10 nm and about 800 n. In some implementations, the composition comprises silica particles having an average diameter of: i) between about 10 nm and about 30 nm; or ii) between about 150 nm and about 250 nm; or iii) between about 500 nm and about 700 n.

The present disclosure also relates to a biocompatible composition comprising a solution comprising (i) between about 1% and about 20% weight per volume (w/v) poly (lactic-co-glycolic acid) (PLGA); (ii) between about 1% and about 20% w/v poly(ethylene glycol) (PEG); and (iii) between about 0.01% and about 1% w/v therapeutic agent based on the volume of the solution. In some embodiments, the therapeutic agent is selected from the group consisting of a protein, a peptide, an amine, an aliphatic compound, and an antibiotic. In some implementations, the solution comprises an antibiotic, e.g., which is silver nitrate. In some implementations, the solution comprises between about 0.05% and about 0.5% w/v silver nitrate, or about 0.1% silver nitrate.

In some embodiments, the disclosed compositions, e.g., the PLGA/PEG/silica composition and/or the PLGA/PEG/Ag composition, comprises a solution comprises between about 5% and about 15% w/v PLGA. In some embodiments, the solution comprises between about 1% and about 10% w/v PEG. In some embodiments, the solution comprises about 10% w/v PLGA and about 5% w/v PEG. In some embodiments, the solution comprises one or more volatile solvent, e.g., acetone or ethyl acetate.

In some embodiments, the PLGA/PEG/silica composition comprises a solution that additionally comprises a therapeutic agent (e.g., silver nitrate). In some embodiments, the PLGA/PEG/Ag composition may additionally comprise a solution additionally comprising a suspension of silica particles as described above. Thus, components of some of the disclosed compositions may be implemented in other of the disclosed compositions.

The present disclosure also relates to use of the disclosed compositions in the treatment of an external wound on a subject, such as a skin wound such as from a burn or other trauma. The burn wound and/or other skin wound. The disclosed compositions are also suitable for use as a surgical sealant, adhesive, hemostatic material or scaffolding material on an internal tissue site, such as on the heart or other organ, bone, or other internal tissue. Accordingly, the present disclosure provides for use of the disclosed compositions as a sprayable surgical sealant, adhesive, hemostatic or scaffolding material.

The present disclosure also relates to a biocompatible polymer fiber construct comprising blow spun polymer fibers formed from any of the disclosed compositions. In some embodiments, the construct is a tissue sealant, adhesive, hemostatic or scaffolding material. In some implementations, the construct is formed of polymer fibers having an average diameter of less than about 12 micrometers (μm). In some implementations, the polymer fibers have an average diameter of between about 1 μm and about 10 μm, or between about 2 μm and about 6 μm.

The present disclosure also relates to a method of forming a polymer fiber construct, comprising: forming a plurality of polymer fibers using a solution blow spinning process, wherein the polymer fibers are formed from one or more of the disclosed compositions; and depositing the plurality of blow spun polymer fibers onto a target to form a conformal polymer fiber construct thereon. In some implementations, the target is an internal or external tissue surface. The polymer fiber construct may be formed on such tissue surface in vivo.

The present disclosure also relates to methods of treating a wound on a subject comprising depositing a surgical sealant, adhesive, hemostatic or scaffolding material on the wound, wherein such sealant, adhesive, hemostatic or scaffolding material is formed from one or more of the compositions disclosed herein.

BRIEF DESCRIPTION OF THE DRAWINGS

FIG. 23, Panels A-C, are optical microscopy images of a plastic bandage coated with polybutylene adhesive (Panel A), with the polybutylene adhesive removed (Panel B), and coated with PLCL blend adhesive (Panel C). Biodegradable PLCL pressure sensitive adhesives were sprayed onto plastic bandages, producing comparable adhesive strength to a conventional polybutylene pressure sensitive adhesive. Panel D shows graphically adhesion strength between bandage and porcine skin during pull-apart adhesion testing.

FIG. 32, Panel A, illustrates RT-PCR measurements of wound healing genes α-smooth muscle actin (α-SMA), vascular endothelial growth factor (VEGF), transforming growth factor-β1 (TGF-β1), collagen I, and collagen III on PWD 35 (n=8). Gene expression measured relative to those of normal uninjured skin. Panel B shows ratio of collagen I expression to collagen III expression. Panel C shows number of required dressing replacements per wound due to dressing adherence (n=8). Asterisks indicate statistical significance: *p<0.05; p<0.01; *p<0.001.

DETAILED DESCRIPTION OF EMBODIMENTS

Figure 1:
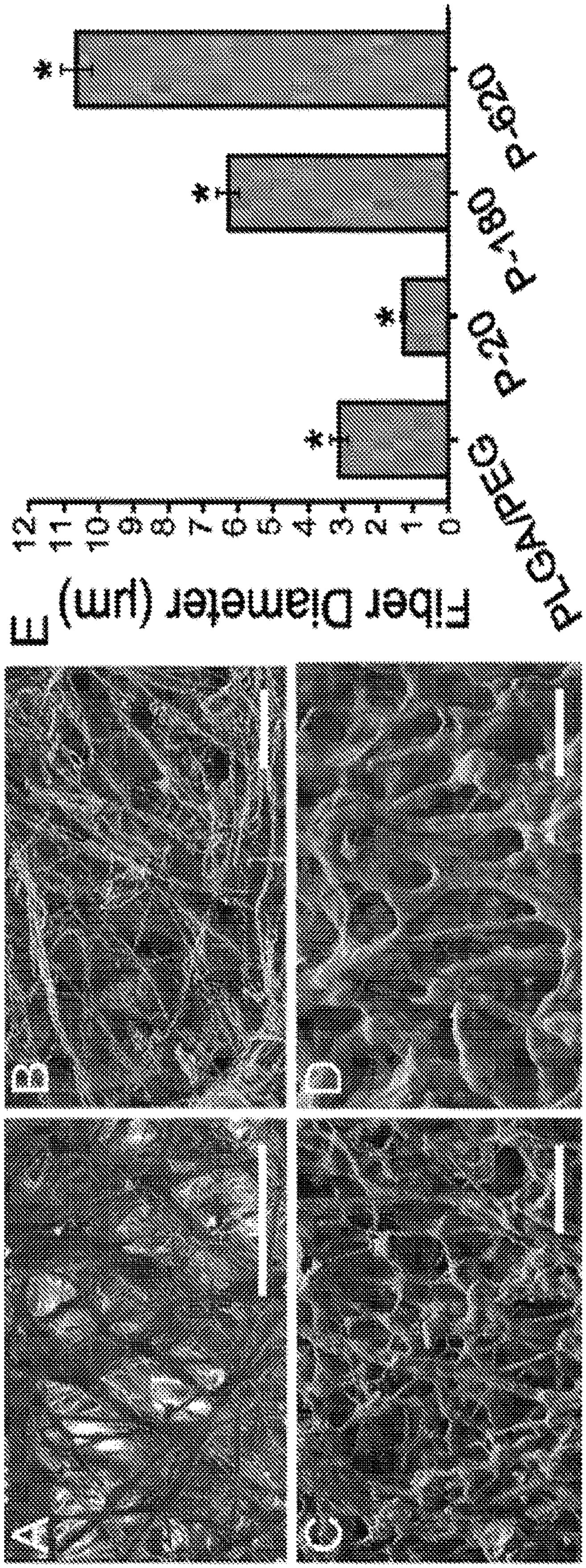
FIG. 1, Panels A, B, C and D, are scanning electron microscope (SEM) images of fiber mats sprayed from: (Panel A) PLGA/PEG: 10% w/v PLGA, 5% w/v PEG solution in acetone; (Panel B) P-20: 10% w/v PLGA, 5% PEG, 5% 20 nm silica nanoparticles; (Panel C) P-180: 10% w/v PLGA, 5% PEG, 5% 180 nm silica nanoparticles; and (Panel D) P-620: 10% w/v PLGA, 5% PEG, 5% 620 nm silica nanoparticles. Scale bars=50 μm. As shown, particle size can increase or decrease the fiber diameter produced by solution blow spinning suspensions of silica particles in a polymer blend solution. Panel E shows graphically average fiber diameter measured from 20 fibers in 3 images using ImageJ. Asterisk indicates statistically significant difference ($p<0.01$) between the groups.

The present disclosure is directed to various polymer compositions suitable for use as surgical sealants, adhesives, hemostatic materials and scaffolding materials, e.g., including sprayable and biodegradable wound dressings and sealants. In some embodiments, a polymer composition is provided that comprises a blend of low and high molecular weight biodegradable polymers that exhibit tissue adhesive properties. The adhesive formulations may be sprayed using solution blow spinning to form a fibrous device that transitions to a conformal film. Adhesion is responsive to pressure in a time-dependent manner. In accordance with disclosed embodiments, a pressure-sensitive tissue adhesive (PSTA) is provided that can be fixed to tissue (e.g., intestinal or cardiac tissue) simply by applying pressure to the interface, and without any curing event, thereby drastically improving usability. A bimodal polymer blending strategy is employed to produce an inherently tacky and tissue adhesive polymer film that is biodegradable, biocompatible, and sprayable. By varying polymer chemistry of the blend, control over viscoelasticity and biodegradation rate of the PSTA is achieved, allowing polymer compositions to be selectively tuned depending on the intended application.

In some embodiments, a composition is provided that comprises a polymer blend of poly(lactic-co-glycolic acid) (PLGA) and poly(ethylene glycol) (PEG), and nano- to micro-scale particles. The resulting compositions demonstrate enhanced wet tissue adherence due in part to the incorporation of the silica particles, and without significantly affecting cell viability, biodegradation rate, or local inflammation. In particular, the incorporation of silica particles into a synthetic polymer surgical sealant increases interfacial physical bonding to tissue and increases the energy dissipated by the bulk matrix, yielding greater burst pressure while producing no significant increase in cytotoxicity, local inflammation, or biodegradation.

In functional studies, the PLGA/PEG/silica composite sealants exhibited intestinal burst pressures comparable to that of cyanoacrylate glue (156 mmHg), about 2 times greater burst pressure compared to conventional non-composite sealant (59 mmHg), and about 3 times greater burst pressure compared to fibrin glue (48.6 mmHg). Further, the addition of silica particles to the polymer blends is biocompatible with sprayable in situ deposition methods such as solution blow spinning. As demonstrated by the disclosed data, the sealants demonstrate decreased coagulation time in vitro and in vivo, and cause minimal additional inflammation. The disclosed sealants therefore provide significant advantages over conventional formulations, including an increase in wet tissue adhesion through physical, noncovalent mechanisms, enabling the use of the composite sealants in procedures requiring simultaneous occlusion and hemostasis.

For ease of use and accurate application, the surgical sealant may be spray-deposited as a conformal polymer fiber mat using solution blow spinning (SBS). Poly(lactic-co-glycolic acid) (PLGA) and polyethylene glycol (PEG), a biodegradable and bioabsorbable polymer blend, can be spray-deposited as fibers using SBS, yet transitions into a soft, conformal film after warming to body temperature (see A. M. Behrens et al. (2015) *Biodegradable-Polymer-Blend-Based Surgical Sealant with Body-Temperature-Mediated Adhesion*, Advanced Materials, 27:8056-8061; N. G. Kern et al. (2017) *Solution blow spun polymer: A novel preclinical surgical sealant for bowel anastomoses*, J Pediatr Surg 52(8):1308-1312). Silica particles are suspended in a PLGA/PEG blend solution that can be deposited in situ as composite fibers directly onto wet soft tissues.

As known in the art, wet tissue presents a variety of hydrophilic surface chemistries, making adherence challenging (N. Artzi et al. (2011) *Tuning adhesion failure strength for tissue-specific applications*, Acta Biomater 7:67-74). Through a combination of nanotexture and crack suppression, the silica particles in the disclosed compositions increase the flexibility, adhesion strength, and adhesion energy of the composite sealant. As demonstrated by the data herein, the incorporation of silica particles decreases blood coagulation time. When exposed to blood, the silica particles induce coagulation that is complementary to the occlusion provided by the surgical sealant. The adhesive and hemostatic effects of the PLGA/PEG/silica composite sealant was validated in an ex vivo model of intestinal anastomosis and an in vivo liver laceration model. In contrast with conventional strategies of enhancing adhesion through covalent bonding, the simple incorporation of silica particles in the disclosed composite sealants produces virtually no change in cell viability or local inflammation, as demonstrated in an in vivo intraperitoneal implantation model.

Thus, the sealants disclosed herein improve upon conventional devices given they may be easily deposited with accuracy directly onto the surgical site as a solid polymer fiber mat. The deposition method (SBS) allows for high loading in the composite fibers, which are sprayed from a polymer blend solution containing suspended silica particles. The compositions and techniques disclosed herein may therefore be readily translated to various implantable or wearable devices due in part to the versatility of silica particles.

The present disclosure also relates to adhesive compositions comprising a blend of poly(lactic-co-glycolic acid) and poly(ethylene glycol) (PLGA/PEG), and silver (Ag) particles. In accordance with disclosed methods, the PLGA/PEG/Ag composition may be sprayed using solution blow spinning (SBS) for the deposition of biodegradable polymer fibers containing antimicrobial silver directly onto a wound site. Unlike electrospinning, which uses an applied voltage to drive fiber production and has low production rates, SBS uses a pressurized gas to produce fibers from a polymer solution (A. M. Behrens et al. (2014) *In Situ Deposition of PLGA Nanofibers via Solution Blow Spinning*, ACS Macro Lett 3(3):249-254; Daristotle J. L. et al. (2016) *A Review of the Fundamental Principles and Applications of Solution Blow Spinning*, ACS Applied Materials & Interfaces 8:34951-63). The incorporation of silver salts in the solution provides for a sprayable and antimicrobial wound dressing (PLGA/PEG/Ag), which may be sprayed (e.g., with a portable airbrush) directly onto the wood for sealing, and releases bactericidal silver ions that reduce the risk of infection. Commonly used silver salts have broad-spectrum antimicrobial activity with relatively low minimum inhibitory concentrations (MIC) and minimum bactericidal concentrations (MBC) (Kim J. S. et al. (2007) *Antimicrobial effects of silver nanoparticles*, Nanomedicine 3:95-101; Ayala-Nunez, N. et al. (2009) *Silver Nanoparticles Toxicity and Bactericidal Effect against MEthicillin Resistant Staphylococcus aureus: Nanoscale Does Matter*, Nanobiotechnology 5:2-9; Lara H. H. et al. (2010) *Bactericidal effect of silver nanoparticles against multidrug-resistant bacteria*, World Journal of Microbiology and Biotechnology 26:615-21; Rai M. et al. (2009) *Silver nanoparticles as a new generation of antimicrobials*, Biotechnol Adv 27:76-83; Percival S. L. et al. (2005) *Bacterial resistance to silver in wound care*, J Hosp Infect 60:1-7; Morones-Ramirez J. R. et al. (2013) *Silver enhances antibiotic activity against gram-negative bacteria*, Sci Transl Med 5:190ra81).

The effects of silver nitrate ($AgNO_3$) on silver ion ($Ag^+$) release, mechanical properties, and adhesion of PLGA/PEG was examined. In vitro studies were used to determine the optimal concentration of $AgNO_3$ loaded into PLGA/PEG spinning solutions. To demonstrate the feasibility of using PLGA/PEG and PLGA/PEG/Ag wound dressing compositions, they were evaluated in an in vivo porcine partial-thickness wound model. The incorporation of biodegradable PLGA/PEG into the scab and its absorption of wound exudate was examined using histology and fluorescence microscopy. Dressing changes were made as needed and tracked to demonstrate the benefits of using an intrinsically adhesive dressing that could biodegrade and be absorbed by the wound.

The disclosed compositions may be used to form a biodegradable fibrous polymer construct via a solution blow spinning process. The composite materials exhibit enhanced adhesion to wet tissue, increased flexibility, and enhanced hemostatic efficacy as compared to conventional compositions. In addition, the composites exhibit a desirable biodegradation rate and sufficiently low cytotoxicity.

Additional characteristics and features of the present disclosure will be further understood through reference to the following additional examples and discussion, which are provided by way of further illustration and are not intended to be limiting of the present disclosure.

Example 1

Surgical Sealant Compositions Containing Silica Particles

Materials and Methods

Polymer Deposition and Polymer Solutions: An airbrush (Master Airbrush, G222-SET, 0.2 mm nozzle diameter) was used to deposit the surgical sealants (A. M. Behrens et al. (2014) *In Situ Deposition of PLGA Nanofibers via Solution Blow Spinning*, ACS Macro Lett 3(3):249-254). The airbrush was connected to a compressed $CO_2$ tank equipped with a pressure regulator set to 20 psig. Unless stated otherwise, fiber mats were produced by solution blow spinning onto a 22 mm by 22 mm glass coverslip, with the distance between airbrush nozzle and cover slip at approximately 10 cm. For 500 μL of polymer solution, the spraying process typically produces 16±5 mg of polymer fiber sample on the coverslip (n=60). The typical thickness of the fiber mat is approximately 160±30 mm for this solution volume and consistent across the sample (Behrens, A. M. et al. (2015) *Biodegradable-polymer-blend-based surgical sealant with body-temperature-mediated adhesion*, Adv. Mater. 27:8056-8061). All polymer solutions were dissolved in acetone, with 10% w/v PLGA (inherent viscosity=0.86 dL $g^{-1}$ in hexafluoroisopropanol, $M_n$=48800±500 g $mol^{-1}$ measured with gel permeation chromatography against polystyrene standards, 50:50, Lactel), 5% w/v PEG ($M_n$=950-1050 g $mol^{-1}$, Sigma-Aldrich, St. Louis, MO). 5% w/v silica particles (e.g., 50 mg/mL) were suspended in the PLGA/PEG solutions and dispersed by sonication. ~180 nm and ~620 nm silica particles were synthesized according to a modified Stöber process and washed with deionized water. 10-20 nm silica nanopowder was purchased from Sigma-Aldrich. Dynamic light scattering (DLS, Zetasizer Nano ZS90) was used to determine the hydrodynamic diameter of the Stöber particles.

Morphology Characterization: Fiber samples were produced by solution blow spinning (SBS) 200 μL of polymer solution onto glass cover slips. The distance between airbrush nozzle and cover slip was 10 cm. For scanning electron microscopy (SEM, Hitachi SU-70), fiber samples were sputter-coated with gold before imaging. Fiber diameter was measured from SEM images in ImageJ (National Institutes of Health). Average fiber diameter was calculated for each sample using two different images, with 20 measurements made in each. When fibers were selected for measurement, nodes or intersections between fibers were not measured. Porosity was estimated using the DiameterJ plug-in for ImageJ (n=12, 3 SEM images per group) (Hotaling, N. A. et al. (2015) *Diameter J: A validated open source nanofiber diameter measurement tool*, Biomaterials 61:327-338). Transmission electron microscopy (TEM) was performed on a JEOL 2100 F using samples of fibers placed between two TEM grids.

Burst Pressure Testing: Porcine small intestine was purchased from a local butcher and cleaned with water prior to use. The small intestine was cut into 10 cm segments, and the ends were closed with zip ties for testing. A half diameter incision was made to simulate a leaky anastomosis. Tissue was rehydrated and heated to 37° C. by soaking in 37° C. phosphate buffered saline (PBS) for two minutes, followed by exposure to 37° C. air for four minutes, repeating this process twice, and finally drying with gauze (Fisherbrand). Approximately 500 μL of polymer solution was deposited directly onto the intestinal tissue using the SBS process described above. For cyanoacrylate and fibrin glue (Tisseel, Baxter), 500 μL of adhesive was applied. After applying the adhesive, it was allowed to set for 15 minutes at 37° C.

Once the adhesive was set, the intestine was connected to the burst pressure testing setup as diagrammed in FIG. 2A. A syringe was used to inject 1×phosphate buffered saline (PBS) dyed with 0.05% methylene blue into the intestine at a constant rate using a 18 gauge needle. A digital pressure gauge was attached to the injection line using a three-way stopcock to measure the injection pressure. The maximum pressure prior to bursting or leakage was recorded as the burst pressure. The entire test was captured on video so that the failure mode could be determined. Each adhesive was tested five times (n=5).

Interfacial Imaging: Samples of porcine small intestine were rehydrated and heated to 37° C. using the same procedure as samples for burst pressure testing, but during the last rehydration step, PBS was replaced with a solution of 33% glycerol in PBS to preserve the samples during freezing. 500 μL of polymer solution was deposited directly onto a sample of small intestine. The samples were submerged in liquid nitrogen and fractured to produce a cross-section of the interface between intestinal tissue and surgical sealant. SEM (Hitachi SU-70) was used to image the samples, which were sputter-coated with gold before imaging.

Differential Scanning Calorimetry (DSC): Fiber samples were produced by solution blow spinning (SBS) 500 μL of polymer solution. The resulting fiber mats were removed from the coverslips and trimmed to yield 10 mg samples of fibers. The samples were then sealed in aluminum hermetic pans (TA Instruments) using a sample encapsulation press. DSC measurements were made on a TA Instruments DSC Q100. Samples were held isothermal at −50° C. for 5 min and then heated and cooled from −50 to 80 to −50° C., at a rate of 3° C. $min^{-1}$, +0.20° C. amplitude, with a modulation period of 60 s for two continuous cycles. $T_g$ onset was calculated using the tangent intersection method on the reversing heat flow. The inflection point of the reversing heat flow during the $T_g$ was used to determine the midpoint.

Polydopamine (PDA) coated Particle Synthesis: PDA coated particles were synthesized by dispersing 180 nm silica particles at 0.1% in an oxidizing solution of 10 mM tris(hydroxymethyl)aminomethane (TRIS, pH 8.5) buffer with 2 mg mL-1 dopamine hydrochloride (Sigma-Aldrich, St. Louis, MO). This mixture was reacted for varying amounts of time (1-16 h) with stirring in a round bottom flask.

Thermal Properties and Second DSC Scan: Approximately 10 mg samples of fiber mats were sealed in aluminum hermetic pans (TA Instruments) using a sample encapsulation press. DSC measurements were made on a TA Instruments DSC Q100. Samples were held isothermal at −50° C. for 5 min and then heated and cooled from −50 to 80 to −50° C., at a rate of 3° C. min⁻1, ±0.20° C. amplitude, with a modulation period of 60 s for two continuous cycles. $T_g$ onset was calculated using the tangent intersection method on the reversing heat flow. The inflection point of the reversing heat flow during the $T_g$ was used to determine the midpoint.

Mass Spectrometry: Matrix-assisted laser desorption/ionization-time of flight mass spectrometry analysis (MALDI-TOF) was performed on the supernatant of a PLGA/PEG in vitro degradation sample after 1 day. An Agilent 6890N GC system with a JEOL JMS-700 MStation on an Agilent VF-5MS column was used, with a 30 m×0.25 mm ID×0.25 mm film thickness, helium at 1 mL/min, injector temperature of 285° C., and an injection volume of 1 μL. The oven temperature program was set to: (1) Hold 1.0 min at 50° C., (2) ramp 18° C./min to 310° C., and (3) hold 4.56 min at 310° C.

Tensile Testing: Fiber samples were produced by SBS 500 mL of polymer solution. The resulting fiber mats were removed from the coverslips and trimmed to a rectangular shape, approximately 10 mm by 5 mm in size. Exact sample dimensions were measured immediately prior to testing. Tensile tests were made using a TA Instruments DMA Q800 equipped with a film tension clamp. Samples were stretched under a controlled force ramp from 0 N to 5 N at a rate of 0.001 N/min. Measurements were made either at room temperature or at 37° C. after a 10 min isothermal period. Elastic modulus was calculated from the linear region of the resulting stress/strain curve. Each sample type was replicated 5 times (n=5).

Pull-off Adhesion Testing: Fiber samples were produced by SBS 2 mL of polymer solution. The resulting fiber mats were removed from the coverslips and folded into 5 mm by 5 mm samples that weighed approximately 50 mg. Thickness was measured for each sample prior to testing, and averaged 0.9±0.1 mm across all fiber samples. For fibrin glue, samples with similar size and mass were created by depositing approximately 50 mL of Tisseel (Baxter International Inc., Deerfield IL). Pull-off testing was performed on the TA Instruments DMA Q800. Before testing the samples, each 1 cm clamp was coated with 50 μL of 20 mg mL-1 Type 1 Collagen (rat tail) solution (Sigma-Aldrich, St. Louis, MO). A 50 mg sample of surgical sealant was compressed at 0.001 N of force for 30 minutes at 37° C. before testing to allow for a complete thermal transition to occur. After compressing at 1 N for 1 min, a controlled force ramp was used to increase pull-off force at a rate of 1 N $min^{-1}$ until failure, also at 37° C. Failure type was recorded as either adhesive or cohesive. Each sample type was replicated five times (n=5).

Wound Closure Adhesion Testing: Wound closure adhesion testing was performed on the TA Instruments DMA Q800. 1 cm by 1 cm sections of porcine small intestine were attached to rectangular clamps using cyanoacrylate glue. The rectangular clamps were brought together end to end, and 1 mL of sealant polymer solution or 50 μL of cyanoacrylate glue, or 50 μL of fibrin glue (Tisseel, Baxter International Inc., Deerfield, IL) was deposited on this joint, closing the gap between the two intestine-coated clamps (see ASTM F2458-05, Standard Test Method for Wound Closure Strength of Tissue Adhesives and Sealants (2015)). The sealant was carefully applied and trimmed to avoid coating the interface between the ends and edges of the clamps. It was then allowed to set at 37° C. for 10 minutes before testing. A controlled force ramp was used to increase force at a rate of 1 N $min^{-1}$ until failure. Failure type was recorded as either adhesive or cohesive. Force values were normalized to the surface area of intestine coated by the adhesive, which was measured using calipers, giving adhesive strength. Each sample type was replicated five times (n=5).

Cell Viability: Cell viability was assessed in vitro with L929 mouse fibroblasts (ATCC #CCL-1) using a WST-1 assay. L929s were cultured in media consisting of Dulbecco's minimum essential medium supplemented with 10% fetal bovine serum, 1% streptomycin and 1% glutamine. Cells were plated at $10^4$ cells per well in 100 μL of media in a 96 well plate and incubated at 37 C and 5% $CO_2$ for 24 hours. The culture media was then replaced with sealant extract samples. The sealant extracts samples were prepared by SBS of polymer solution onto a sterile glass coverslip. Stock extracts from sealant samples were prepared by immersing 50 mg of sample in 500 μL of the culture media at 37° C. for 24 h. Fiber mat samples were produced by SBS 2 mL of polymer solution onto a sterile 22 mm by 22 mm glass coverslip. The resulting fiber mats were removed from the glass coverslips and folded into samples that weighed approximately 50 mg. Cells were then cultured in 100 μL dilutions of the stock extract at 37° C. for 24 h: 1× dilution (100% stock extract), 10× dilution (10% stock extract in fresh media), and 100×dilution (10% stock extract media in fresh media). The control media was not exposed to a surgical sealant sample. The positive control was puromycin at 25 μg $mL^{-1}$ in culture media. Viability was measured at 24 hours using an WST-1 assay (Roche). Absorbance was measured at 480 nm using a Synergy-H4 plate reader (BioTek). This experiment was repeated 4 times for each extract (n=4).

Degradation: Samples of polymer blend surgical sealant were prepared on glass coverslips by SBS 2 mL of polymer solution. A microbalance (Sartorius ME-5) was used to determine the net increase in mass after the spinning process was complete, which is the initial sample mass, $m_i$. Samples were placed in 6 well plates, submerged in 4 mL of 1× PBS, and stored in a shaker incubator at 37° C. and 50 rpm. PBS was exchanged every 48 h for 28 days to prevent pH change. Samples were removed at time points of 0, 1, 3, 7, 14, and 28 days. At these points, the PBS was removed, and the samples were stored in a vacuum desiccator for three days. The samples were weighed again to determine the final mass, $m_f$, and mass loss ($m_i$−$m_f$) was calculated as a percentage of $m_i$. Samples that swell with water may produce a negative mass loss because of incomplete water removal and salt that remains in the polymer matrix. Five samples were used for each time point and surgical sealant type (n=5).

Coagulation Time: Citrated whole sheep blood was warmed to 37° C. First, 1 mL of whole blood was added and mixed in a glass vial containing 10 mg of polymer blend surgical sealant samples, which were collected from fiber mats blow spun onto glass coverslips. Immediately after this step, the blood was recalcified using a 0.2 M $CaCl_2$) stock, yielding a final $CaCl_2$) concentration in blood of 10 mM. Coagulation was assessed by vial inversion (Behrens, A. M.

et al. (2014) *Blood-aggregating hydrogel particles for use as a hemostatic agent*, Acta Biomater 10(2):701-708; Scola, M. R. et al. (2012) *A review of current methods for assessing hemostasis in vivo and introduction to a potential alternative approach*, Thromb Res 129:S57-S61). Coagulation time was defined as when the entire sample was stagnant during inversion. A Lab-quake rotator was used to invert the vials continuously while they were being examined for complete coagulation. Control trials received no surgical sealant. The experiment was repeated 5 times (n=5) for each type of surgical sealant.

Hemostatic Testing in Porcine Liver Laceration: All animal procedures were approved by the Children's National Medical Center Institutional Animal Care And Use Committee (IACUC Protocol #00030454), and the animals were treated in accordance with PHS Policy on Humane Care and Use of laboratory Animals, the National Institute of Health Guide for the Care and Use of Laboratory Animals, and the Animal Welfare Act. A 15 kg female Yorkshire swine (Archer Farms, MD, USA) was used. After intubation and sedation per standard protocol, a midline laparotomy was made. Four 2 cm lacerations and two wedge resections were separately made on the liver (total of 6 wounds, n=3 per group). Sealant was applied immediately after wound creation. Liver wounds were assessed for bleeding after application of sealant. Surgical sealant was removed to assess the degree of hemostasis at the liver wounds after 10 minutes.

Intraperitoneal Space Implantation Model: All animal procedures were approved by the Children's National Medical Center Institutional Animal Care And Use Committee (IACUC protocol #00030703), and the animals were treated in accordance with PHS Policy on Humane Care and Use of laboratory Animals, the National Institute of Health Guide for the Care and Use of Laboratory Animals, and the Animal Welfare Act. Eighteen, 7-15 week-old C57BL/6 female mice were used (Jackson Laboratory, ME). Mice were randomized into three groups based on type of implant: control (saline injection), PLGA/PEG, and P-620 implants. Experimental endpoints were 3 days and 10 days from initial surgery. A total of three mice were allocated to each treatment group per endpoint. Surgical sealant implants were made under sterile conditions by SBS of desired polymer solution onto a sterile cover slip then cut into 5 mm disks weighing approximately 10 mg using a sterile skin biopsy punch (Acuderm, FL). After processing, the implants were sterilized by UV irradiation.

All mice were anesthetized with a solution of ketamine and xylazine. Buprenorphine was given for analgesic at the start of the surgery and then every 12 hours for 48 hours. After anesthesia, the mice were positioned supine, abdominal hair removed, and then skin prepped with betadine solution. In sterile fashion, a 1 cm laparotomy incision was made at the midline. After dissection into the peritoneal cavity, the 5 mm diameter surgical sealant disks were implanted into the right lower quadrant. For the saline injection control, 0.2 mL of sterile saline was dripped into the right lower quadrant. Animals were sacrificed 3 or 10 days after initial surgery. After euthanasia, cardiac puncture was performed for serum cytokine assessment. Midline laparotomy was also performed, and images of the peritoneal cavity were taken with a 15-megapixel digital camera (Canon, USA). The intraperitoneal space was then examined by a surgeon for signs of inflammation.

Histological Analysis and Disk Diameter: Surgical sealant implants along with surrounding tissue were retrieved from the intraperitoneal space for analysis. The sealant disks were measured after retrieval, and the change in size was calculated as a fraction of the original 5 mm diameter. Then, surgical sealant and surrounding tissue were prepared for histology by paraffin fixation. 5 μm sections were stained with hematoxylin and eosin.

Serum Inflammatory Cytokine Analysis: Whole blood was collected via sterile syringe and 25-gauge needle. In sterile, uncoated vials, blood was allowed to clot over 15 minutes, then serum extracted from supernatant after centrifugation for 15 minutes at 4° C. and 2000 RPM. Serum was stored at −80° C. until ELISA analysis for INFγ and TNFα. Analysis was performed using ELISA kits (Mouse TNFα High Sensitivity ELISA and Mouse INFγ Platinum ELISA, Invitrogen, NY) on serum samples in duplicate. Serum concentrations were interpolated from standard curves.

Statistical Analysis: A one-way ANOVA was used to analyze variance between groups in studies with more than two experimental groups, followed by Tukey's multiple comparisons test with $\alpha=0.05$ to determine between which two groups there was a significant difference. All error bars are equal to the standard error. Statistical analysis was performed in Origin 8.

Results

Solution Blow Spinning of Polymer-Silica Composite Fibers: Composite fiber sealants were deposited in situ by SBS polymer-particle mixtures in acetone from an airbrush. Silica particles were suspended in a polymer solution of 10% w/v PLGA and 5% w/v PEG dissolved in acetone. Particles were suspended at a concentration of 5% w/v and formed an opaque but homogenous mixture, a unique property of silica, which has high colloidal stability in acetone (H. A. Ketelson et al. (1996) *Colloidal Stability of Stöber Silica in Acetone*, Langmuir 12(5):1134-1140). Particles added in concentrations greater than 5% suspended inconsistently and soon after mixing produced aggregates that settled.

Silica particles were used to study the effect of particle size on adhesion primarily because they can be synthesized in monodisperse size distributions, allowing the effect of particle size to be isolated. We utilized the Stöber process to synthesize spherical particles with monodisperse hydrodynamic diameter distributions of 180 nm and 620 nm, as measured by dynamic light scattering (DLS) (W. Stöber et al. (1968) *Controlled growth of monodisperse silica spheres in the micron size range*, Journal of Colloid and Interface Science, 26:62-69). Silica nanopowder with size range of 10-20 nm, which is used in FDA-approved pharmaceutical applications, was also tested. Together, these groups of particles span a size range from approximately 10 nm to 1 μm (Table 1). Combinations of 10% w/v PLGA, 5% w/v PEG, and 5% w/v particles in acetone were studied to determine the effect of particle size on adhesion to tissue, fiber morphology, and mechanical properties. The corresponding weight fractions, volume fractions, and specific surface area of the particles in the solid is provided in Table 2. Blends containing particles are denoted "P-X," where X is the average particle diameter.

TABLE 1

Composition of spinning solutions for tested polymer blend surgical sealants incorporating silica particles.

| Name | % PLGA [w/v] | % PEG [w/v] | % Particle [w/v] | Particle Diameter [nm] | Particle Zeta Potential [mV] | Particle Type |
|---|---|---|---|---|---|---|
| PLGA/PEG | 10 | 5 | 0 | N/A | N/A | N/A |

TABLE 1-continued

Composition of spinning solutions for tested polymer blend surgical sealants incorporating silica particles.

| Name | % PLGA [w/v] | % PEG [w/v] | % Particle [w/v] | Particle Diameter [nm] | Particle Zeta Potential [mV] | Particle Type |
|---|---|---|---|---|---|---|
| P-20 | 10 | 5 | 5 | 19.1 ± 2.3[a)] | −36.7 ± 1.7[a)] | Silica nano-powder |
| P-180 | 10 | 5 | 5 | 181.1 ± 1.8 | −43.9 ± 0.2 | Stober silica |
| P-620 | 10 | 5 | 5 | 619.0 ± 8.2 | −41.9 ± 0.2 | Stober silica |

[a]Characterized previously (D. Sahu et al. (2016) *In vitro Cytotoxicity of Nanoparticles: A Comparison between Particle Size and Cell Type*, Journal of Nanoscience, Vol 2016, ID 4023852).

TABLE 2

Weight fractions (w), volume fractions (φ), and estimated specific surface area of particles (calculated using particle diameter from Table 1) for solid composite sealants incorporating silica particles.

| Solid Sealant | $W_{plga}$ | $W_{peg}$ | $W_{particle}$ | $(\Phi)_{plga}$ | $(\Phi)_{peg}$ | $(\Phi)_{particle}$ | Specific Surface Area [$m^2$/g] |
|---|---|---|---|---|---|---|---|
| PLGA/PEG | 0.67 | 0.33 | 0 | 0.64 | 0.36 | 0 | N/A |
| P-20 | 0.50 | 0.25 | 0.25 | 0.54 | 0.30 | 0.16 | 143.0 |
| P-180 | 0.50 | 0.25 | 0.25 | 0.54 | 0.30 | 0.16 | 15.1 |
| P-620 | 0.50 | 0.25 | 0.25 | 0.54 | 0.30 | 0.16 | 4.4 |

Figure 2:
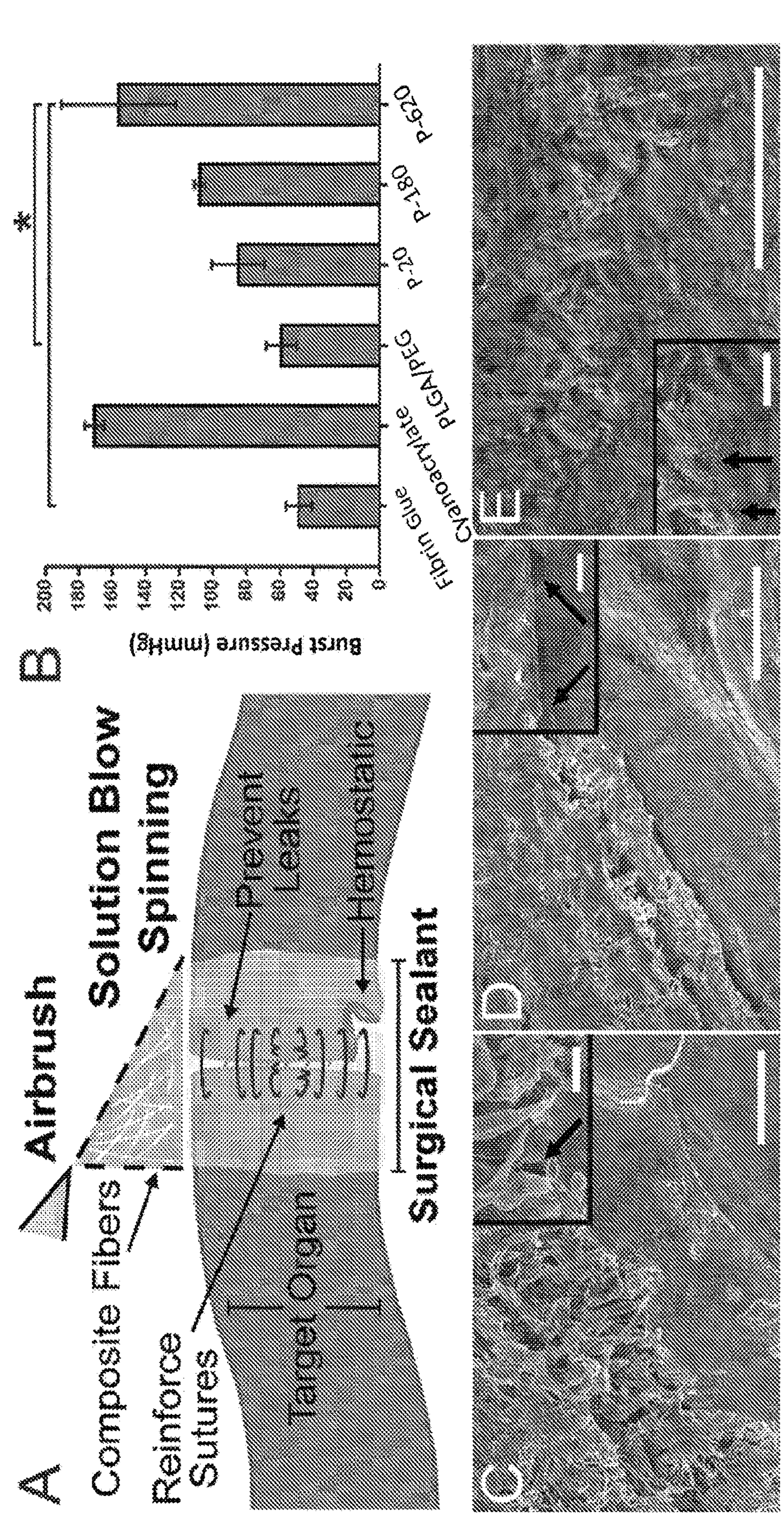
FIG. 2, Panel A, illustrates schematically direct deposition of polymer composite fibers onto a target tissue. Panel B shows graphically average burst pressures measured for different surgical sealants. Asterisk indicates statistically significant difference ($p<0.01$) between the groups. Scanning electron microscope (SEM) images of intestinal tissue-sealant interface are shown for: (Panel C) PLGA; (Panel D) PLGA/PEG; and (Panel E) P-620. Arrows in Panels C-D indicate voids between the polymer and porcine intestinal tissue. Arrows in Panel E indicate silica particles at the interface between polymer and tissue. Scale bars=50 μm for main image, 5 μm for inset. Composite surgical sealants are denoted "P-X", where "X" is the diameter of the silica particles incorporated into PLGA/PEG.

Particle size can increase or decrease the fiber diameter produced by solution blow spinning suspensions of silica particles in a polymer blend solution. In particular, increasing particle size increased the diameter of fibers produced. Fiber morphology changed from relatively thin, long, and bundled fibers to thick, branching fiber webs (FIG. 1, Panels A-D). Fiber diameters were greater when particles of greater diameter were used (FIG. 1E). Using a portable airbrush, the SBS process allows for direct deposition onto a target organ for surgical sealing and hemostasis (FIG. 2, Panel A). The porosity of all fiber mats averaged 49±7%, with no significant differences between any two spinning solutions used.

Figure 3:
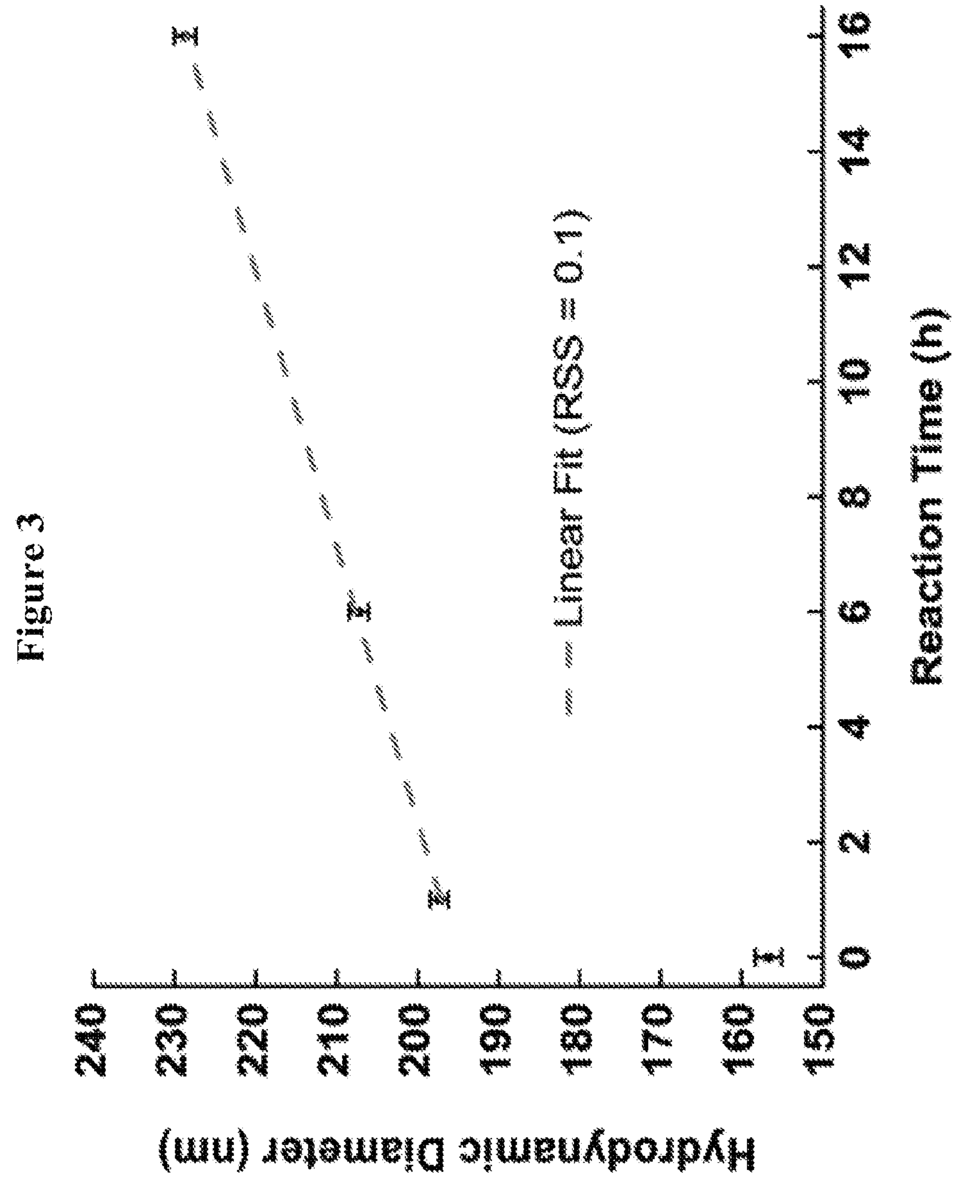
FIG. 3 illustrates graphically diameter of particles coated using a polydopamine coating procedure for varying amounts of time. Hydrodynamic diameter was determined by dynamic light scattering (DLS).

Particle Surface Chemistry Does Not Affect Burst Pressure: To examine the effects of a surface chemistry that may be able to form covalent bonds with tissue, we coated 180 nm silica particles with PDA by dispersing them in an oxidizing buffer solution with dopamine. An established protocol was adapted to enable coating of a suspension of silica particles (X. Liu et al. (2013) *Mussel-Inspired Polydopamine: A Biocompatible and Ultrastable Coating for Nanoparticles in vivo*, ACS Nano 7(10):9384-9395). Oxidizing dopamine produces a quinone chemical structure that is reactive with amines and thiols, functional groups that are present in the proteins composing tissue (B. P. Lee et al. (2011)*Mussel-Inspired Adhesives and Coatings*, Annual Review of Materials Research, 41:99-132). A reaction time of 1 hour produced a PDA coating that was approximately 8 nm thick, yet had colloidal stability in acetone-based polymer solutions at a concentration of 5% w/v (P-180 PDA, FIG. 3). Burst pressure for P-180 PDA was 108±4 mmHg on intestinal tissue, nearly identical to P-180 (no functionalization), indicating that PDA surface functionalization does not contribute to adhesion.

Figure 4:
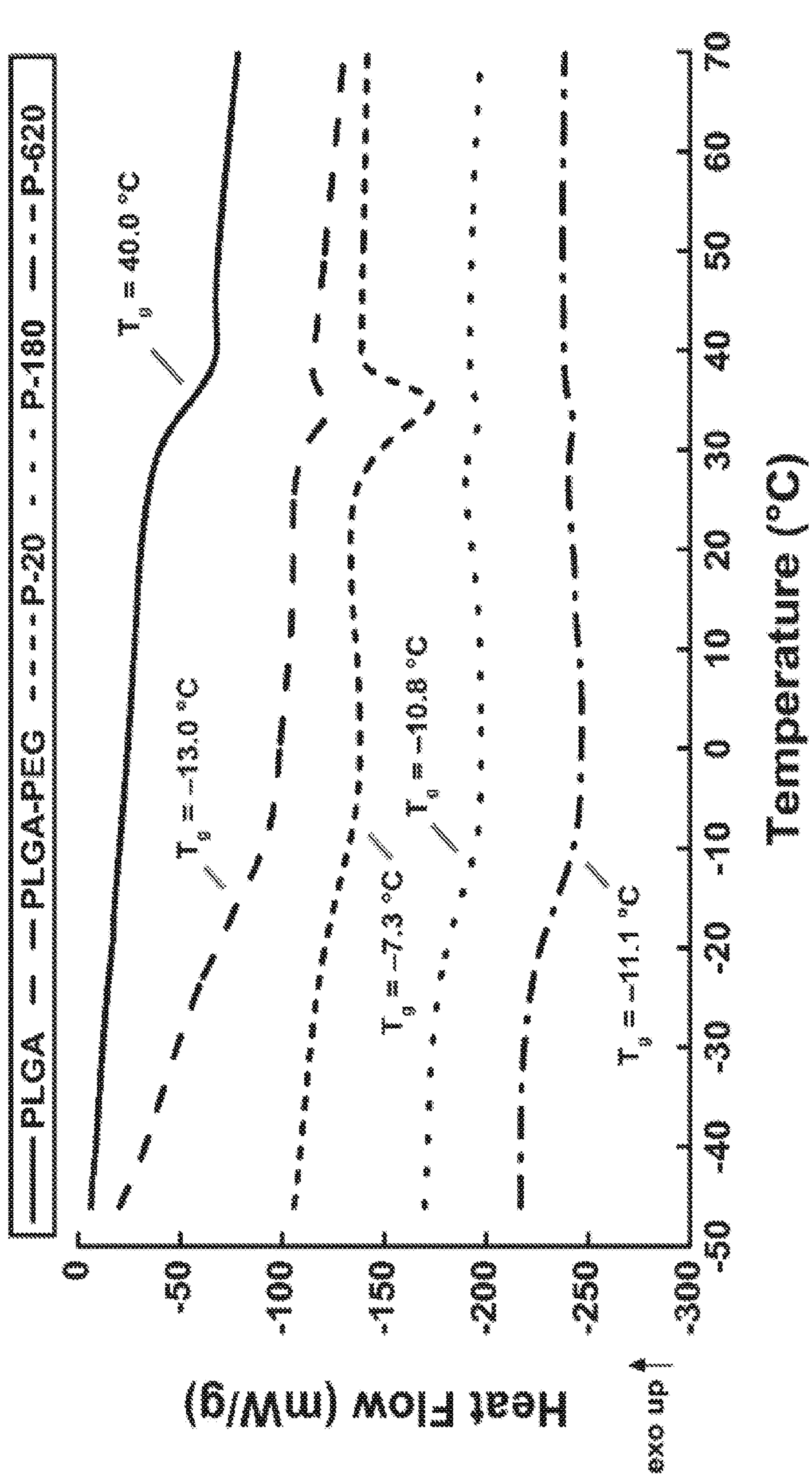
FIG. 4 shows second run differential scanning calorimetry (DSC) scans of various polymer blends. Curves have been shifted vertically for clarity, and $T_g$ is labeled.

Silica Increases Glass Transition Temperature: The potential for a particle-mediated change in $T_g$ prompted an investigation into the thermal properties of each sealant after the first heating cycle using MDSC. Depending on their surface interactions, particles can facilitate the emulsification of immiscible polymer blends or exhibit a preference for bonding to one of the two polymers (H. Wang et al. (2017) *Rheology of Nanosilica-Compatibilized Immiscible Polymer Blends: Formation of a "Heterogeneous Network" Facilitated by Interfacially Anchored Hybrid Nanosilica*, Macromolecules, 50:9494-9506). The $2^{nd}$ run MDSC scans in FIG. 4 show that there is an increased endothermic peak following the $T_g$ of the blend in the presence of silica particles (Table 3). Despite the miscibility of PLGA and PEG, and their ability to hydrogen bond with hydroxyl groups on the bare silica surface, the silica particle may act as nucleation site for the recrystallization of PEG. This explains why P-20 also has a second run enthalpy of melting ($\Delta H_m$) equivalent to 25% of its first run $\Delta H_m$: during the $2^{nd}$ run MDSC (Table 3): the silica particles in P-20 have greater specific surface area (Table 2), which provide more nucleation sites for recrystallization during the cooling cycle.

TABLE 3

Summary of thermal properties of polymer blend surgical sealants incorporating silica particles.

| Name | 1st Run $T_m$ [° C.] | 1st Run $\Delta H_m$ [J/g] | 2nd Run $T_g$ Onset [° C.] | 2nd Run $T_g$ [° C.] | 2nd Run $\Delta H_m$ [J/g] | Visual Transition Time [min] |
|---|---|---|---|---|---|---|
| PLGA | N/A | N/A | 36.1 | 40.0 | N/A | N/A |
| PLGA/PEG | 28.1 | 29.1 | −23.6 | −13.0 | 0.9 | 13 |
| P-20 | 27.0 | 17.2 | −19.2 | −7.3 | 4.3 | 23 |
| P-180 | 24.8 | 15.9 | −19.6 | −10.8 | 0.2 | 17 |
| P-620 | 30.4 | 14.5 | −21.7 | −11.1 | 0.2 | 15 |

Sequestration of PEG at the particle surface, which decreases the amount of PEG available to plasticize PLGA, also accounts for the large increase in $T_g$ observed for P-20. Additionally, silica nanoparticles have also been observed to increase $T_g$ through attractive surface interactions in other silica-polymer nanocomposites (P. Rittigstein and J. M. Torkelson (2006) *Polymer-nanoparticle interfacial interactions in polymer nanocomposites: Confinement effects on glass transition temperature and suppression of physical aging*, Journal of Polymer Science Part B: Polymer Physics, 44:2935-2943). The $T_g$s of P-180 and P-620, which have less particle specific surface area due to increased particle size, are similar compared to the PLGA/PEG control, lending further support to the explanation that surface area-dependent effects are decreasing $T_g$.

Figure 5:
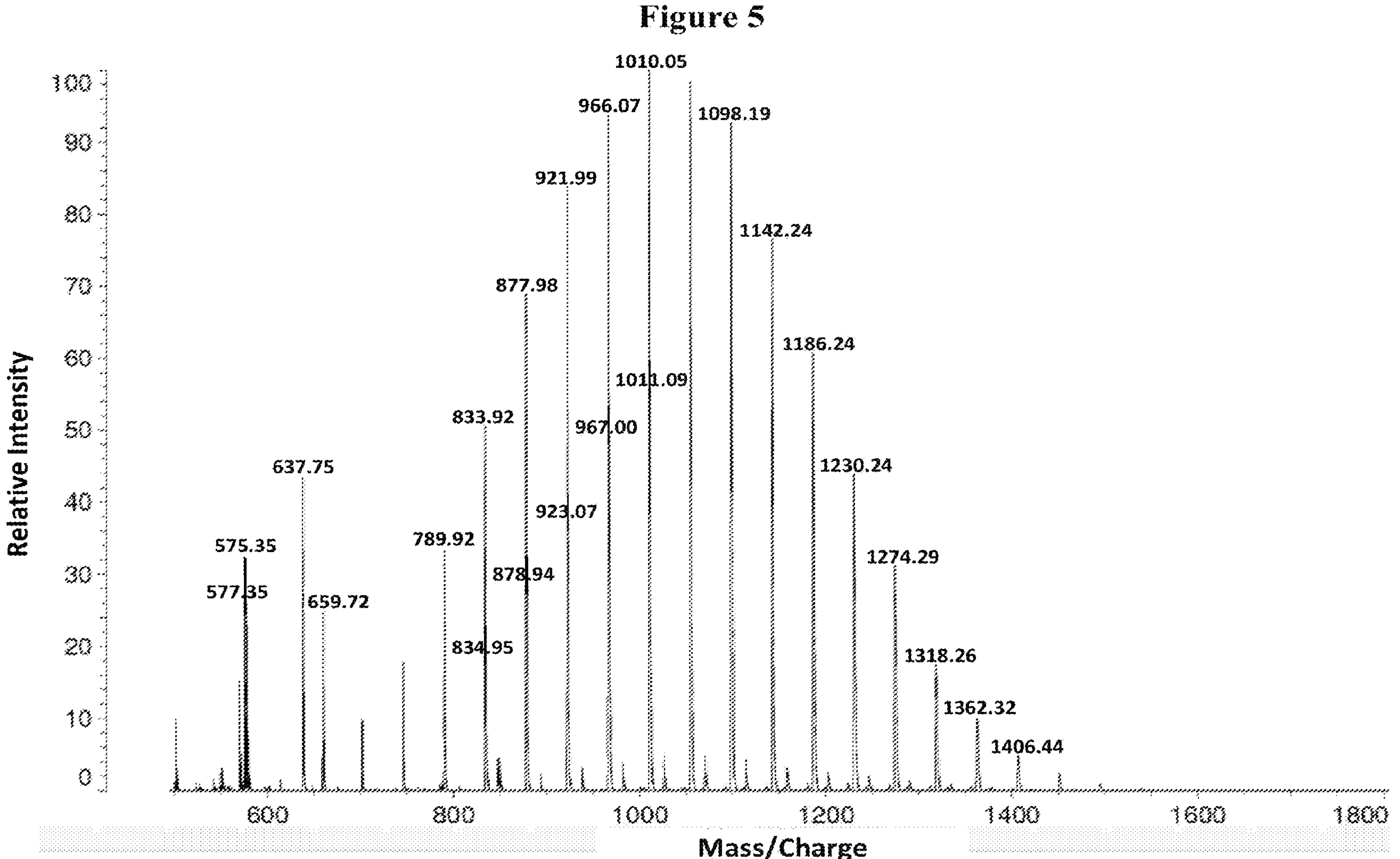
FIG. 5 shows matrix-assisted laser desorption/ionization-time of flight mass spectrometry analysis (MALDI-TOF) of PLGA/PEG sample after 1 day of in vitro biodegradation.

Mass Spectrometry Analysis of Degradation Supernatant: Matrix-assisted laser desorption/ionization-time of flight mass spectrometry analysis (MALDI-TOF) was used to analyze the supernatant of the PLGA/PEG sample after 1 day (FIG. 5). Consistent with PLGA's degradation rate, the spectra show primarily PEG (1000 Da).

Figure 6:
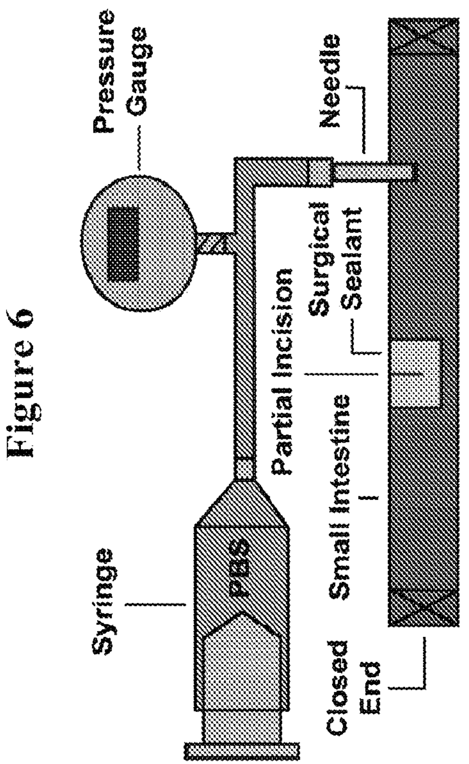
FIG. 6 illustrates schematically an exemplary ex vivo burst pressure testing setup with intestine in accordance with the present disclosure.

Tissue Adhesion of Composite Sealants Depends on Silica Particle Size: Performance of polymer-particle composite surgical sealants is enhanced by incorporating silica particles. Tissue adhesion was assessed in a representative ex vivo model, by performing burst pressure testing on sealed segments of porcine intestinal tissue (FIG. 6). Particle-polymer composite sealants produced greater burst pressures than the non-composite control (FIG. 2, Panel B). P-620, the composite fiber sealants containing the largest nanoparticles tested, resulted in a burst pressure of 160±30 mmHg, approximately double the burst pressure recorded for PLGA/PEG sealants containing no nanoparticles (59.0±3 mmHg, p=0.007) and fibrin glue (49±8 mmHg, p=0.002), a clinical control. P-620's average burst pressure was similar to those observed with cyanoacrylate glue (171±6 mmHg), which is the most tissue adherent sealant amongst clinical controls. Intermediate particle sizes also resulted in increases in burst pressure relative to the control. Approaches to chemically modify the surface of the particles with polydopamine functional groups did not increase burst pressure.

Samples of intestinal tissue were sealed ex vivo at 37° C., cryo-preserved, and freeze-fractured to create a cross-sectional image of the interface between tissue and sealant. This provided imaging of the particles in P-620 that can interact with PLGA polymer chains and proteins from both sides of the interface. While PLGA fiber mats have minimal surface contact due to their fibrous morphology (FIG. 2, Panel C), PLGA/PEG becomes a film that evenly coats the tissue (FIG. 2, Panel D). Unlike either PLGA or PLGA/PEG, P-620 forms a tight interface with tissue and has micro-scale texture (FIG. 2, Panel E). Despite transitioning to a conformal film, many micron-sized regions of P-620 show the ability to bond to tissue simultaneously, instead of behaving as one film with a flat interface. The interface of P-620 with tissue has little to no void space (FIG. 2, Panel E, inset, arrows) even when compared to PLGA and PLGA/PEG, which despite being conformal have gaps in tissue coverage (FIG. 2, Panel C, inset, and FIG. 2, Panel D, inset, arrows).

Thermal and Mechanical Properties are Affected by Silica Particle Size: Differences in thermal and mechanical properties of the sealants contributed to the differences in burst pressure observed between different composite sealants. Toughness, stiffness, extensibility, and transition temperature affect the sealant's ability to form a conformal fiber mat during deposition, transition rapidly into an adherent film, and change in shape as the intestine expands with fluid. A sealant will ideally exhibit low stiffness, high toughness, and high extensibility, such that it can be deformed without restricting the natural change in the intestine's shape under physiological forces, while the transition temperature will occur above room temperature but below body temperature (37° C.) to allow for the deposition of fibers that set to become a coherent film during surgery.

Figure 7:
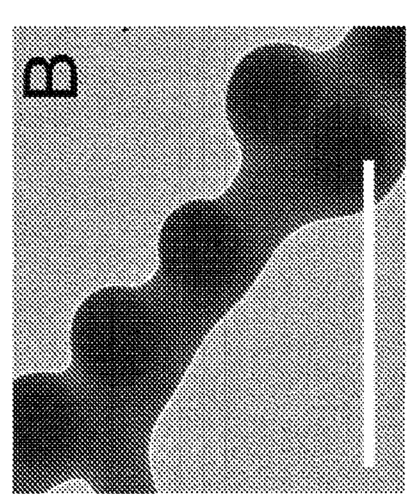
FIG. 7, Panels A and B, are transmission electron microscope (TEM) images of P-620 fibers. Scale bars=2 μm. Silica particles were homogenously distributed throughout fibers produced by solution blow spinning, and also present at the surface of fibers as shown. Surface roughness is roughly proportional to particle diameter.
Figure 7:
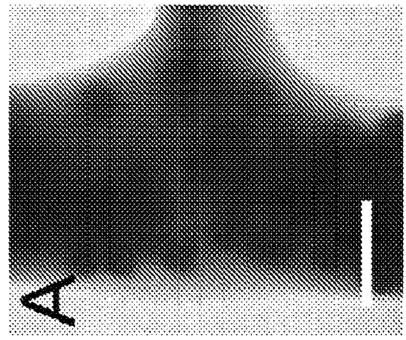

At 31° C., the semi-crystalline PEG in blow spun PLGA/PEG fibers melts, yielding a morphological change from fibers to a soft, homogenous film. At body temperature, fibers sprayed directly onto tissue transition to a conformal film, increasing surface coverage and eliminating large voids adjacent to the interface. Prior to the fiber to film transition, the spherical particles in the composite sealants are distributed throughout the fibers (see transmission electron microscopy, (FIG. 7, Panel 3A) and can create surface roughness generally proportional to the radius of the particles (FIG. 7, Panel B).

Figure 8:
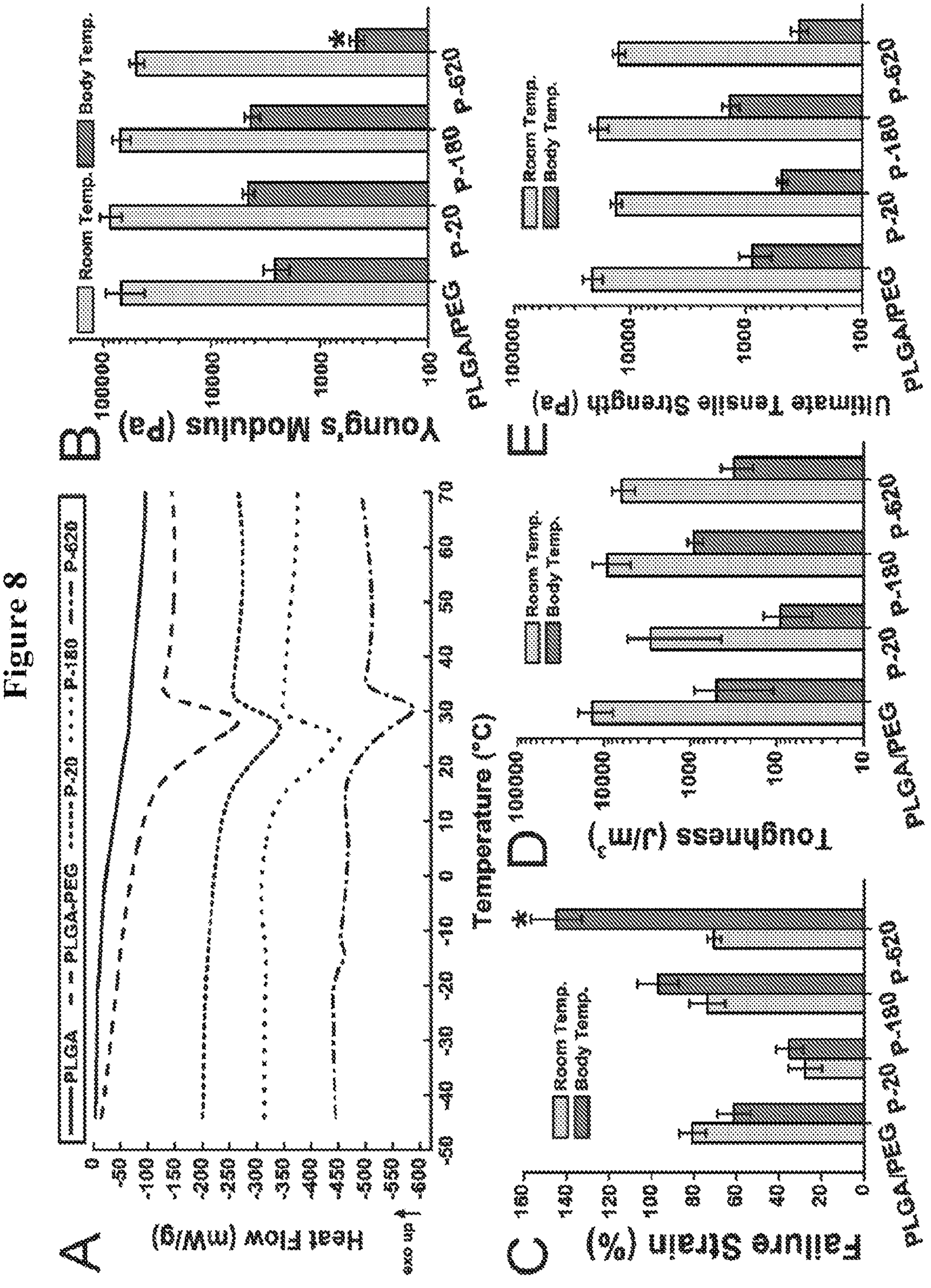
FIG. 8, Panel A, shows modulated differential scanning calorimetry (MDSC) of sealants. Curves have been shifted vertically for clarity. Data is shown graphically for: (Panel B) Young's modulus; (Panel C) failure strain in tensile testing; (Panel D) toughness; and (Panel E) ultimate tensile strength in tensile testing at room temperature and body temperature (37° C.). Composite surgical sealants are denoted "P-X", where "X" is the diameter (nm) of the silica particles incorporated into PLGA/PEG. All polymer composites containing silica particles had body-temperature mediated thermal transitions, but mechanical properties varied depending on particle size. Composite sealants containing the largest particles tested (P-620) had reduced Young's modulus and increased failure strain, indicating improved flexibility and crack suppression. Asterisks indicate statistically significant differences ($p<0.01$) between the indicated group and all other groups.

The temperature-dependent morphological transition of PLGA/PEG is characterized by an endotherm at 31° C. corresponding to the melting of PEG on its first heating cycle, after which the sealant shows a single glass transition temperature ($T_g$) indicating homogenization of the blend and miscibility of PLGA and PEG (FIG. 8, Panel A). Modulated differential scanning calorimetry (MDSC) was used to scan the composite fiber mats for this behavior, with no premelt cycle. The melting endotherm of PEG is observed in all polymer composites, but $T_m$ is slightly depressed. 20 nm silica particles increased the $T_g$ of P-20, while P-620's $T_g$ was unaffected. Silica particles also increase the amount of time it takes for the sealant to transition when heated in 37° C. air (Table 3).

Figure 9:
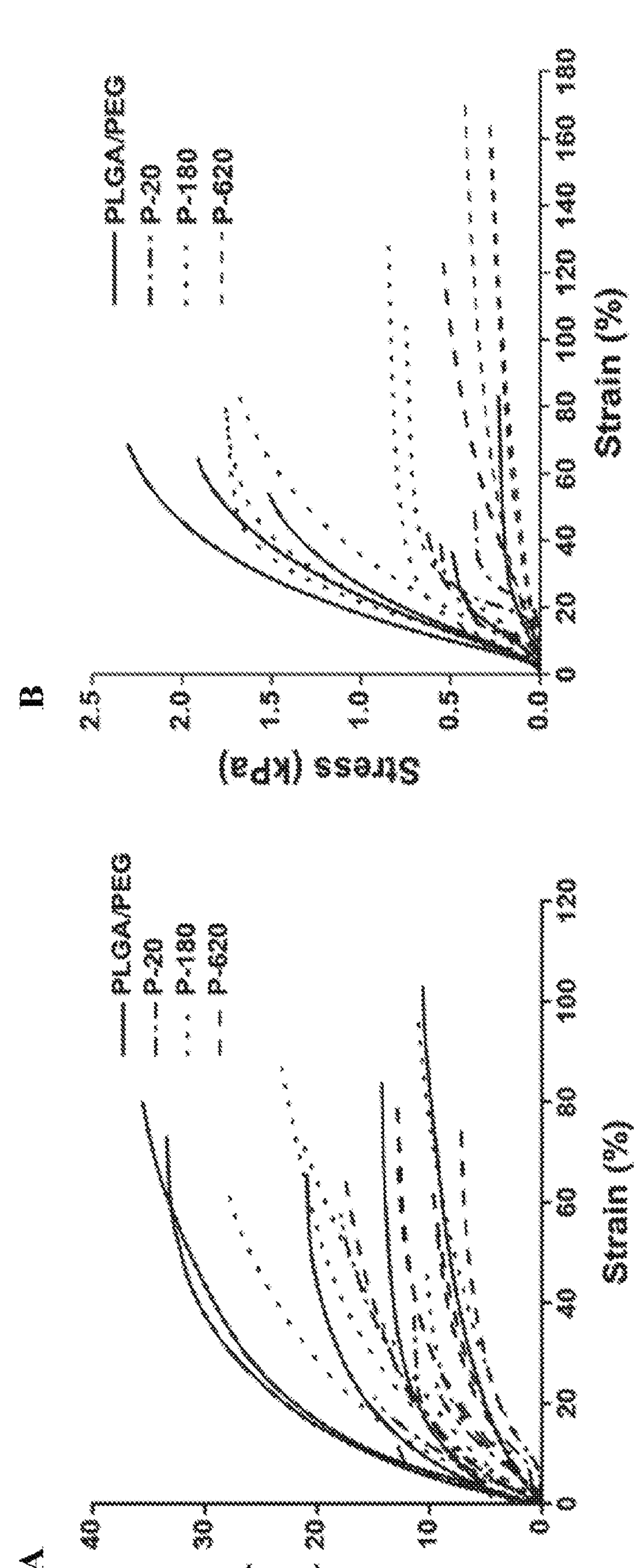
FIG. 9 illustrates data results for tensile testing stress-strain curves at: (Panel A) room temperature; and (Panel B) body temperature (37° C.).

It has recently been demonstrated that increased toughness, elasticity, and extensibility improve surgical sealant performance (A. Assmann et al. (2017) *A highly adhesive and naturally derived sealant*, Biomaterials 140:115-127; N. Annabi et al. (2017) *Engineering a sprayable and elastic hydrogel adhesive with antimicrobial properties for wound healing*, Biomaterials 139:229-243). Tensile mechanical testing was conducted at room temperature and body temperature (37° C.) (FIG. 8, Panel B, and FIG. 9, Panels A-B) on a DMA Q800 (TA Instruments). Depending on the size of the particles used in the composite sealants, stiffness and failure strain could be increased or decreased (FIG. 8, Panels B-C). The smaller particles in P-20 produced stiffer materials that failed at lower strains, consistent with the increased $T_g$ observed in MDSC analysis. Incorporating larger particles produced the opposite effect: P-620 had significantly lower modulus and greater failure strain.

Figure 10:
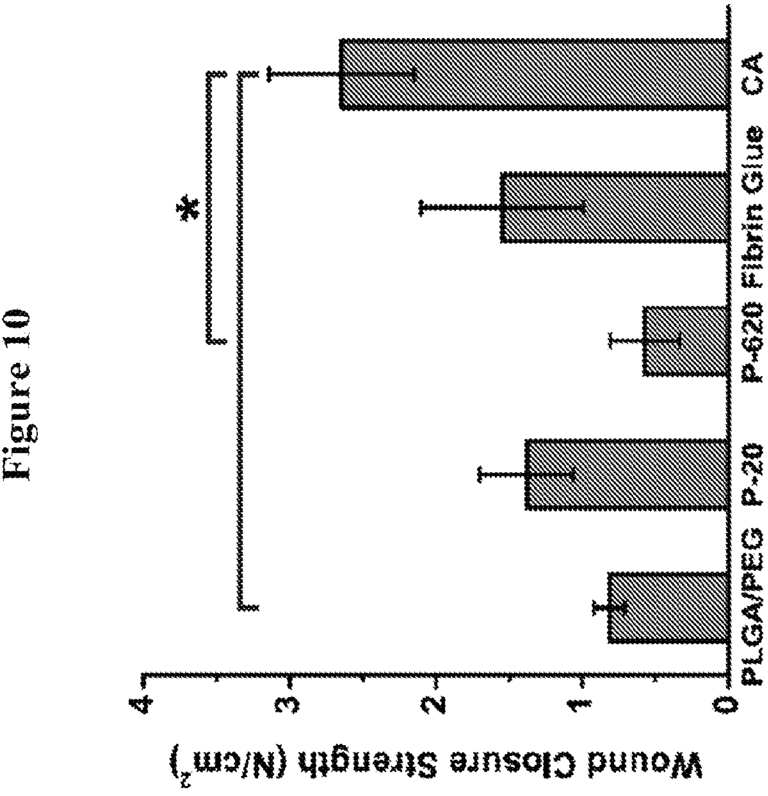
FIG. 10 illustrates graphically wound closure strength for PLGA/PEG, P-20, P-620, fibrin glue, and cyanoacrylate (CA).

The larger particles in P-620 suppress its brittle failure, increasing its failure strain compared to PLGA/PEG. This is consistent with the toughening mechanisms proposed in the literature for polymer-particle composites (B. B. Johnsen et al. (2007) *Toughening mechanisms of nanoparticle-modified epoxy polymers*, Polymer 48(2):530-541). Stress is concentrated on the particles, suppressing crack formation and creating small regions of high strain where debonding of the polymer matrix from particles may occur (A. S. Argon et al. (2003) *Toughenability of polymers*, Polymer 44:6013-6032). Toughness (FIG. 8, Panel D) and ultimate tensile strength (FIG. 8, Panel E) were similar for all samples, indicating that the composite sealants were not compromised by the high loading of silica particles. In wound closure strength testing (FIG. 10), which is primarily influenced by the cohesive strength of the adhesive, the stiffer P-20 produces higher values. In general, polymers reinforced with rigid particles display reduced strength but increased toughness, due to suppressed crack propagation (J. Jordan et al. (2005) *Experimental trends in polymer nanocomposites—a review*, Materials Science and Engineering: A, 393:1-11).

Figure 11:
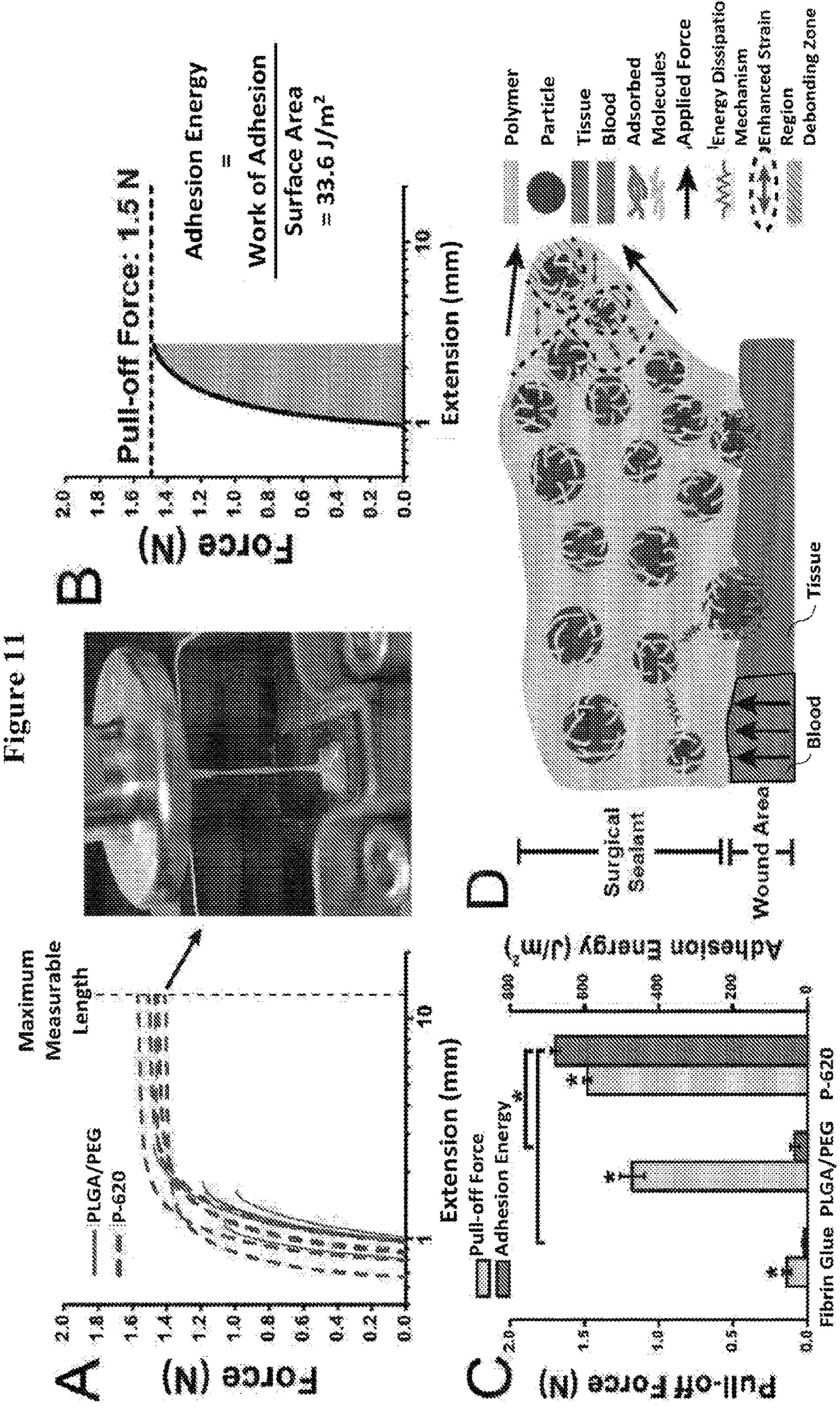
FIG. 11, Panel A, illustrates force-extension curves of pull-off adhesion testing. Inset: Image showing thread formation leading to cohesive failure of P-620. Panel B illustrates sample curve analyzed for pull-off force (peak force measured) and adhesion energy (integral of force curve, normalized for surface area at interface). Panel C shows pull-off adhesion force and adhesion energy for PLGA/PEG and P-620. Asterisks indicate statistically significant ($p<0.01$) differences. Panel D illustrates schematically the multiple toughening and adhesion enhancing mechanisms in particle-polymer composite sealants, including polymer chain adsorption to particles at the interface, suppressed crack propagation due to multiple regions of stress concentration, and energy dissipation as the reinforced sealant is deformed. Composite surgical sealants are denoted "P-X", where "X" is the diameter of the silica particles incorporated into PLGA/PEG. Composite sealants containing the largest particles tested (diameter of 620 nm) had increased adhesion force and energy compared to the non-composite control, PLGA/PEG. This was the result of adsorption of polymer chains to with particles at the interface and particle-composite toughening mechanisms.

Adhesion Energy and Strength Increase for Composite Sealants: Pull-off testing was performed at 37° C. on the DMA Q800 using collagen-coated compression clamps (FIG. 11, Panel A). Because the bulk of P-620 can be deformed to higher strains at lower force, the adhesive can dissipate energy through plastic deformation before adhesive failure (FIG. 11, Panels A-B). The combination of low stiffness and high failure strain directly translates to approximately 20 times greater adhesion energy (Figure, 11, Panel C). 4 of 5 PLGA/PEG samples failed at the interface, indicating that the bulk material's cohesive strength exceeds the strength of adhesive bonding, while none of the P-620 samples failed at the interface. Switching the failure mode from adhesive to cohesive is a critical feature of P-620 enabled simply by modulating particle size in the composite. This property was not present in P-20 because surface-area dependent confinement effects increase the $T_g$ of the PLGA/PEG matrix, making its extensibility lower than PLGA/PEG.

Pull-off adhesion force was also significantly enhanced by the silica particles, increasing by 25% (FIG. 11, Panel A). This can be attributed to particles at the interface increasing interfacial bonding energy (S. Rose et al. (2013) *Nanoparticle solutions as adhesives for gels and biological tissues*, Nature 505:382-385). However, these principles have only been applied to improving hydrogel adhesion to tissue (N.

Pandey et al. (2018) *Biodegradable Nanoparticles Enhanced Adhesiveness of Mussel-Like Hydrogels at Tissue Interface*, Adv Healthc Mater 7(7):e1701069). The approach investigated in the current work alternatively uses SBS to fabricate a solid adhesive polymer matrix with embedded particles. The polymer-particle composite design incorporates both micro- and nanoscale structures that increase the adhesive force and adhesion energy. Interfacial adhesion and bulk toughening mechanisms are illustrated in FIG. 11, Panel D, which shows the adsorption of molecules from both surfaces to the particles and the local regions of high deformation near the particles that allow for greater deformation. Just as silica microparticles in P-620 suppress crack formation in the bulk, enhancing its extensibility, the microparticles can also suppress cracks at the interface, creating a stronger adhesive bond. Crack suppression has been shown to improve interfacial adhesion by increasing fracture energy in hydrogel-based systems (H. Yuk et al. (2016) *Tough bonding of hydrogels to diverse non-porous surfaces*, Nature Materials 15(2):190-196; J. Li et al. (2017) *Tough adhesives for diverse wet surfaces*, Science 357:378-381).

Figure 12:
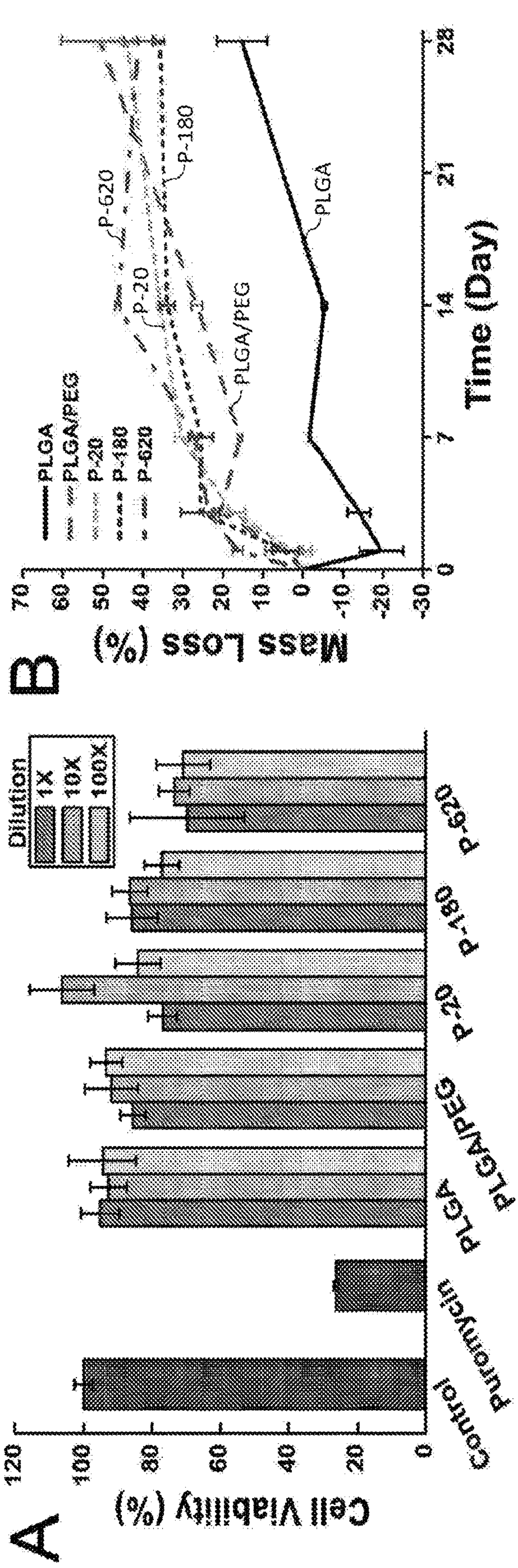
FIG. 12, Panel A, shows graphically cell viability of L929 fibroblasts exposed to simulated in vitro 24 h extractions from various polymer-particle composite sealants. Panel B shows mass loss from fiber mats incubated at 37° C. in phosphate buffered saline (PBS). Panel C shows coagulation time measured by time to form a mechanically stable clot in an inverted vial. Asterisk indicates statistically significant difference between indicated group and all other groups. Panels D, E, F and G show in vivo comparison of hemostatic efficacy in a porcine liver laceration model. Immediately after resection, the liver surface was sprayed with polymer blend surgical sealant without silica particles (PLGA/PEG, Panel D) and with 620 nm silica particles (P-620, Panel E). When PLGA/PEG was removed after 10 minutes, the resected area of the liver had not achieved hemostasis (Panel F). P-620 caused coagulation across the surface of the resection except for at a large hepatic vein (Panel G, arrow). Composite surgical sealants incorporating silica particles are denoted "P-X", where "X" is the diameter of the silica particles incorporated into PLGA/PEG. The composite sealants demonstrated acceptable cell viability, appropriate degradation rate, and enhanced hemostasis in vitro and in vivo.
Figure 12:
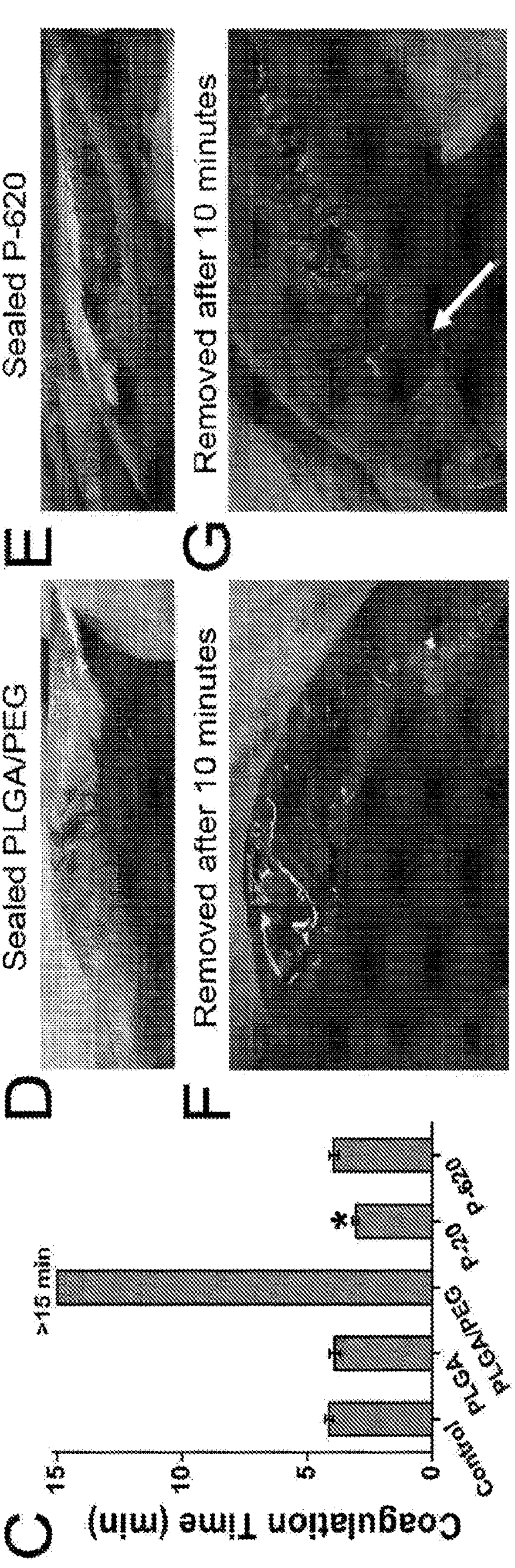

Assessing Biocompatibility of Composite Surgical Sealants: The controlled release of silica particles from the PLGA matrix limits their cytotoxicity compared to the administration of colloidal suspensions of these particles, which has been thoroughly investigated in the literature for silica particles of many sizes and types. Amorphous silica's cytotoxicity to murine epidermal cells is around 100 μg/mL when dispersed in cell culture media, but with a strong dependence on particle size: larger particles produce lower cytotoxicity, likely because they have different, slower cell uptake mechanisms (Kim, I. Y. et al. (2015) *Toxicity of silica nanoparticles depends on size, dose, and cell type, Nanomedicine: Nanotechnology*, Biology and Medicine 11:1407-1416). Amorphous silica particles also have known accumulation and excretion patterns (Fu, C. et al. (2013) *The absorption, distribution, excretion and toxicity of mesoporous silica nanoparticles in mice following different exposure routes*, Biomaterials 34:2565-2575). After 24 hours of exposure to extractions from P-20, P-180, and P-620, cell viability is only slightly limited when compared to PLGA and PLGA/PEG (FIG. 12, Panel A). This suggests that particles are eluted slowly into the media and that they contribute minimal cytotoxicity. Prior investigations of solution blow spinning biodegradable polymer fibers from acetone show that acetone has no negative effect on cell viability (Behrens, A. M. et al., (2015) *Biodegradable-polymer-blend-based surgical sealant with body-temperature-mediated adhesion*, Adv. Mater. 27:8056-8061; A. M. Behrens et al. (2014) *In Situ Deposition of PLGA Nanofibers via Solution Blow Spinning*, ACS Macro Lett 3(3):249-254).

To verify that degradation of the sealants occurs complementary to the timeline for adequate wound healing and is not affected by particulate components, a study of mass loss during degradation was conducted by incubating fiber mats in PBS at 37° C. PLGA/PEG fiber mats typically maintain mechanical integrity for about 28 days, allowing for support throughout the wound healing process, but lose a substantial amount of mass in the first few days as highly water-soluble PEG is released from the polymer matrix (FIG. 12, Panel B). The tested particle composite fiber mats showed a similar degradation profile. After the initial burst release of PEG, there is a slow, constant release of material from the solid polymer matrix.

Silica Decreases Coagulation Time and Improves Hemostasis In vivo: Achieving hemostasis is critical to avoiding surgical complications. We preliminarily assessed the hemostatic effects of PLGA/PEG composite fiber mats using a clotting time test (FIG. 12, Panel C). PLGA/PEG fiber mats inhibit clot formation, likely due to the high amount of PEG composing the fibers, which can interfere with critical enzymatic reactions in the coagulation cascade. Silica, which has a high negative surface charge and is a known hemostatic due to the glass effect (Ostomel, T. A. et al. (2007) *Metal Oxide Surface Charge Mediated Hemostasis*, Langmuir 23:11233-11238), decreases the clotting time compared to PLGA/PEG in all cases. P-180 and P-620 return clotting time to control levels, while P-20 significantly decreases clotting time by approximately 25%. These results show that incorporating silica into PLGA/PEG has additional utility in promoting hemostasis, which will allow the composite sealants to be used in surgical procedures with high amounts of potential blood loss.

To simulate the use of PLGA/PEG and P-620 as hemostats in vivo, we sprayed the sealants directly onto a bleeding porcine liver immediately after resection. This approach models a procedure such as liver resection, which has increased morbidity due to the risk of significant blood loss (Meyers, R. L. et al., Liver Tumors, in: Liver Tumors, 7th ed., Lippincott Williams & Wilkins, 2015). Immediately after deposition, PLGA/PEG showed blood permeating the sealant (FIG. 12, Panel D) while P-620 maintained a seal (FIG. 12, Panel E). When the sealants were removed after 10 minutes, the surface of the liver coated with PLGA/PEG had not achieved hemostasis (FIG. 12, Panel F), while the surface coated with P-620 had stopped bleeding except for a large vessel (FIG. 12, Panel G, arrow). Incorporating silica improves the hemostatic efficacy of the PLGA/PEG polymer blend.

Figure 13:
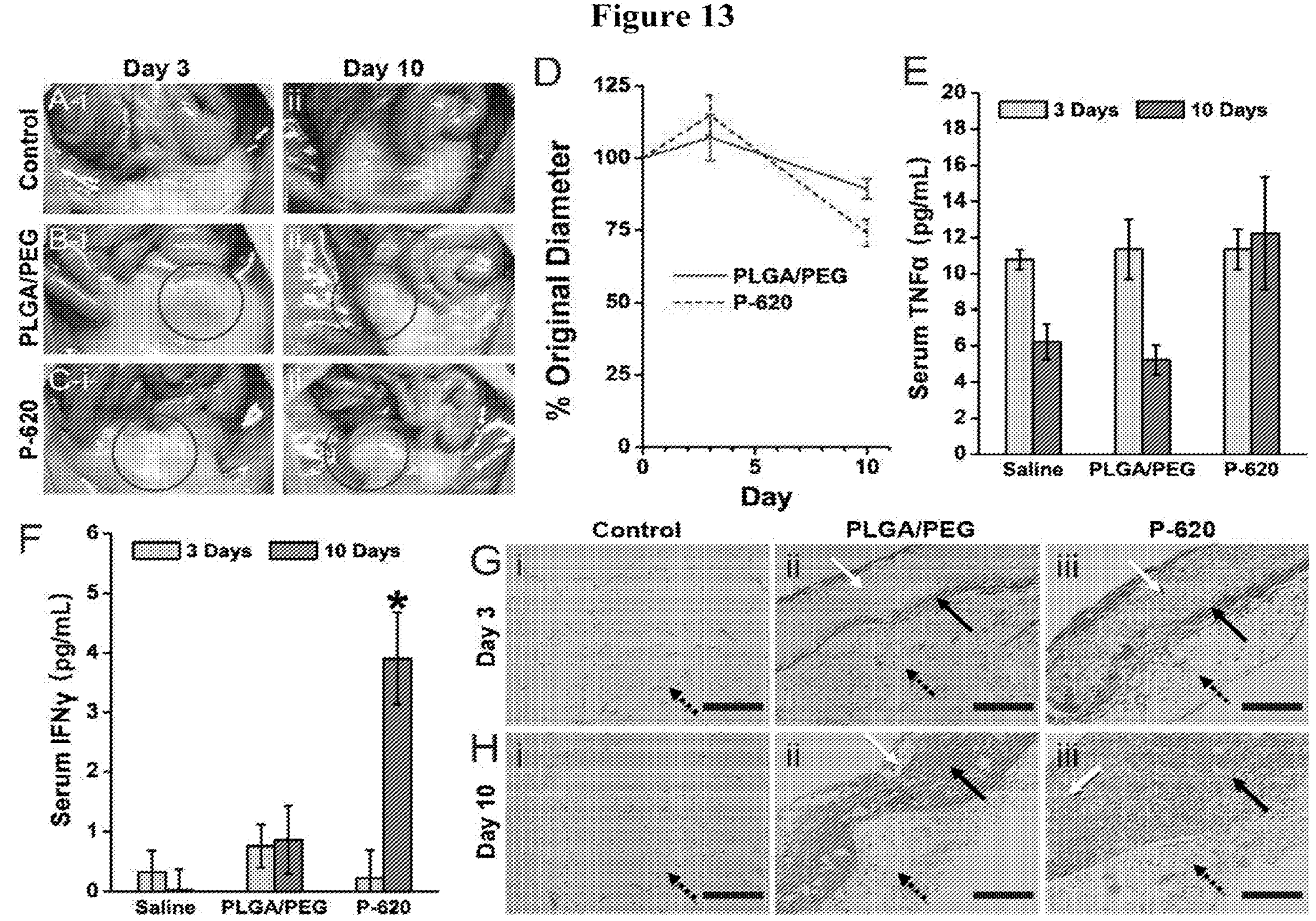
FIG. 13, Panels A, B and C, are images of the implant site showing minimal gross inflammation at 3 days (i) and 10 days (ii) for a control saline injection (Panel A), PLGA/PEG (Panel B), and P-620 (Panel C). As shown, polymer blend composite surgical sealants produced a mild inflammatory response. The composite sealant containing 620 nm silica particles (P-620) was tested against PLGA/PEG by intraperitoneal implantation. The implanted disks of surgical sealant were engulfed by the abdominal fat pads (circled). Both disks decrease in diameter over 10 days by approximately 25% (Panel D). Serum concentrations of TNFα (Panel E) and INFγ (Panel F) are roughly equivalent, except for the increased concentration of 10-day INFγ. Sections of the abdominal fat pads adjacent to the implantation site were stained with hematoxylin and eosin (Panels G and H). Scale bars=400 m. Black dash line arrows point to the abdominal fat pads, white arrows point to the sealant disk, and black solid line arrows point to areas of cellular infiltration into the surgical sealant disks.

Composite Sealants Produce Minimal Additional Inflammation: To further demonstrate the biocompatibility of the PLGA-silica composite surgical sealants, biodegradation and the potential immune response was assessed in a mouse intraperitoneal implantation model. Composite sealants were implanted to determine if incorporating silica within a polymer matrix affects biodegradation, local inflammation, or systemic immune response. PLGA/PEG and P-620 sealant samples were fabricated into 5 mm diameter disks that were implanted into the right lower quadrant of the abdomen. After implantation, the implanted sealant disk became attached to the abdominal fat pads (5 of 6 PLGA/PEG implants, 6 of 6 P-620 implants). There was no gross inflammation observed, and the peritoneum appeared normal, similar to that of the control group that received a saline injection (FIG. 13, Panel A). After 3 days, the sealant was engulfed within the fat pads (FIG. 13, Panels B-C). Despite swelling moderately at 3 days, the size of the sealant disks ultimately decreased over the duration of the 10-day implantation (FIG. 13, Panel D), matching well with the mass loss rate in vitro (FIG. 12, Panel B). All mice survived to the experimental endpoints without any signs of illness or distress.

Recent studies have shown that biomaterials implanted in the intraperitoneal space adhere to the abdominal fat pads, where they can be fibrosed and create the potential for an immune response (Doloff, J. C. et al. (2017) *Colony stimulating factor*-1 *receptor is a central component of the foreign body response to biomaterial implants in rodents and non-human primates*, Nature Materials 16(6):671-680). Therefore, we measured the serum levels of two cytokines, tumor necrosis factor alpha (TNFα) and interferon gamma (INFγ), that are increased during acute inflammation and macrophage activation. There were no significant differences in TNFα levels over time or between PLGA/PEG and P-620 (FIG. 13, Panel E), indicating that there was minimal systemic inflammation. INFγ levels, however, increased significantly at day 10 for P-620 (FIG. 13, Panel F), indicating that the silica particles may have caused macrophage activation, but serum levels of INFγ are still low compared to levels for an acute inflammatory response, which can be higher than 100 pg $mL^{-1}$ (Mottas, I. et al. (2019) *Amphiphilic nanoparticle delivery enhances the anticancer efficacy of a TLR7 ligand via local immune activation*, Biomaterials 190-191, 111-120). While the abdominal fat pads generally show minimal collagen content, a thin layer of fibrosis and inflammatory cell infiltration (black arrows) was observed at the interface with the surgical sealant (white arrows) for both PLGA/PEG and P-620 after 3 days (FIG. 13, Panel G). After 10 days, there is additional collagen deposition and cell infiltration throughout the surgical sealant (FIG. 7H). Ongoing fibrosis at the interface of P-620 with the fat pad corroborates the increased 10-day INFγ serum levels.

Based on these results, incorporating silica into PLGA-PEG creates a more persistent local inflammatory response. However, the lack of overt signs of inflammation in the intraperitoneal cavity, such as erythema, edema, and adhesion development, indicate that the level of acute inflammation is small for both sealants and localized to just the tissue-sealant interface, with low systemic effect. Overall, PLGA/PEG and P-620 produce minimal additional acute inflammation in the intraperitoneal space, where they are expected to be used.

DISCUSSION

Surgical sealants are typically deposited as viscous fluids and form crosslinked matrices after curing. Fibrin glue, which has excellent biocompatibility, achieves this by enzymatic crosslinking of a biologically-derived precursor solution. However, attempts to increase adhesion based on crosslinking and covalent bonding to tissue have resulted in increased cytotoxicity or inflammation by exposing the surgical site to reactive functional groups. Thus, even when strategies are developed to improve the adhesion of this type of surgical sealant, they may still have low biocompatibility, slow biodegradation, or poor ease of use (W. D. Spotnitz et al., Hemostats, sealants, and adhesives: components of the surgical toolbox, Transfusion, 48 (2008) 1502-1516). In addition, misapplication of flowable sealant precursors due to poor ease of use creates the potential for large sealant droplets to be deposited into the vasculature, which leads commercially available surgical sealants such as fibrin glue to be contraindicated for application into highly vascularized tissue or onto heavy arterial or venous bleeding. The PLGA/PEG/silica surgical sealants disclosed herein invert this paradigm, depositing an initially stiff matrix of composite fibers that soften and become adhesive upon heating to body temperature. Unlike conventional curable surgical sealants, the PLGA/PEG/silica composite sealants adhere only to the target site where the solid fiber mat is initially sprayed.

The polymer-particle composite sealants incorporate both micro- and nanoscale structures that substantially increase the adhesive force. This is due to particles at the interface increasing interfacial bonding energy (Rose, S. et al. (2013) *Nanoparticle solutions as adhesives for gels and biological tissues*, Nature 505:382-385; Bait, N. et al. (2011) *Hydrogel nanocomposites as pressure-sensitive adhesives for skin-contact applications*, Soft Matter 7:2025; Okada, M. et al. (2017) *Biocompatible nanostructured solid adhesives for biological soft tissues*, Acta Biomater. 57:404-413). However, these principles have only been applied to improving hydrogel adhesion to tissue (Pandey, N. et al. (2017) *Biodegradable nanoparticles enhanced adhesiveness of mussel-like hydrogels at tissue interface*, Adv. Healthc. Mater. 7(7):e1701069). The disclosed methodologies alternatively use SBS to fabricate a solid adhesive polymer matrix with embedded particles. Just as silica microparticles in P-620 suppress crack formation in the bulk, enhancing its extensibility (FIG. 8, Panel C) and adhesion energy, the microparticles can also suppress cracks at the interface, creating a stronger adhesive bond (FIG. 12, Panel A). Crack suppression has been shown to improve interfacial adhesion by increasing fracture energy in hydrogel-based systems (H. Yuk et al. (2016) *Tough bonding of hydrogels to diverse non-porous surfaces*, Nature Materials 15(2):190-196; J. Li et al. (2017) *Tough adhesives for diverse wet surfaces*, Science 357:378-381).

Despite the turbulent nature of the SBS process, incorporating particles into the blow spinning solution creates sealants with a consistent nanoscale texture that is visible on the surface of fibers (FIG. 2, Panel E and FIG. 7, Panels A-B). Using silica produces composite fibers with much higher loading of particles compared to previous research on blow spun composites (Vural, M. et al. (2018) *Spray-Processed Composites with High Conductivity and Elasticity*, ACS Appl. Mater. Interfaces, 10(16):13953-13962). Such surface nanoarchitectures have been discovered to contribute significantly to the adhesive footpads of small animals, such as the gecko (Huber, G. et al. (2005) *Evidence for capillarity contributions to gecko adhesion from single spatula nanomechanical measurements*, PNAS 102:16293-16296). This knowledge then inspired the design of micropatterned adhesive materials (Geim, A. K. et al. (2003) *Microfabricated adhesive mimicking gecko foot-hair*, Nat Mater 2:461-463). However, the majority of conventional adhesive nanostructured polymer surfaces in the art have been fabricated using etched or patterned templates and 3D direct laser writing (Greiner, C. et al. (2009) *Hierarchical Gecko-Like Adhesives*, Adv. Mater 21:479-482; Röhrig, M. et al. (2012) *3D Direct Laser Writing of Nano—and Micro-structured Hierarchical Gecko-Mimicking Surfaces*, Small 8:3009-3015). Fabricating the adhesive sealant using SBS yields conformal materials with site-specific sizing adaptable to any tissue defect, an advantage over prefabricated nanostructured adhesives.

This simple composite approach yields a solid, biodegradable, and fully synthetic surgical sealant with enhanced adhesion in burst pressure (FIG. 2, Panel B) and pull-off adhesion (FIG. 11, Panel A) tests. Swelling is much lower than in synthetic hydrogel sealants such as Coseal (FIG. 13, Panel D), similar to low-swelling or negative-swelling tissue adhesives (Henise, J. et al. (2016) *Surgical sealants with tunable swelling, burst pressures, and biodegradation rates*, J. Biomed. Mater. Res. B Appl. Biomater. 105:1602-1611; Barrett, D. G. et al. (2013) *Mechanically robust, negatives welling, mussel-inspired tissue adhesives*, Adv. Healthc. Mater. 2:745-755). Burst pressure in our ex vivo model is significantly greater than the clinical standard, fibrin glue, and comparable to cyanoacrylate (FIG. 2, Panel B). P-620, at 160±30 mmHg, produces in vitro burst pressures comparable to dual-network tissue adhesives (roughly 200 mmHg; H. Yuk et al. (2016) *Tough bonding of hydrogels to diverse non-porous surfaces*, Nature Materials 15(2):190-196) and photopolymerized gelatin sealants (~100 mmHg; Vuocolo, T. et al. (2012) *A Highly elastic and adhesive gelatin tissue sealant for gastrointestinal surgery and colon anastomosis*, J. Gastrointest. Surg. 16:744-752) in similar models on ex vivo tissue. Interestingly, PLGA/PEG/silica sealants at body temperature (E ~1-10 kPa, FIG. 8, Panel B) have a lower Young's modulus than other tissue adhesives, which typically have E>25 kPa (Vakalopoulos, K. A. et al. (2015) *Mechanical strength and rheological properties of tissue adhesives with regard to colorectal anastomosis: an ex vivo study*, Ann. Surg. 261:323-331). This allows them to be deformed and move with the soft tissues being sealed.

Nanostructured adhesives use nanoscale topography to increase the surface area at the interface, and therefore force of adhesion. Nanoparticles increase adhesion forces between tissue samples treated with silica nanoparticle suspensions due to adsorption (S. Rose et al. (2013) *Nanoparticle solutions as adhesives for gels and biological tissues*, Nature 505:382-385) and increased physical bonding, either through a composite structure or secondary network (N. Bait et al. (2011) *Hydrogel nanocomposites as pressure-sensitive adhesives for skin-contact applications*, Soft Matter 7:2025-2032; M. Okada et al. (2017) *Biocompatible nanostructured solid adhesives for biological soft tissues*, Acta Biomaterialia, 57:404-413). Tuning of silica particle size can produce increased flexibility, due to crack suppression by larger, micron-sized particles (FIG. 8, Panel B) or faster blood coagulation (FIG. 12, Panels C-G) when using 20 nm silica.

Silica particles decrease coagulation time of PLGA/PEG, a critical feature that allows PLGA/PEG/silica composites to be deployed for hemostasis (FIG. 12, Panels D-H). For nuisance bleeding and other surgical procedures where noncovalent polymer adhesion and occlusion would be sufficient, it may be used instead of delivering prohemostatic coagulation factors. Silica particles trigger hemostasis through their high surface charge and physical adsorption (Manas, D. M. et al. (2016) *Expert opinion on advanced techniques for hemostasis in liver surgery*, Eur. J. Surg. Oncol. 42:1597-1607; Pourshahrestani, S. et al. (2019) *Well-ordered mesoporous silica and bioactive glasses: promise for improved hemostasis*, Biomater. Sci. 7:31-50). The combination of occlusion and hemostasis provided by PLGA/PEG/silica is an alternative to modern biologically derived or recombinant hemostats, which deliver fibrinogen supplemented with combinations of thrombin and/or Factor XIII to specifically target exposed extracellular matrix and create or crosslink a fibrin clot (Calcaterra, J. et al. (2013) *Recombinant human fibrinogen that produces thick fibrin fibers with increased wound adhesion and clot density*, Biomacromolecules 14:169-178; Carlson, M. A. et al. (2014) *A totally recombinant human fibrin sealant*, J. Surg. Res. 187:334-342). Synthetic polymers that bind fibrin are also capable of targeting a wound site in this manner to promote hemostasis (Chan, L. W. et al. (2015) *A synthetic fibrin cross-linking polymer for modulating clot properties and inducing hemostasis*, Sci. Transl. Med. 7:277ra29).

PLGA/PEG/silica produces low levels of inflammation, only slightly increasing macrophage activation (FIG. 13, Panel F) and cell infiltration (FIG. 13, Panels G-H) without producing any difference in gross inflammation of the IP space (FIG. 13, Panels A-C). For use as a surgical sealant, long-term studies in large animal models are necessary to demonstrate a reduction in the observed complication rate associated with soft tissue wound closure, either due to prevention of blood loss or leak. While the purpose of a surgical sealant is to occlude, for use in the clinic it should demonstrate efficacy in reducing complication rate, a holistic metric that encompasses leakage, abscess formation, other adverse events that may cause a re-operation, septic shock, or death (G. Silecchia et al. (2008) *The use of fibrin sealant to prevent major complications following laparoscopic gastric bypass: results of a multicenter, randomized trial*, Surgical Endoscopy, 22:2492-2497).

PLGA/PEG/silica composite surgical sealants are uniquely suitable for translation into the clinic because the system is composed of widely-used fully synthetic and biodegradable materials. The present disclosure demonstrates that polymer-particle composite surgical sealants offer increased adhesion and intestinal burst pressure compared to pure polymer blend sealants. Other properties, such as stiffness, failure strain, and $T_g$ are affected by particle size. 620 nm silica particles provide a number of advantages over other particle sizes and the non-composite control, maximizing burst pressure and adhesion energy. Ultimately, the incorporation of silica particles into PLGA/PEG increased tissue adhesion by providing a nanostructured contact area and increasing energy dissipation. These benefits are the result of enhanced interfacial interactions facilitated by the particles, a change in adhesive failure mode from adhesive to cohesive failure, and composite toughening mechanisms, especially crack suppression. Biodegradation, cytotoxicity, and inflammation are minimally affected by the incorporation of particles, and these sealants are deliverable directly to the site of surgery as fiber mats using solution blow spinning.

Example 2

Pressure-Sensitive Tissue Adhesives (Pstas) Comprising Blends of Poly(Lactide-Co-Caprolactone) (PLCL) and Poly (Lactide-Co-Glycolide) (PLGA)

Materials and Methods

Figure 14:
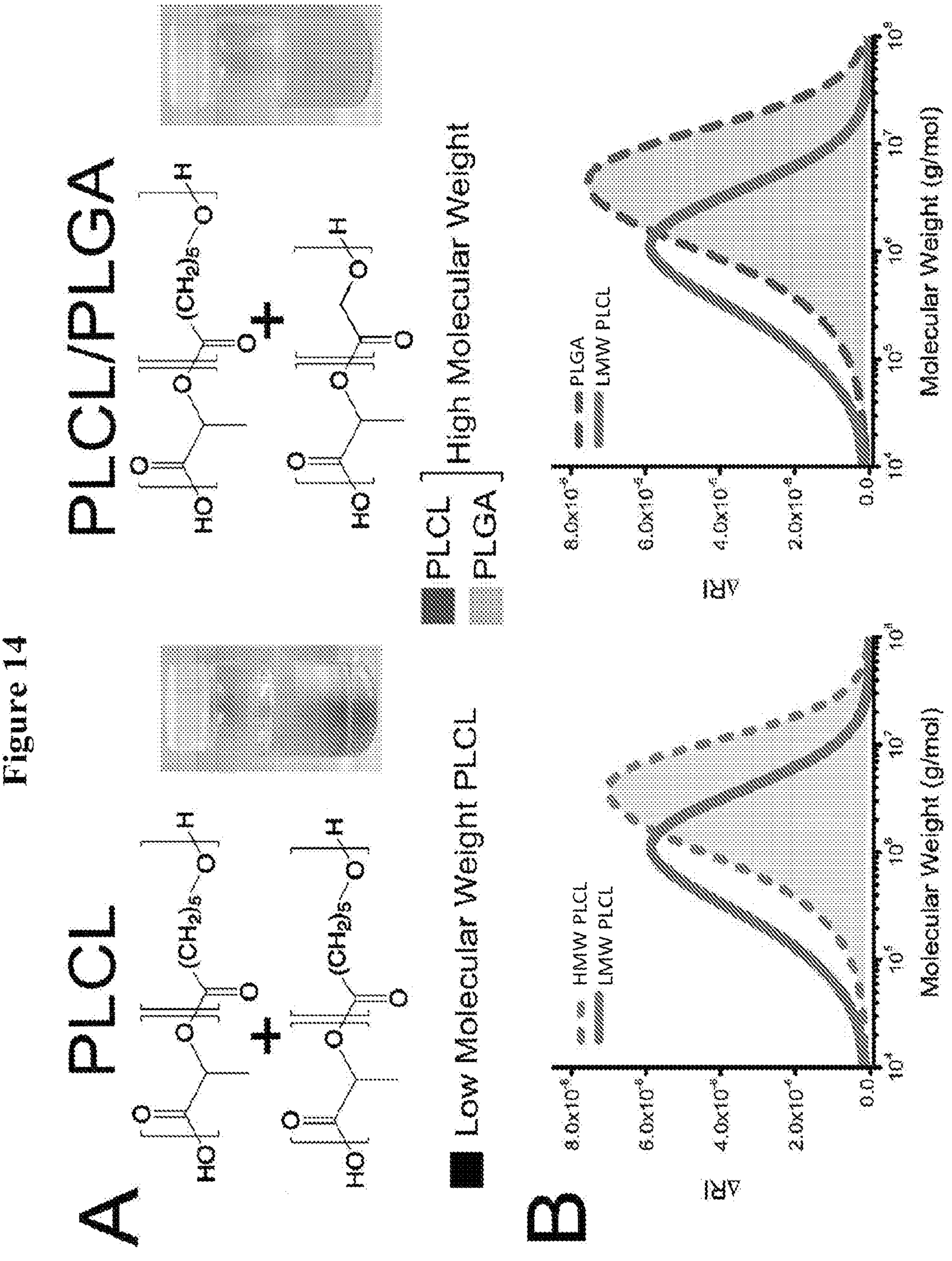
FIG. 14, illustrates schematically components (Panels A-B) and gel permeation chromatography (Panel C) of the tissue adhesive polymer blends. Panel D illustrates Schematically sprayable pressure sensitive tissue adhesive (PSTA) deposition. Panel E shows atomic force microscopy of the PSTA.
Figure 14:
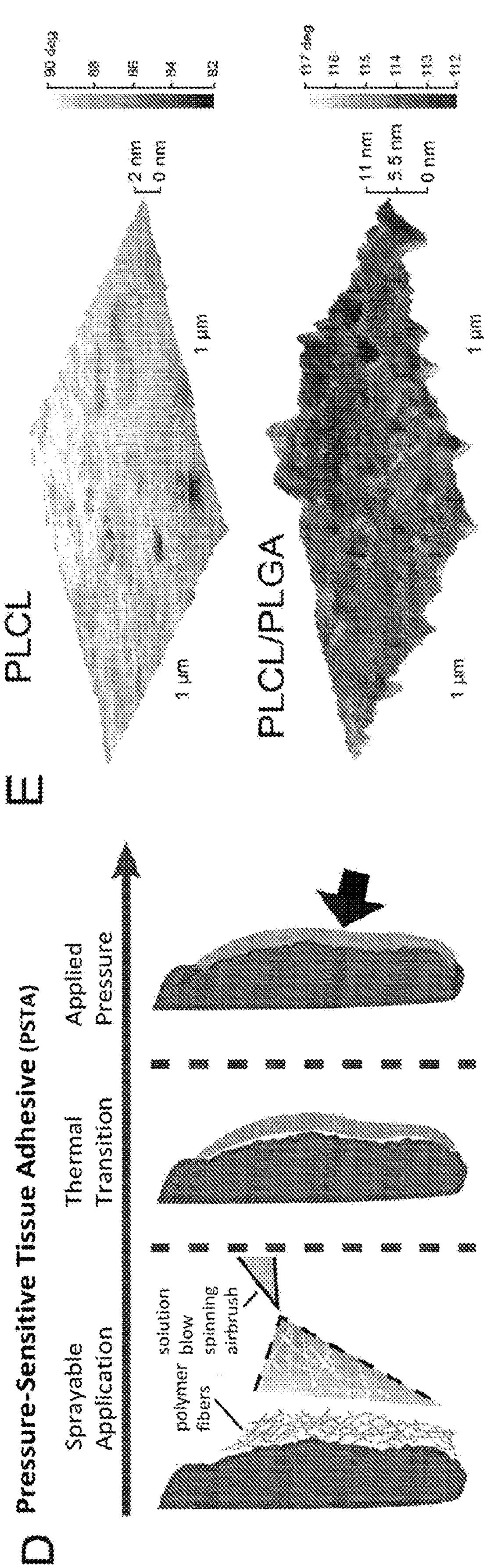

Pressure-sensitive tissue adhesives (PSTA) were developed comprising blends of low and height molecular weight polymers. In disclosed embodiments, composite sealants comprise a blend of poly(lactide-co-caprolactone) (PLCL), a biodegradable elastomer (Jeong, S. I. et al. (2004) *Manufacture of Elastic Biodegradable PLCL Scaffolds for Mechano-Active Vascular Tissue Engineering*, J. Biomater. Sci. Polym. Ed. 15(5):645-660), and poly(lactide-co-glycolide) (PLGA), which was used to increase stiffness (FIG. 14, Panel A). Distinct low molecular weight (LMW) and high molecular weight (HMW) distributions of PLCL (see gel permeation chromatography (GPC), FIG. 14, Panels B-C) were used to modulate viscoelasticity. As demonstrated, the rheological properties of the blends, especially their creep compliance and tan(δ), have a profound effect on their surface wettability and subsequently, their tissue adhesion. The PSTA capitalizes on advances in the synthesis and processing of biodegradable elastomers, such as optimized random copolymer ratios (Mir, M. et al., (2017) *Recent Applications of PLGA Based Nanostructures in Drug Delivery*, Colloids Surf. B Biointerfaces 159:217-231; Jeong, S. I. et al. (2004) *In vivo Biocompatibilty and Degradation Behavior of Elastic Poly(l-Lactide-Co-ε-Caprolactone) Scaffolds*, Biomaterials 25(28):5939-5946) and polymer blends with modified thermal properties and degradation rates (Saini, P. et al. (2016) *Poly(Lactic Acid) Blends in Biomedical Applications*, Adv. Drug Deliv. Rev. 107:47-59; Lao, L. L. et al. (2008) *Modeling of Drug Release from Biodegradable Polymer Blends*, Eur. J. Pharm. Biopharm. 70(3):796-803; Li, T. et al. (2016) *Toughening Glassy Poly (Lactide) with Block Copolymer Micelles*, ACS Macro Lett. 5(3):359-364; Imre, B. and Pukánszky, B. (2013) *Compatibilization in Bio-Based and Biodegradable Polymer Blends*, Eur. Polym. J. 49(6):1215-1233; Behrens, A. M. et al. (2015) *Biodegradable-Polymer-Blend-Based Surgical Sealant with Body-Temperature-Mediated Adhesion*, Adv. Mater. 27(48): 8056-8061; Behrens, A. M. et al. (2016) *Rapid Fabrication of Poly(DL-Lactide) Nanofiber Scaffolds with Tunable Degradation for Tissue Engineering Applications by Air-Brushing*, Biomed. Mater. 11(3):035001).

The components of the PSTA are dissolvable in acetone to yield a sprayable polymer solution (FIG. 14, Panel A, inset). The polymer solution comprises 20% w/v polymer (including both LMW and HMW polymer), which is dissolved in acetone (e.g., 200 mg of polymer per mL of acetone, with LMW PLCL 14% w/v and HMW 6% w/v in the acetone solution). Various Blends of LMW PLCL and HMW PLCL, as well as blends of LMW PLCL with PLGA, were investigated. Sprayability allows the PSTA to be deposited directly to the surgical site as fibers using a solution blow spinning airbrush (FIG. 14, Panel D) (Daristotle, J. L. et al. (2016) *A Review of the Fundamental Principles and Applications of Solution Blow Spinning*, ACS Appl. Mater. Interfaces 8(51):34951-34963). It then forms a thin film on tissue after softening (film shown in atomic force microscopy, FIG. 14, Panel E). Tissue adhesion, degradation, and mechanical properties were characterized to determine which polymer blends exhibited the strongest pressure sensitive adhesion. Depending on whether HMW PLCL or PLGA was incorporated, the PSTA could be tuned to degrade at different speeds and with varying amounts of erosion, which in turn produced differences in intraperitoneal space adhesiogenicity and immune response.

Figure 15:
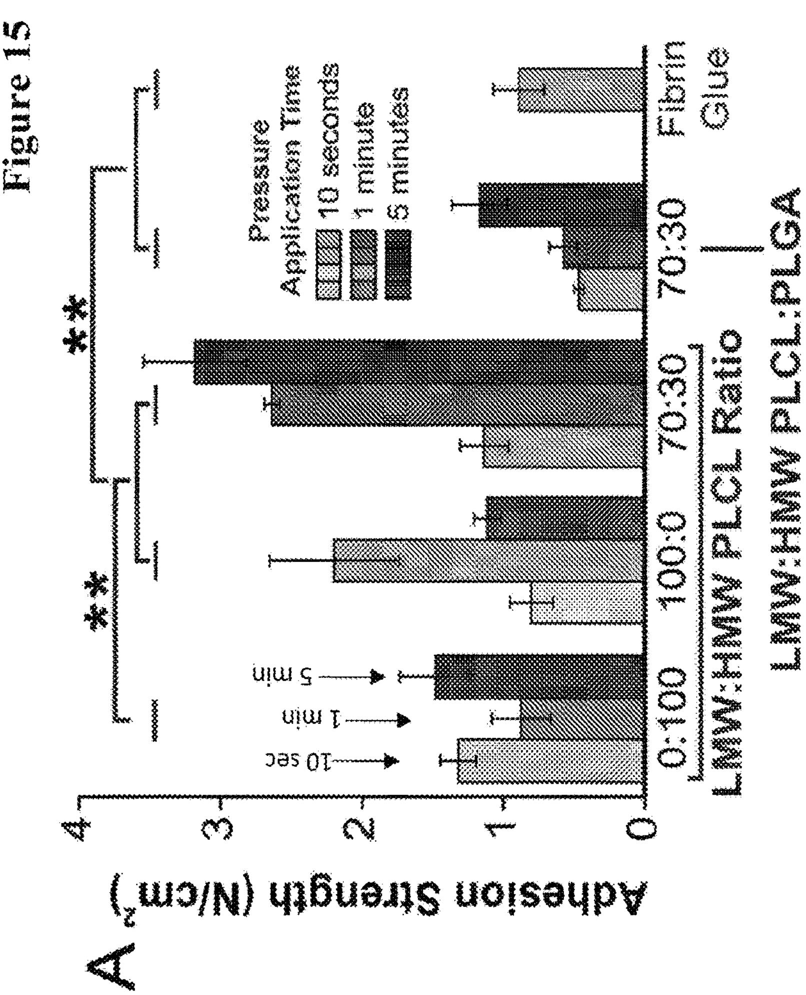
FIG. 15, Panel A shows cardiac-patch-to-cardiac-tissue adhesion strength of various blends of poly(lactide-co-caprolactone) (PLCL) and poly(lactide-co-glycolide) (PLGA) at pressure application time at 10 seconds (first bar for each blend), 1 minute (second bar for each blend), and 5 minutes (third bar for each blend), and fibrin glue. Panel B shows adhesion strength over time for pressure sensitive polymer blends, showing the continued increase in adhesion in when a blend of LMW and HMW polymers are used. Panel C shows graphically ex vivo burst pressure on intestine using only the adhesive as a sealant, with failure mode reported (Panel D). Panel E shows factor increase in adhesion strength or burst pressure, showing the difference in effect of PLCL and PLGA as HMW blend components.
Figure 15:
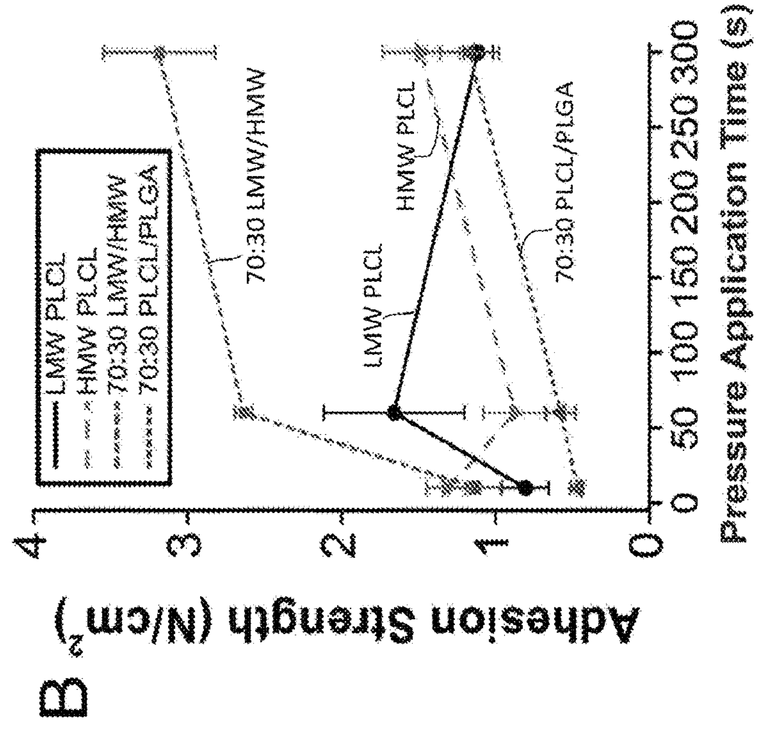
Figure 15:
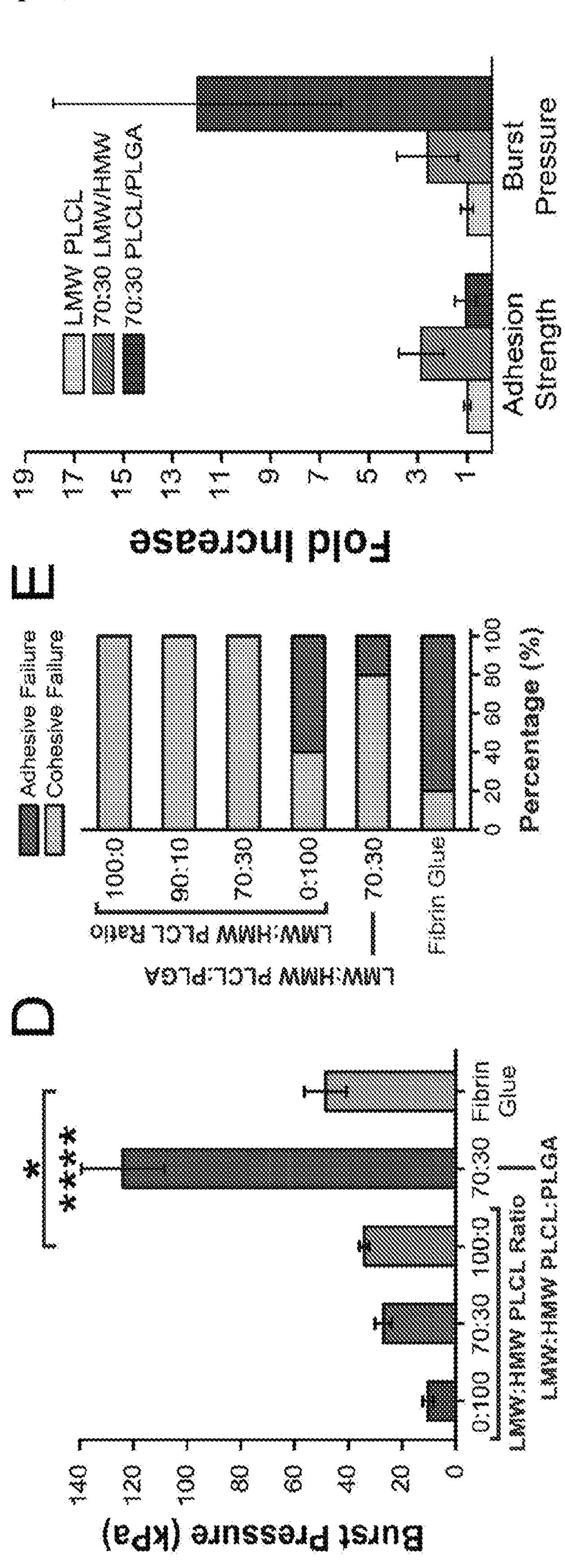

To investigate the PSTA's ability to form a strong adhesive bond, the PSTA was sprayed onto cardiac tissue and applied a poly(tetrafluoroethylene) cardiac patch with compressive force. Pressure-sensitivity of the PSTA was inferred from the effect that pressure application time had on adhesion strength (FIG. 15, Panel A). LMW PLCL has inherently high wettability and tack on wet tissue, producing a strong adhesive bond in seconds. To compare the effects of using HMW additives to create a PSTA blend with mechanical integrity, both HMW PLCL or PLGA were blended at a 70:30 ratio of LMW PLCL to HMW additive. 70:30 blends of LMW and HMW PLCL produce adhesive bonds that are stable, significantly increasing in strength after 5 minutes of applied pressure. FIG. 15, Panel B summarizes the short-term time course of adhesion for 4 blends of LMW and HMW PLCL, showing that for LMW PLCL alone the bond deteriorates within 5 minutes. Without HMW PLCL, adhesion peaks at 1 minute after application and then decreases.

The sealing strength of the polymer blends in wound closure was tested by measuring the burst pressure of a sealed partial incision ex vivo on segments of porcine intestine (FIG. 15, Panel C). As demonstrated, LMW PLCL supplemented with PLGA outperforms the PLCL LMW/HMW blends in this form of testing because of its high resistance to inflationary forces. The PLGA reinforces the system without sacrificing adhesion, preventing cohesive failure (FIG. 15, Panel D). This, in combination with the adhesion strength study (FIG. 15, Panel A), suggests that PLCL LMW/HMW PSTA would perform well as surgical glue given it is less likely to experience adhesive failure and has inherent tackiness. However, LMW PLCL reinforced with PLGA would make an excellent surgical sealant given it has adequate stiffness and strength to withstand inflation and deformation forces. Ultimately, the data demonstrated that the use of the disclosed PLCL and PLGA systems allows for the production of adhesive blends with a wide range of mechanical properties for various applications.

Figure 16:
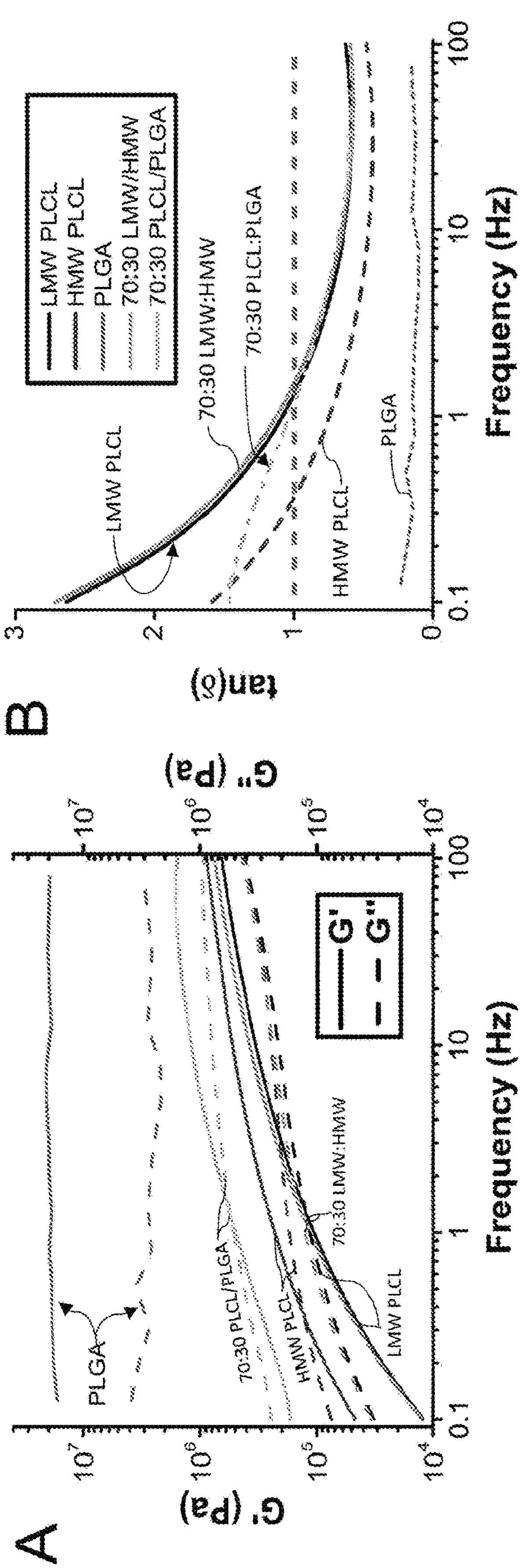
FIG. 16, Panels A and B, show shear rheology of polymer blends, showing the shift towards elastic, solid-like properties with HMW polymers. Storage (G') and loss (G") modulus (Panel A) across a frequency range encompassing long time scales relevant for pressure-sensitive bond formation (0.1-5 Hz) and short time scales relevant for high bond strength and adhesion after application (5 Hz-100 Hz). Panel B is a plot of tan(6) highlights the frequency dependent shift at 1 Hz in viscoelasticity necessary for pressure-sensitive tissue adhesion. Panel C shows creep compliance of polymer blends in compression. The combination of viscosity and elasticity present in the polymer blends allows for pressure sensitivity (Panel D) and strong adhesion (Panel E), respectively. Panel F shows strain recovery in tension for various polymer blends.
Figure 16:
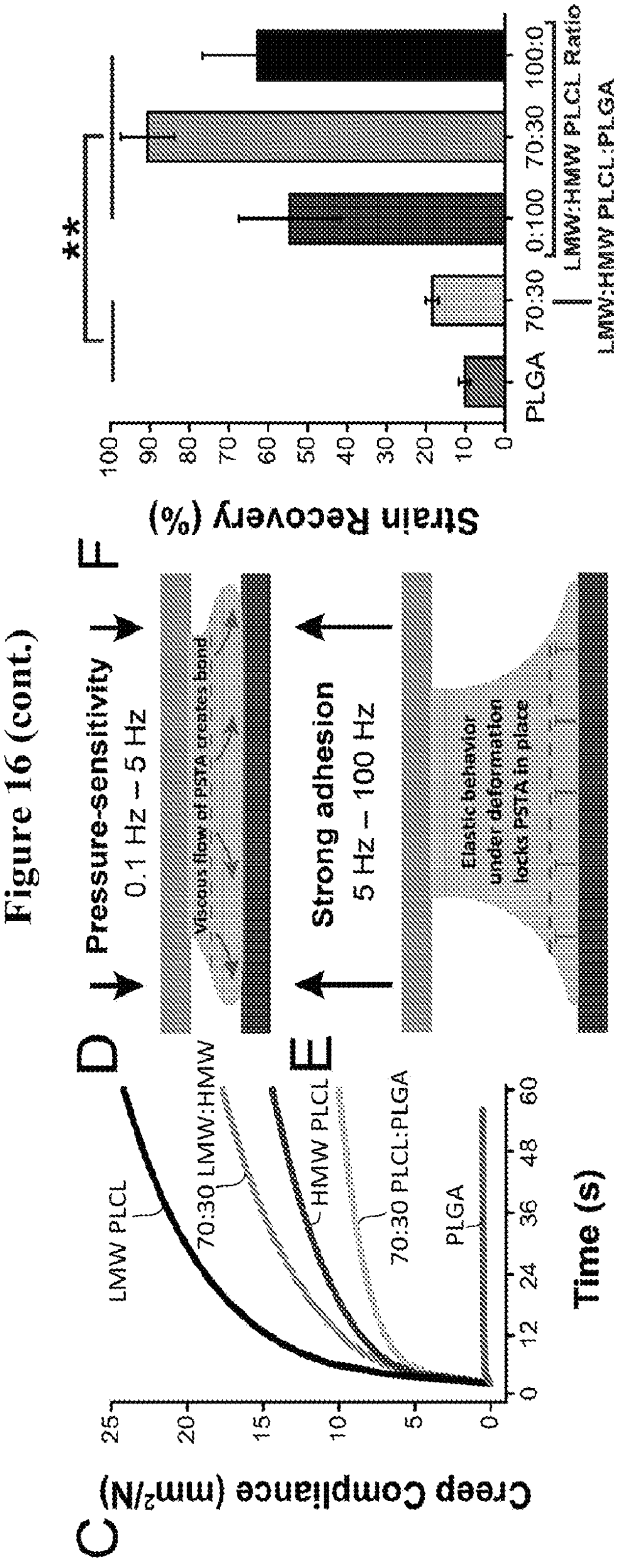

The viscoelasticity of the PSTA dictates its ability to quickly form adhesive bonds with high strength. Shear rheology was used to determine the relative modulus and frequency-dependent viscoelasticity of the PSTA polymer blends. Blends with tack-especially those containing LMW PLCL-exhibited lower storage modulus (G') and loss modulus (G") (FIG. 16, Panel A). The ratio of G" to G', plotted as tan(δ), represents the relative influence of viscous and elastic behavior (FIG. 16, Panel B); it captures the unique ability of these elastomeric polymer blends to be viscous on long time scales (corresponding to 0.1-5 Hz) and elastic on short time scales (5-100 Hz). Both 70:30 PSTA blends are shifted towards the viscous-dominated regime (tan(δ)>1): this imbues them with the high wettability and compliance (FIG. 16, Panel C) necessary to quickly form adhesive bonds under pressure (FIG. 16, Panel D) that pure HMW polymer cannot.

Blends of synthetic rubber, such as polyisobutylene and poly(styrene-butadiene-styrene) block copolymers and a phenolic tackifying resin, have been widely used for pressure sensitive adhesion to non-tissue, dry surfaces in consumer products like sticky notes (Deng, X. (2018) *Progress on Rubber-Based Pressure-Sensitive Adhesives*, J. Adhes. 94(2):77-96; Shin, J. et al. (2011) *Pressure-Sensitive Adhesives from Renewable Triblock Copolymers*, Macromolecules 44(1):87-94). These pressure-sensitive adhesives (PSAs) have also been repurposed for topical applications, such as adhesive bandages as discussed above. Research has established that their strong pressure-sensitive adhesion is a feature of their viscoelasticity, especially those that possess a transition from viscous to elastic behavior at intermediate frequency (Mazzeo, F. A. (2002) *Characterization of Pressure Sensitive Adhesives by Rheology*, TA Instrum. Rep. RH082, 1-8; Vendamme, R. et al. (2014) *Recent Synthetic Approaches and Emerging Bio-Inspired Strategies for the Development of Sustainable Pressure-Sensitive Adhesives Derived from Renewable Building Blocks*, J. Appl. Polym. Sci. 131(17)).

Incorporating the HMW component allows the PSTA to retain sufficient elasticity under sudden deformation to form a durable bond that does not succumb to weak disruptive forces (FIG. 16, Panel E). PSA formulations typically feature an elastomer with a rubbery region whose glass transition temperature ($T_g$) is 40-70° C. less than the operating temperature and glassy regions that resist flow (Creton, C. et al. (2009) *Large-Strain Mechanical Behavior of Model Block Copolymer Adhesives*, Macromolecules 42(20):7605-7615). In tension, the PLCL-based PSTA blends demonstrate high strain recovery (FIG. 16, Panel F). The PLCL selected for the PSTA (70:30 L:CL ratio) possesses a $T_g$ of −7° C., which is ideal given that the operating temperature is body temperature (37° C.). L:CL ratio refers to the relative amounts of lactide and caprolactone monomers in the polymer (which is independent of the relative amounts of LMW polymer and HMW polymer (e.g., PLCL), despite the ratio being the same as amounts of LMW/HMW polymers in exemplary blends). Such ratio may be varied, e.g., to attain different thermal or mechanical properties as desired. For example, the poly(lactide-co-glycolide) PLGA utilized has a 50:50 ratio of lactide to glycolide.

Figure 17:
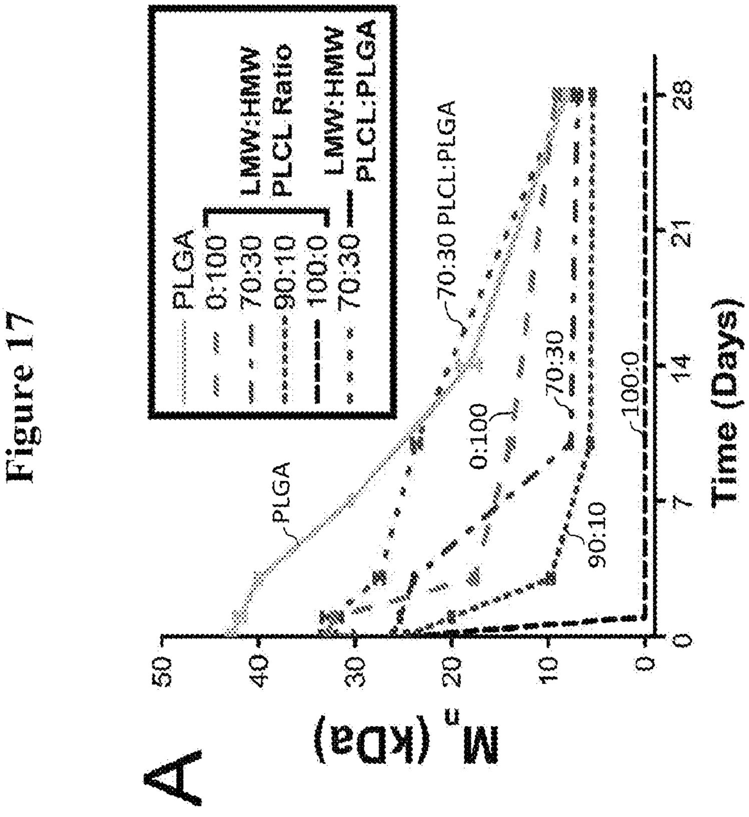
FIG. 17 shows gel permeation chromatography (GPC) (Panel A), mass loss (Panel B), tensile stiffness (Panel C), and failure strain (Panel D) of polymer blend adhesives during in vitro degradation. Panel E is a three-dimensional regression plot of time, adhesion strength, and tan(6) showing the interplay between degradation, rheology, and pull-off tissue adhesion.
Figure 17:
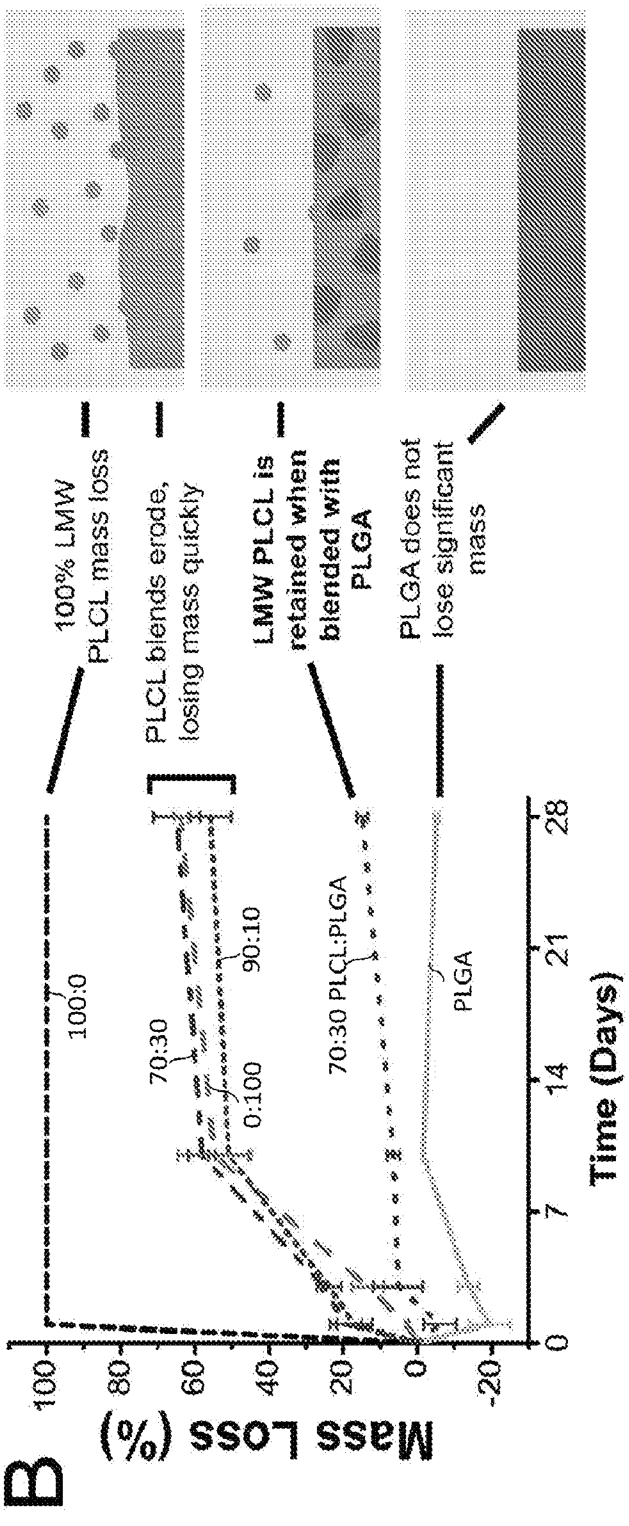
Figure 17:
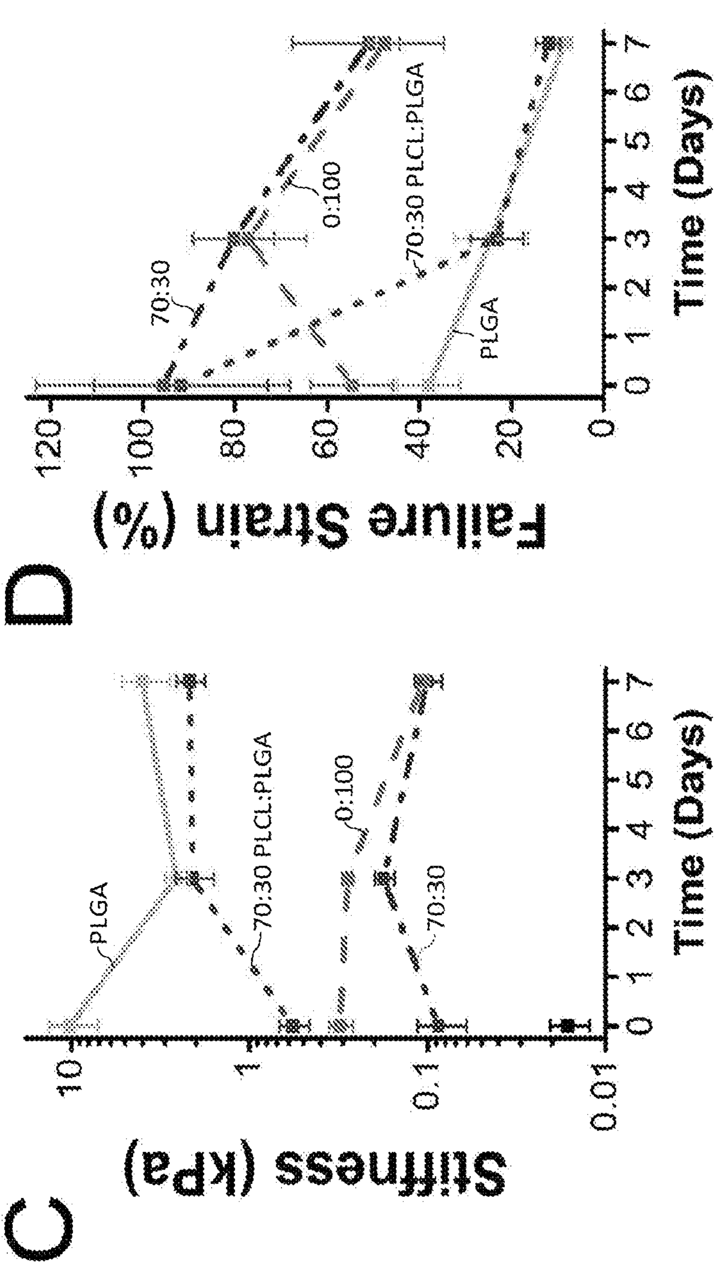
Figure 17:
Figure 17:
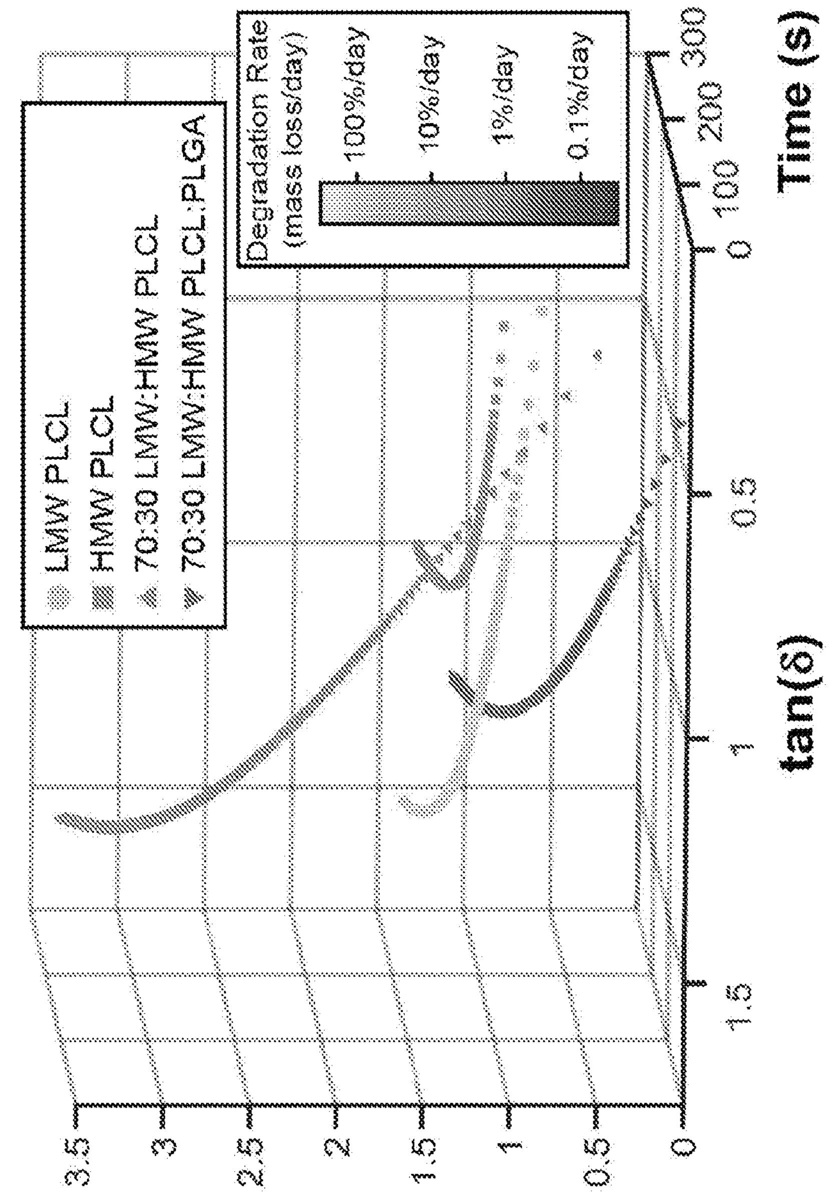

Biodegradation of synthetic polyesters in vivo is a function of both polymer chain cleavage due to hydrolysis and erosion of LMW aggregates. Simulated mass loss studies and gel permeation chromatography (GPC) were performed to quantify both aspects of biodegradation. PLGA (50:50 L:G) primarily undergoes bulk polymer chain cleavage (GPC, FIG. 17, Panel A), with minimal mass loss due to erosion occurring over 28 days (FIG. 17, Panel B). However, LMW PLCL completely erodes in 1 day and HMW PLCL undergoes a combination of erosion and bulk degradation. Blends of these exhibit a range of degradation speeds, determined by the HMW component. PLGA can be used to create slow-eroding PSTAs: adhesive blends with the pressure-sensitive properties of LMW PLCL (FIG. 17, Panel B, schematic inset). Blends of LMW and HMW PLCL also have low stiffness and high failure strain throughout their degradation (FIG. 17, Panels C-D). The synergy in desirable degradation rate, viscoelasticity, and high adhesive strength afforded by a 70:30 blend of LMW and HMW PLCL is illustrated by FIG. 17, Panel E, which consists of a logarithmic regression model of adhesion strength versus time and tan(δ).

Figure 18:
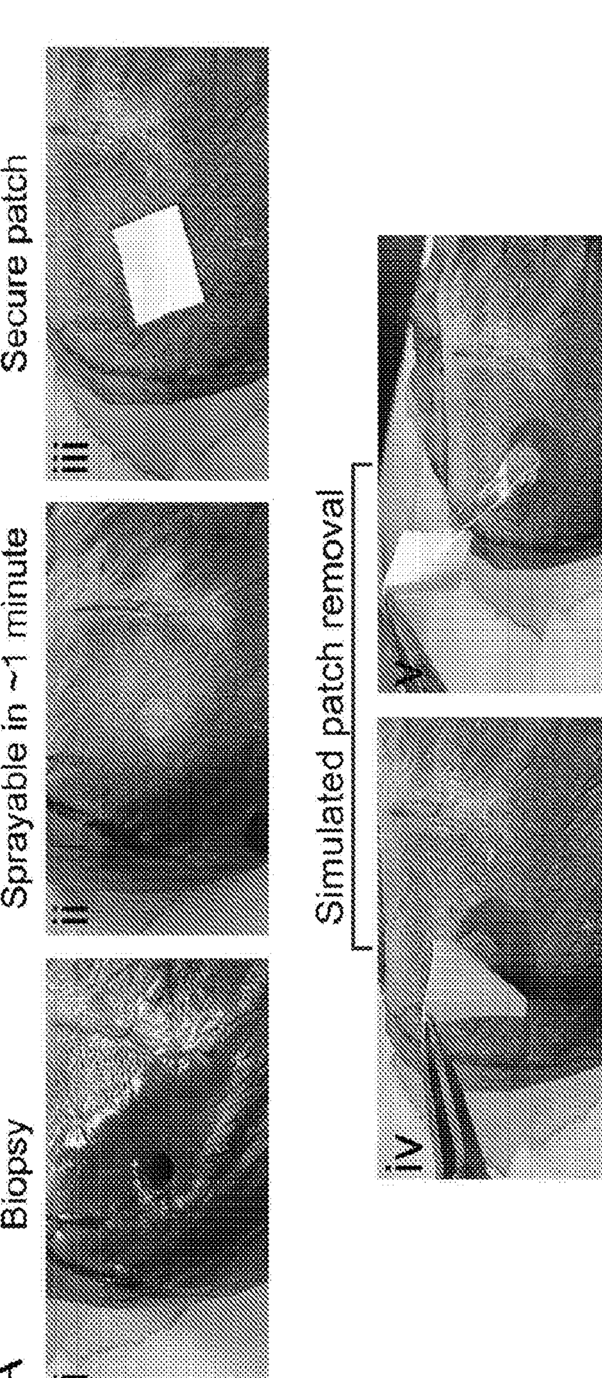
FIG. 18 shows an exemplary application strategy for sprayable pressure sensitive tissue adhesive (PSTA) and immune response towards PSTA components. PSTA can be sprayed directly onto a biopsy site (Panel Ai), forming a thin coherent layer in approximately 1 minute (Panel Aii). A cardiac patch can be secured to the biopsy site by applying pressure (Panel Aiii). During patch removal, the adhesive produces a strong bond (Panel Aiv) with high energy dissipation through material stretching and cracking prior to failure (Panel Av). Panel B shows frequency of fibrotic adhesions to the fat pads and implant fragmentation for polymers implanted in the intraperitoneal space of a mouse model, at 3 and 10 days post-surgery. Serum levels of tumor necrosis factor-α (TNF-α) (Panel C) and interferon-γ (IFN-γ) (Panel D) for the same model are shown.
Figure 18:
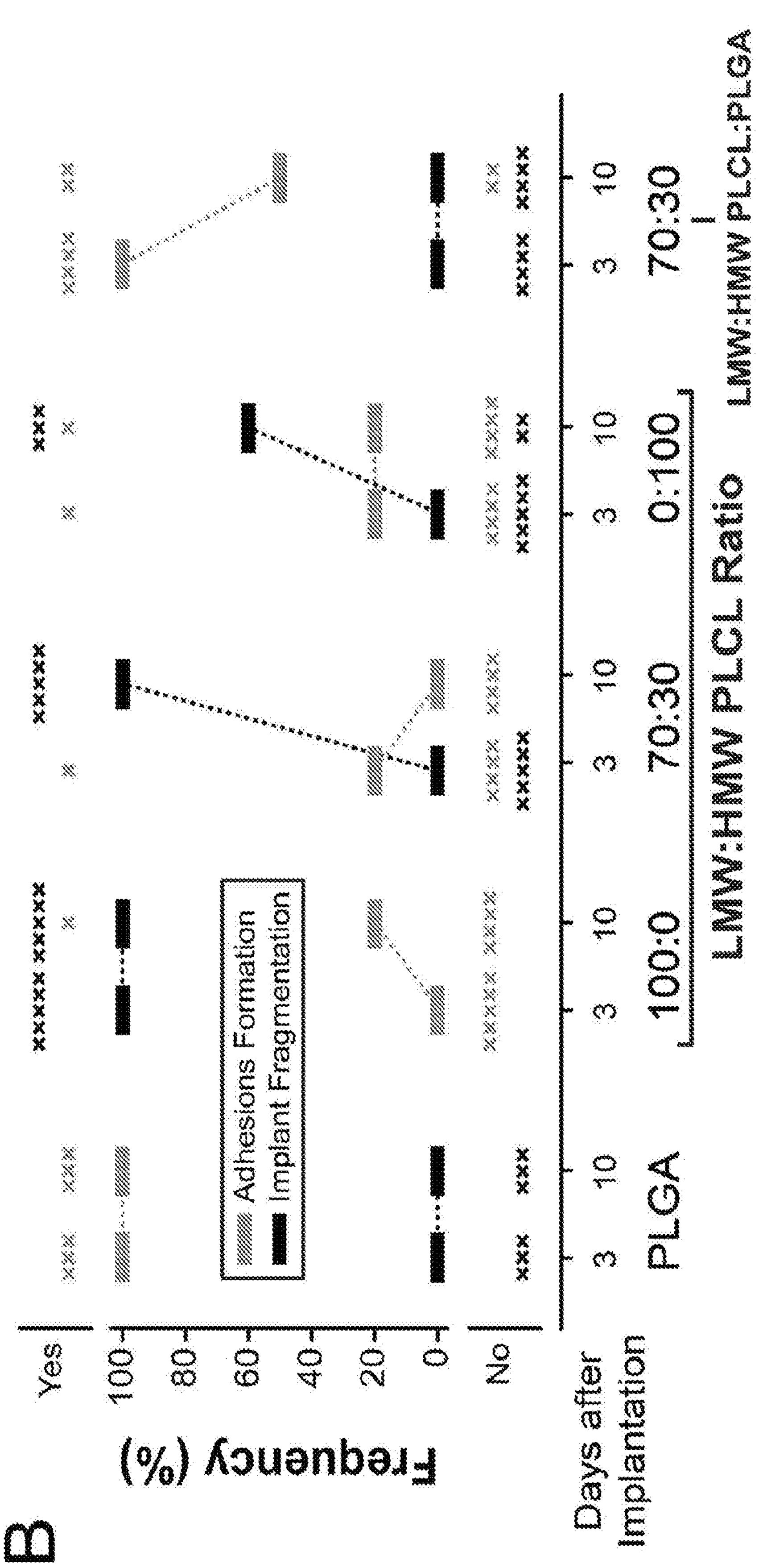
Figure 18:
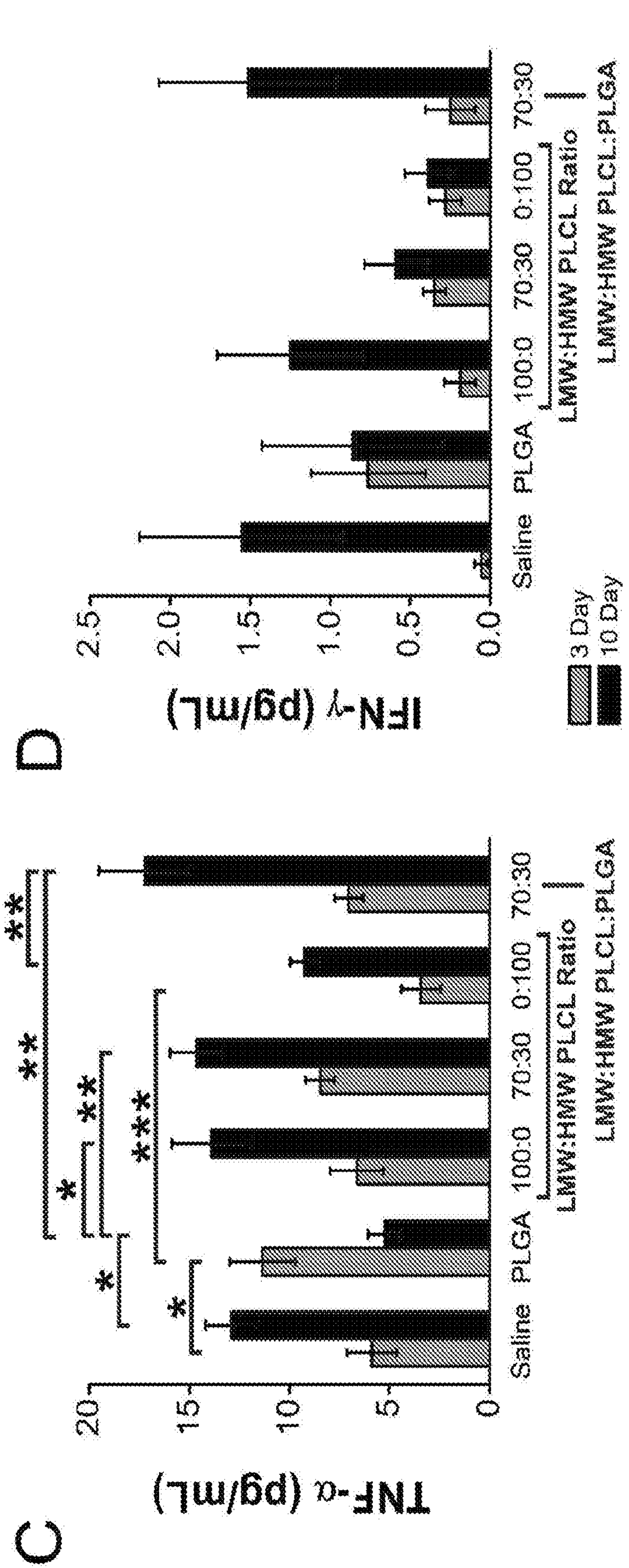

The sprayable PSTA can be delivered directly to the surgical site, allowing for custom fabrication of adhesive layers. It produces an initially porous mat that can span wounds (FIG. 18, Panel Ai-ii). This adhesive layer can be used to secure a small biomedical device, such as a cardiac patch (FIG. 18, Panel Aiii). When removed, the PSTA exhibits strong adhesion to both surfaces (FIG. 18, Panel Aiv), dissipating a high amount of energy through stretching before detachment (FIG. 18, Panel Av). The PSTA layer remains sticky after detachment but leaves little to no residue.

To determine the potential immune response to the fast-degrading components of the PSTA, we employed an intraperitoneal space implantation mouse model used to evaluate fibrosis (Doloff, J. C. et al. (2017) *Colony Stimulating Factor-*1 *Receptor Is a Central Component of the Foreign Body Response to Biomaterial Implants in Rodents and Non-Human Primates*, Nat. Mater. 16(6):671). Surprisingly, PSTAs composed exclusively of PLCL produced fewer cases of fibrotic adhesions to the fat pads at 3 and 10 days than those that incorporated PLGA (FIG. 18, Panel B). In the context of implanted materials, fibrosis may occur due to either: (1) chronic inflammation in response to the implanted material; or (2) acute inflammation from the wound healing response to surgical trauma that inhibits fibrinolysis (Menzies, D. (1993) *Postoperative Adhesions: Their Treatment and Relevance in Clinical Practice*, Ann. R. Coll. Surg. Engl. 75(3):147-153; Arung, W. et al. (2011) *Pathophysiology and Prevention of Postoperative Peritoneal Adhesions*, World J. Gastroenterol. WJG 17(41):4545-4553; Kamel, R. M. (2010) *Prevention of Postoperative Peritoneal Adhesions*, Eur. J. Obstet. Gynecol. Reprod. Biol. 150(2):111-118; Maciver, A. H. et al. (2011) *Intra-Abdominal Adhesions: Cellular Mechanisms and Strategies for Prevention*, Int. J. Surg. 9(8):589-594; Brüggmann, D. et al. (2010) *Intra-Abdominal Adhesions*, Dtsch. Ärztebl. Int. 107(44):769-775).

Interestingly, polymer degradation rate and mode played a critical role in the formation of fibrotic adhesions in this model. Each implant sample was also examined for fragmentation, which indicates high levels of erosion during degradation (FIG. 18, Panel B).

Those that degrade quickly, and primarily via erosion, like LMW PLCL, produced no adhesions to the fat pad; the implant itself degrades into soft fragments which could be found in the intraperitoneal space. PLGA implants, which primarily degrade via bulk chemical degradation, can be found intact and were more frequently associated with adhesions to the abdominal fat pads or other organs. Serum levels of tumor necrosis factor-α (TNF-α) and interferon-γ (IFN-γ) were also determined (FIG. 18, Panels C-D). TNF-α and IFN-γ were rarely significantly different between the saline-injected sham procedure and other treatments, except in cases where the serum of the polymer-treated mice had decreased levels. The only case of elevated TNF-α compared to saline injection was for PLGA, which may be connected to the more severe immune response that coincides with fibrosis. This reduction in fibrosis when using PLCL-based PSTA blends suggests that it may be possible to reduce fibrotic adhesions using polymer blending strategies that promote erosion.

Example 3

Pressure-Sensitive Tissue Adhesives (PSTAs) Comprising Blends of High and Low Molecular Weight Poly(Lactide-Co-Caprolactone) (PLCL)

Materials and Methods

Pressure-sensitive tissue adhesives (PSTA) were developed comprising blends of low and height molecular weight poly(lactide-co-caprolactone) (PLCL). Two different pressure sensitive blends of PLCL were evaluated, one containing pure high molecular weight (HMW) PLCL and one containing a 50:50 blend (50:50 L:H) of HMW PLCL and low molecular weight (LMW) PLCL, which acts as a tackifier to enhance adhesion. The polymer solution including 20% w/v polymer (including both LMW PLCL and HMW PLCL), which is dissolved in acetone as described above.

Figure 19:
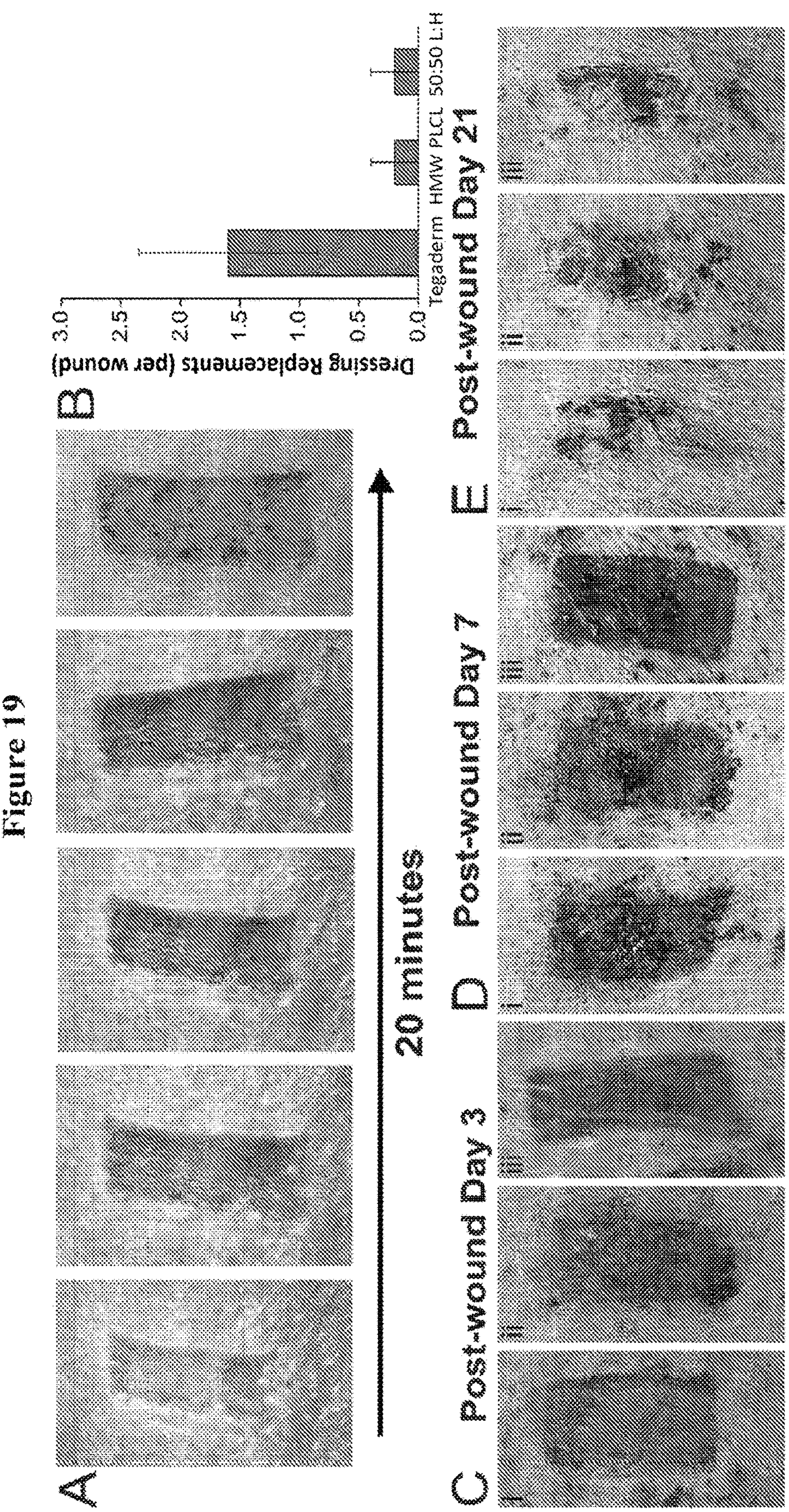
FIG. 19, Panel A shows partial thickness wound sprayed with PLCL blend pressure sensitive adhesive, transitioning from solution blow spun fibers to a transparent film. Panel B shows graphically the number of required dressing replacements per wound due to dressing adherence. Sample images of healing wounds at 3 days (Panel C), 7 days (Panel D), and 21 days (Panel E) after wound creation, using either (i) HMW PLCL, (ii) 50:50 L:H PLCL, or (iii) Tegaderm.

An airbrush was used to deliver polymer fibers directly to porcine partial thickness wounds to assess the possible effects of a biodegradable PSA composed of the PLCL blends on wound healing. Pure adhesive (with no backing) was used in these experiments to isolate the effects of polymer choice. PLCL, which has a glass transition temperature of approximately −11° C., transitions from a fibrous covering to a thin, conformal, and transparent film (FIG. 19, Panel A). While soft at room and body temperature, their $T_g$s are greater than the PSA coating of a plastic bandage.

Wound dressing changes were tracked over the first 14 days of healing to determine how the adhesive affected the frequency at which the dressing had to be replaced (FIG. 19, Panel B). Both PLCL-based adhesives required fewer dressing changes than the control dressing, Tegaderm, which is a conventional PSA backed with a thin polyurethane film. Visual assessment of the wounds was regularly performed as they were healing, with images presented at post-wound day (PWD) 3, PWD 7, and PWD 21 (FIG. 19, Panels C-E). Some exudate buildup was apparent underneath the Tegaderm dressing at PWD 3 (FIG. 19, Panel Ciii). At PWD 21, most wounds appeared to show similar amounts of scarring.

Figure 20:
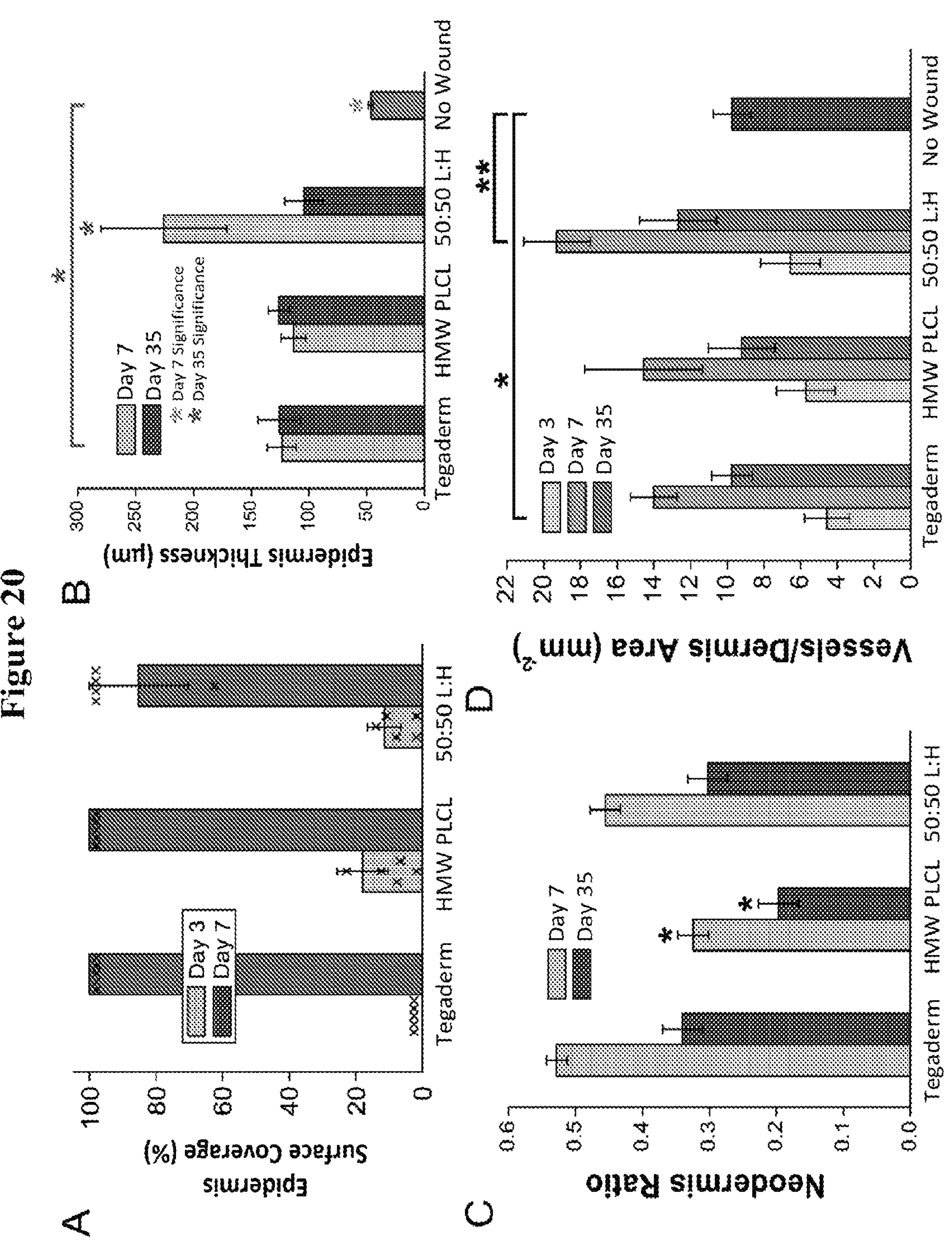
FIG. 20 shows histological characteristics of partial-thickness wound healing for PLCL-based pressure sensitive adhesives. Panel A shows epidermis surface coverage on the healing wound at Day 3 and Day 7. Individual data points are overlaid. Panel B shows epidermis thickness of the healing wounds. Panel C shows the ratio of neodermis thickness to total dermis thickness. Panel D shows blood vessel density in the dermis of the healing wound. Asterisks indicate statistical significance: *=P<0.05, **=P<0.01.
Figure 21:
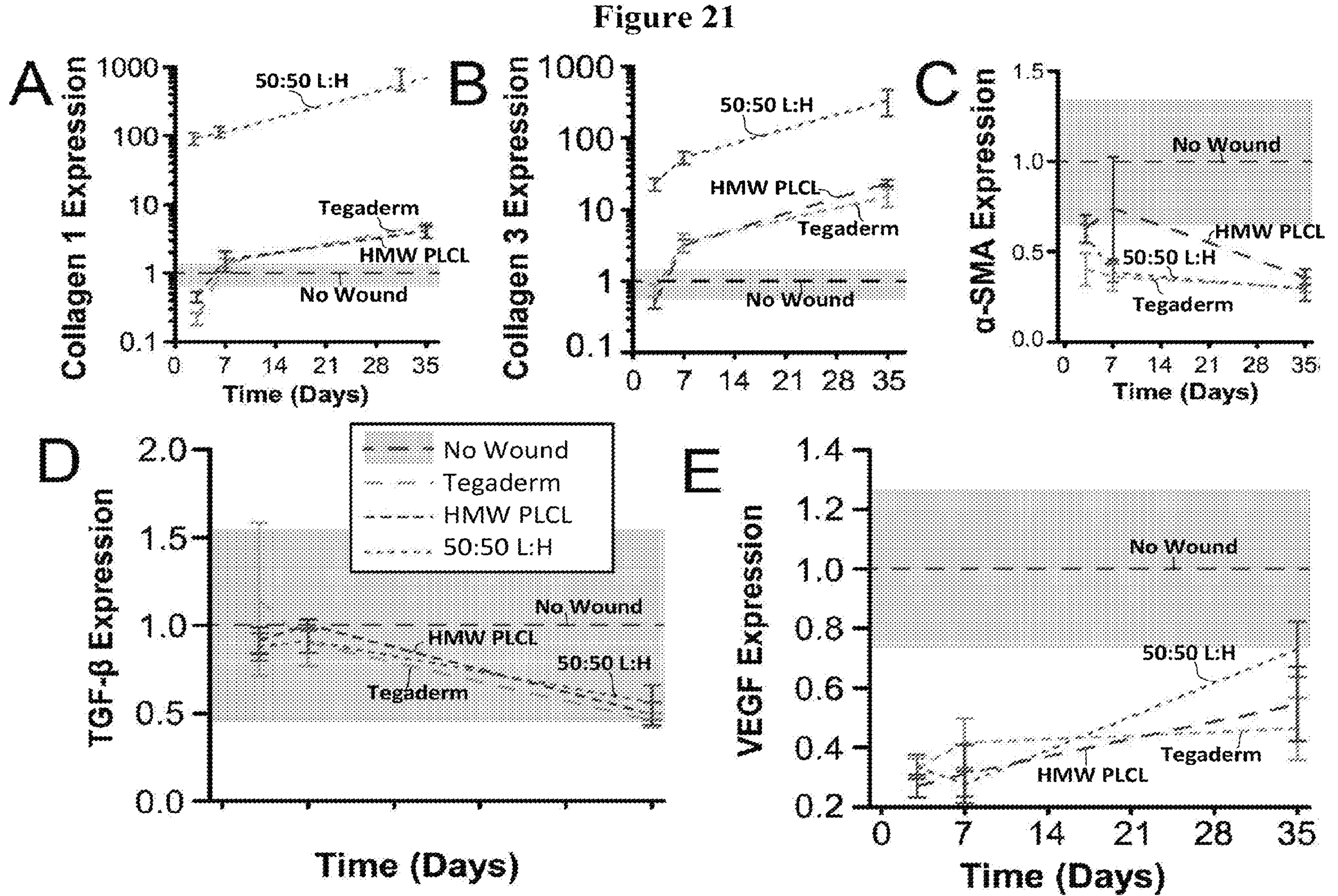
FIG. 21 shows RT-PCR measurements of Collagen I (Panel A), Collagen III (Panel B), α-SMA (Panel C), TGF-β (Panel D), and VEGF (Panel E). Gene expression measured relative to those of normal uninjured (no wound) skin, which is plotted with a black dotted line and a gray band indicating standard error.

While few wounds displayed any healed epidermis at PWD 3, nearly all wounds showed complete epidermis coverage by PWD 7, which was confirmed with histology (FIG. 20, Panel A). Increased epidermis thickness was noted in the 50:50 L:H blend at PWD 7 but returned to levels comparable to the other wound dressings at PWD 35 (FIG. 20, Panel B). Neodermis ratio was significantly lower for HMW PLCL dressings at PWD 7 and PWD 35 (FIG. 20, Panel C). Revascularization is an indication of wound healing, as angiogenesis plays a critical role during the proliferative stage of wound repair (Gurtner, G. C. et al. (2008) *Wound Repair and Regeneration*, Nature 453:314-321; Li, J. et al. (2003) *Angiogenesis in Wound Repair: Angiogenic Growth Factors and the Extracellular Matrix*, Microsc. Res. Tech. 60(1):107-114). Blood vessel regeneration was decreased for Tegaderm at PWD 3, while 50:50 L:H displayed increased blood vessel density relative to the no wound control at PWD 7 (FIG. 20, Panel D). All returned to normal levels at PWD 35. Collagen 1 and collagen 3 mRNA expression were elevated for 50:50 L:H dressings relative to Tegaderm and HMW PLCL (FIG. 21, Panels A-B), while alpha smooth muscle actin (α-SMA), transforming growth factor beta (TGF-β), and vascular endothelial growth factor (VEGF) were expressed similarly between the three groups (FIG. 21, Panels C-E).

Figure 22:
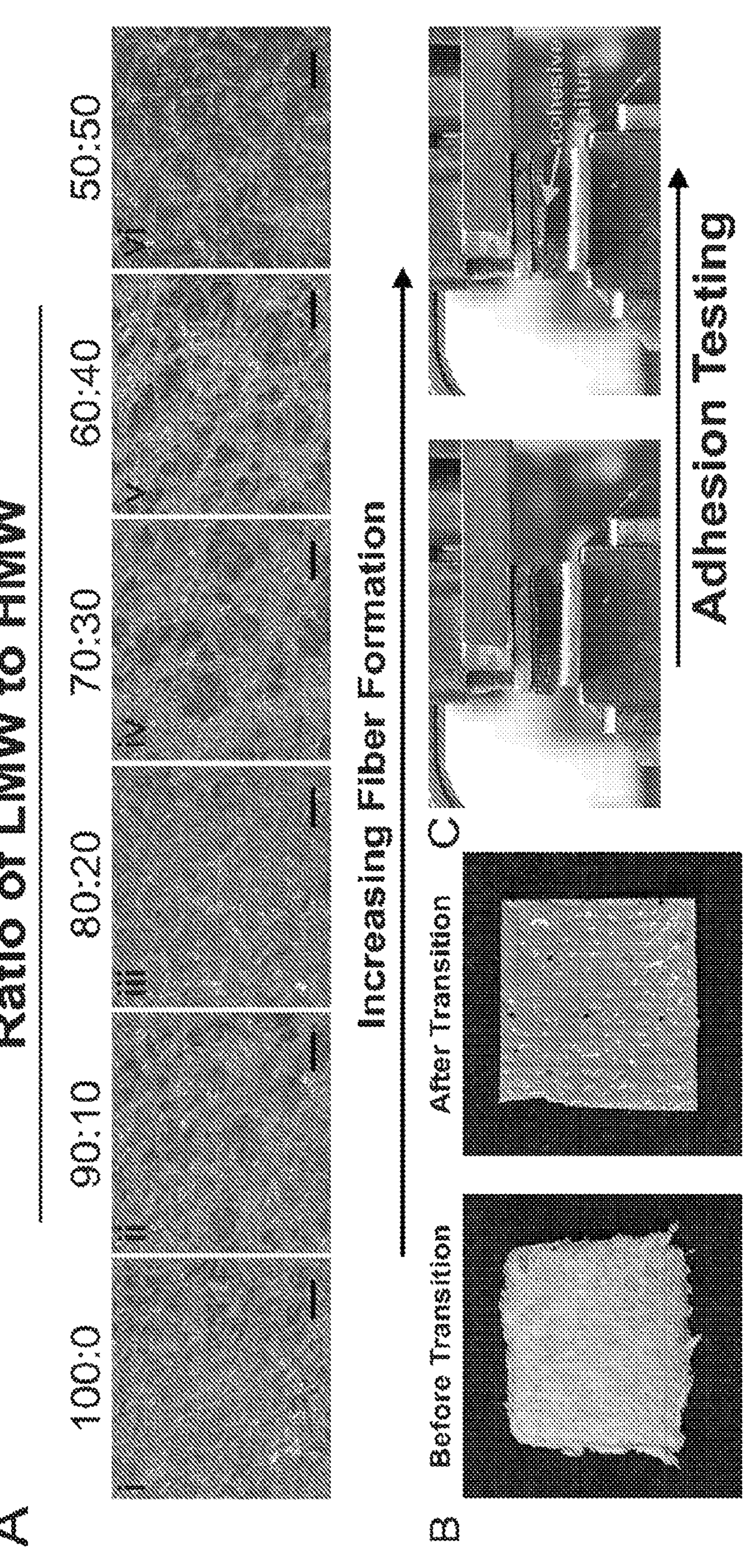
FIG. 22, Panel A are images of s images of fiber mats produced by SBS from an airbrush and showing increased fiber formation with increased HMW PLCL in the disclosed compositions. Panel B shows PLCL blends transition from fibers to a thin, adhesive film after 30 minutes. Panel C shows adhesion testing and showing that, during pull-apart adhesion testing, the adhesive stretches and breaks via cohesive failure (arrow).

After validating the safety and efficacy of using PLCL for use in wound healing applications, its adhesive properties were characterized along with processability towards use as the adhesive layer on a bandage. PLCL adhesives are sprayable with tunable fiber morphology (FIG. 22, Panel A). The fibers can be sprayed onto various targets and form a thin adhesive film after transitioning (FIG. 22, Panel B), allowing for simple fabrication. During adhesion testing, the film is soft enough to form tendrils during cohesive failure, indicating the formation of a strong bond (FIG. 22, Panel C).

PLCL adhesives were sprayed onto the backing of a plastic bandage (FIG. 23, Panel A) and compared pull-off adhesion strength to a conventional PSA. After spraying and transitioning, both PLCL adhesives formed a thin film with similar morphology to the conventional adhesive (FIG. 23, Panels B-C). Adhesion strength to porcine skin was significantly greater for the 50:50 L:H blend of PLCL as compared to both pure LMW PLCL and pure HMW PLCL (FIG. 23, Panel D). This demonstrates the ability of achieving a desired combination of tackifying (LMW PLCL) and reinforcing (HMW PLCL) polymers to promote adhesion. 50:50 L:H also produced comparable adhesion strength to the conventional bandage.

Example 4

Tissue Adhesives Comprising Antimicrobial Agents: Adhesive compositions comprising poly(lactic-co-glycolic acid), poly(ethylene glycol) (PLGA/PEG), and silver (Ag) particles were examined. As demonstrated, blends of PLGA/PEG/Ag compositions may be sprayed using solution blow spinning (SBS) for the deposition of biodegradable polymer fibers containing antimicrobial silver directly onto a wound site.

Materials and Methods

Solution Blow Spinning Process and Polymer Solutions: A commercially available airbrush (Master Airbrush G22-SET, 0.2 mm nozzle diameter) was used in all SBS protocols involved in the following experiments. For porcine in vivo wound healing studies, a handheld, $CO_2$ cartridge-fed regulator was used. In all other studies, gas was supplied through a $CO_2$ tank equipped with a regulator. The distance between the airbrush nozzle and the application surface was approximately 10 cm for all studies. All polymer solutions were dissolved in ethyl acetate (Fisher), except for those that were dissolved in acetone (Fisher) for morphology studies using the scanning electron microscope. Polymer solutions consisted of 10% w/v PLGA (inherent viscosity=0.86 dL $g^{-1}$ in hexafluoroisopropanol, $M_n$=48800±450 g $mol^{-1}$ measured with gel permeation chromatography against Agilent polystyrene standards, 50:50, Lactel), and 5% w/v PEG ($M_n$=950-1050 g $mol^{-1}$, Sigma-Aldrich, St. Louis, MO). Silver nitrate ($AgNO_3$, Sigma-Aldrich, St. Louis, MO) if added, was added after polymer dissolution and the solution was stirred overnight before use.

Scanning Electron Microscopy and Energy Dispersive X-ray Spectroscopy: A Hitachi SU-70 Schottky field emission gun scanning electron microscope was used to image nanofiber mats sputter coated with gold. Snapshots (n=3) were taken across the surface of the fiber mat. Fiber diameter and porosity were determined using the DiameterJ plugin for ImageJ (n=2-4) (Hotaling, N. A. et al. (2015) *Diameter J: A validated open source nanofiber diameter measurement tool*, Biomaterials 61:327-338). Energy Dispersive X-Ray Spectroscopy (EDS) was used to measure weight fraction. EDS-determined abundances were converted to weight fraction based on the three primary elemental components of the polymer fibers being carbon, oxygen, and silver.

Tensile Mechanical Testing: Polymer samples were Tensile tests were made using a TA Instruments DMA Q800 equipped with a film tension clamp. Samples were stretched under a controlled force ramp from 0 N to 5 N at a rate of 0.01 N $min^{-1}$. Measurements were made either at room temperature or at 37° C. after a 10 min isothermal period. Elastic modulus was calculated from the linear region of the resulting stress/strain curve. Each sample type was replicated 5 times (n=5).

Differential Scanning Calorimetry (DSC): Approximately 10 mg samples of fiber mats were sealed in aluminum hermetic pans (TA Instruments) using a sample encapsulation press. Differential scanning calorimetry (DSC) measurements were made on a TA Instruments DSC Q100. Samples were held isothermal at −50° C. for 5 min and then heated and cooled from −50 to 80 to −50° C., at a rate of 10° C. $min^{-1}$ for two continuous cycles. The inflection point of the heat flow during the $T_g$ was used to determine the midpoint.

Silver Elution Studies: A 2 mL of polymer solution was used to fabricate fiber mats containing various amounts of $AgNO_3$, which were then weighed (n=3). The fiber mats were then submerged in 4 mL of deionized water, and stored at a constant temperature of 37° C. The supernatant was sampled periodically over 30 days. Samples were analyzed by inductively coupled plasma-atomic emission spectroscopy (ICP-AES) on a Shimadzu ICPE-9000, measuring at 328 nm for Ag+. Mass of silver released was normalized to the mass of the fiber mat.

Wound Closure Adhesion Testing: Wound closure adhesion testing was performed on the TA Instruments DMA Q800. 1 cm by 1 cm sections of porcine skin were attached to rectangular clamps using cyanoacrylate glue. The rectangular clamps were brought together end to end, and 1 mL of sealant polymer solution was deposited on this joint, closing the gap between the two skin-coated clamps (see ASTM F2458-05). The sealant was carefully applied and trimmed to avoid coating the interface between the ends and edges of the clamps. It was then allowed to set at 37° C. for 10 minutes before testing. A controlled force ramp was used to increase force at a rate of 1 N $min^{-1}$ until failure. Failure type was recorded as either adhesive or cohesive. Force values were normalized to the surface area of skin coated by the adhesive, which was measured using calipers, giving adhesive strength. Each sample type was replicated five times (n=5).

Antimicrobial Zone of Inhibition: The antibacterial effects of the PLGA/PEG/Ag dressing were tested in vivo against *Staphylococcus aureus* (ATCC 6538) and *Escherichia coli* (ATCC 8739) using standard methods of disk susceptibility testing (Balouiri M. et al. (2016) *Methods for in vitro evaluating antimicrobial activity: A review*, J Pharm Anal 6:71-9; Kong H. and Jang J. (2008) *Antibacterial properties of novel poly(methyl methacrylate) nanofiber containing*

*silver nanoparticles*, Langmuir 24:2051-6). Overnight cultures of each bacterium were grown in LB broth for 24 hours after inoculation from frozen bacterial glycerol stock. The solution was then diluted with plain LB broth to 0.5 McFarland standards based on absorbance of 0.08-0.12 by spectrophotometer at 625 nm. 1.0 mL of the culture was then plated onto standard LB agar using a cell spreader. PLGA/PEG/Ag antimicrobial effects were tested against a broad-spectrum antibiotic, gentamicin sulfate (Sigma-Aldrich, St. Louis, MO). Blank 10 mm Kirby-Bauer disks (Sigma-Aldrich, St. Louis, MO) were loaded with gentamicin solution in sterile water at a potency of 10 μg. After air-drying for 15 min, the gentamicin disks were pressed onto the agar. Disks of PLGA/PEG/Ag (1 mg/mL, Ag-M, and 5 mg/mL, Ag-H) were made by spraying PLGA/PEG/Ag solution onto sterile glass coverslips and cutting into 5 mm disks (n=3-5). The disks were pressed onto the agar surface with at least 2 cm distance between disks. All disks were then wet with 30 μL sterile water to facilitate release of Ag+. After incubation for 24 hours at 37° C., the zone of inhibition (ZOI) for each disk was measured using a caliper. Given the size differences in disk size, the ZOI was normalized to the disk diameter.

Mouse L929 Fibroblast Cytotoxicity: Cytotoxicity of the SBS polymer dressings was tested against L929 mouse fibroblasts by elution method as described by ISO-10993-5 (Biological Evaluation of Medical Devices—Part 5: Tests for in vitro cytotoxicity. Switzerland: International Organization for Standardization; 2009). PLGA/PEG/Ag and PLGA/PEG were blow-spun onto sterile 5×5 cm coverslips. The polymer mats were then removed from the coverslips and eluted in culture media of Dulbecco's modified Eagle medium supplemented with 10% fetal bovine serum (Gemini Bio-Products Inc., Woodland, CA, USA), L-glutamine and 1% penicillin and streptomycin at standard conditions (37° C., 5% $CO_2$) for 24 hours. The elutions were then diluted to 1×, 10×, and 100× dilutions, and cell viability was tested against the different dilutions.

L929 fibroblasts (ATCC CCL-1, Manassas, VA) were then expanded in Dulbecco's modified eagle media with 10% fetal bovine serum from frozen stock under standard conditions in tissue culture flasks. Cells were incubated until achieving a confluent monolayer in flask. L929 cells were then washed with 0.25% trypsin solution to obtain a cell suspension, which was then diluted to cell density of $10^5$ cells/mL. L929 fibroblasts were then plated into 96-well plates at 100 uL per well and incubated for 24 hours under standard conditions. The culture media was then removed by pipette. Wells were then treated to control (D10-complete media), 25 ug/mL puromycin, or diluted elutions of PLGA/PEG/Ag and PLGA/PEG. This measurement was repeated eight times for each diluted elution (n=8).

Porcine Partial-Thickness Wound Healing Model: Animal studies were performed in the research animal facility at Children's National Health System with IACUC approval (protocol #30454). Two 20-25 kg Yorkshire swine were used in this pilot study. Each animal was acclimated to the facility at least 24 hours before the study. After sedation by ketamine hydrochloride and xylazine hydrochloride, the animals were intubated and anesthetized with isofluorane. Each pig was then positioned prone, and back hair was removed using an electric shaver. The area of the back, from the scapula to the brim of the pelvis, was sterilized with betadine scrub and then draped with sterile towels. Six partial thickness (0.6 mm depth) skin wounds were made on each side of the paravertebral skin with a dermatome (Humeca, Woodstock, GA), making a total of twelve wounds per animal. The wounds were made 1.5 cm long in cranial-caudal direction and 4 cm wide. Each wound was separated by 1.5 cm of normal skin. The wounds were randomized to treatment by Tegaderm (3M, St. Paul, MN), PLGA/PEG, or PLGA/PEG/Ag, resulting in a total of 4 wounds per dressing group per animal, over two animals (n=8). Wounds were uniformly sprayed with 2 mL of polymer solution, which produced complete wound coverage as determined by a surgeon. Wounds were assessed daily for healing and signs of infection by visual inspection. Dressing replacement was performed as needed until PWD 14. The experimental endpoint was chosen to be thirty-five days after initial wound creation. Wound healing was followed by wound size and scar tissue measurements by caliper on PWD 3, 7 and 35. 5 mm full thickness punch biopsies of the wounds were also taken on PWD 7 and 35. Biopsies on PWD 7 were taken 1 cm from the lower left corner of the wound, while biopsies for PWD 35 were taken at the center of the wounds. Pain was controlled by fentanyl patch to the foreleg for the first 72 hours after surgery, followed by intramuscular injections of buprenorphine after biopsies and as needed. Animals were not intubated on PWD 7 and isofluorane was given by snout mask on PWD 7 given the short biopsy procedure. After dermal biopsies on PWD 35, the animals were euthanized as per IACUC protocol.

Histological Analysis: Biopsied tissues were kept in 10% neutral buffered formalin until histological processing (Histoserv Inc., Germantown, MD). Punch biopsy samples were bisected along the longitudinal axis then embedded in paraffin wax. 5 μm sections were prepared and fixed onto glass slides and then stained with Masson's trichrome. Digital images of the histology slides were taken with TissueScope LE (Huron Digital Pathology, St. Jacob, Ontario) at 40× magnification then exported for analysis with ImageJ software (NIH). Images were scaled to 1 μm/pixel. Epidermal and dermal thicknesses were measured after cropping images to 3000 μm by 3000 μm. Epidermis thickness was measured at areas that show at least a basal layer of epidermal cells, stained red in Masson's trichrome. Total dermis thickness was measured from the base of the epidermis to the level of subdermal fat. Also measured was the thickness of the evolving dermal matrix, seen as disorganized collagen bundles (in light grey) above the layer of organized collagen bundles (dark grey). Thickness measurements were taken at the left, middle, and right side of the images, and the average of the three values was used to represent each of the thicknesses for each wound. The vascular density (vessels per $mm^2$ of dermis) of each biopsy was measured by counting the number of unique vessel structures in the dermis, including arterioles and venules, but not capillaries. Dermis area was measured using ImageJ. Density measurements were made by two researchers and averaged.

Wound Healing Gene Expression: Gene expression of α-SMA (α-smooth muscle actin), TGF-β1, collagen-I and collagen-III in the healed wounds were quantified using real-time PCR (RT-PCR). Full thickness biopsies were taken from the center of the healed wounds at PWD 35. Normal uninjured skin biopsies were also taken from both sides of the paraspinal back skin with samples from the upper and lower back. Gene expressions in the wounds were measured relative to those expressed in normal skin tissue. Biopsied tissues were snap-frozen in liquid nitrogen, and then stored at −80° C. until analysis.

RNA extraction from frozen tissue was performed by tissue homogenization in Trizol reagent (Life Technologies, Frederick, MD) and PureLink RNA Mini Kit (ThermoFisher Scientific). For all experiments, 3 μg RNA was used to synthesize first stand cDNA using High-Capacity cDNA Reverse Transcription kit (Life Technologies, Carlsbad, CA). RT-PCR was performed using TaqMan® Gene Expression Master Mix (Life Technologies) in a QuantStudio 7 Flex Real-Time PCR System (Thermo Fisher Scientific, Waltham, MA), according to the manufacturer's instructions. Reactions were performed in triplicate, including no template controls and amplification of a housekeeping gene, GAPDH. Gene-specific assays were Ss03373340_m1 for COL1A1, Ss04245588_m1 for αSMA, Ss04323768_g1 for COL3A1, Ss03382325_u1 for TGF-β1, and Ss03375629_u1 for GAPDH (Life Technologies). Changes in relative gene expression normalized to GAPDH levels were determined using the ΔΔCt method. The difference between the Ct values (ΔCt) of the gene of interest and the housekeeping gene is calculated for each experimental sample. Then, the difference in the ΔCt values between the experimental and control samples ΔΔCt is calculated. The fold-change in expression of the gene of interest between the two samples is then equal to $2^{(-\Delta\Delta Ct)}$.

Statistical analysis: For the animal experiments, all measurements are reported as means. Statistical analysis was performed on Stata (StataCorp, College Station, TX) or Origin (OriginLab, Northampton, MA). Typically, one-way ANOVA was used to compare group variation, followed by post-hoc pairwise Tukey comparison to determine significant differences between the groups. Statistical significance is considered for $p<0.05$. Typically, averages were plotted with error bars representing standard error. If no asterisks are shown, there are no significant differences among the groups.

Results

Effect of solvent on fiber morphology and silver content: We first evaluated whether solvent properties could affect the morphology of fibers produced by SBS, which is an important factor in fiber formation (Daristotle J. L. et al. (2016) *A Review of the Fundamental Principles and Applications of Solution Blow Spinning*, ACS Applied Materials & Interfaces 8:34951-63). Acetone has been previously used for SBS processes and does not affect cell viability on fabricated nonwoven fiber mats (Oliveira J. E. et al. (2011) *Nano and submicrometric fibers of poly(D,L-lactide) obtained by solution blow spinning: Process and solution variables*, J Applied Polym Sci 122:3396-405; A. M. Behrens et al. (2014) *In Situ Deposition of PLGA Nanofibers via Solution Blow Spinning*, ACS Macro Lett 3(3):249-254). However, silver nitrate's ($AnNO_3$) solubility in acetone at room temperature is only 4.4 mg/mL (Atherton Seidell P D. Solubilities of Inorganic and Organic Compounds. A Compilation of Quantitative Solubility Data from the Periodical Literature. New York/Gauthier-Villars et Cie., Paris, 1928. 569 Seiten: D. van Nostrand Company, Inc.). Ethyl acetate has lower toxicity than acetone and is able to dissolve nearly 10 times as much $AgNO_3$ up to a concentration of 27 mg/mL (Kogan V B, Fridman V M, Kafarov V V. Handbook of Solubility, Vol 1. Izd-vo AN SSSR; 1961). This makes it an excellent alternative candidate for SBS of polymers in situ.

Figure 24:
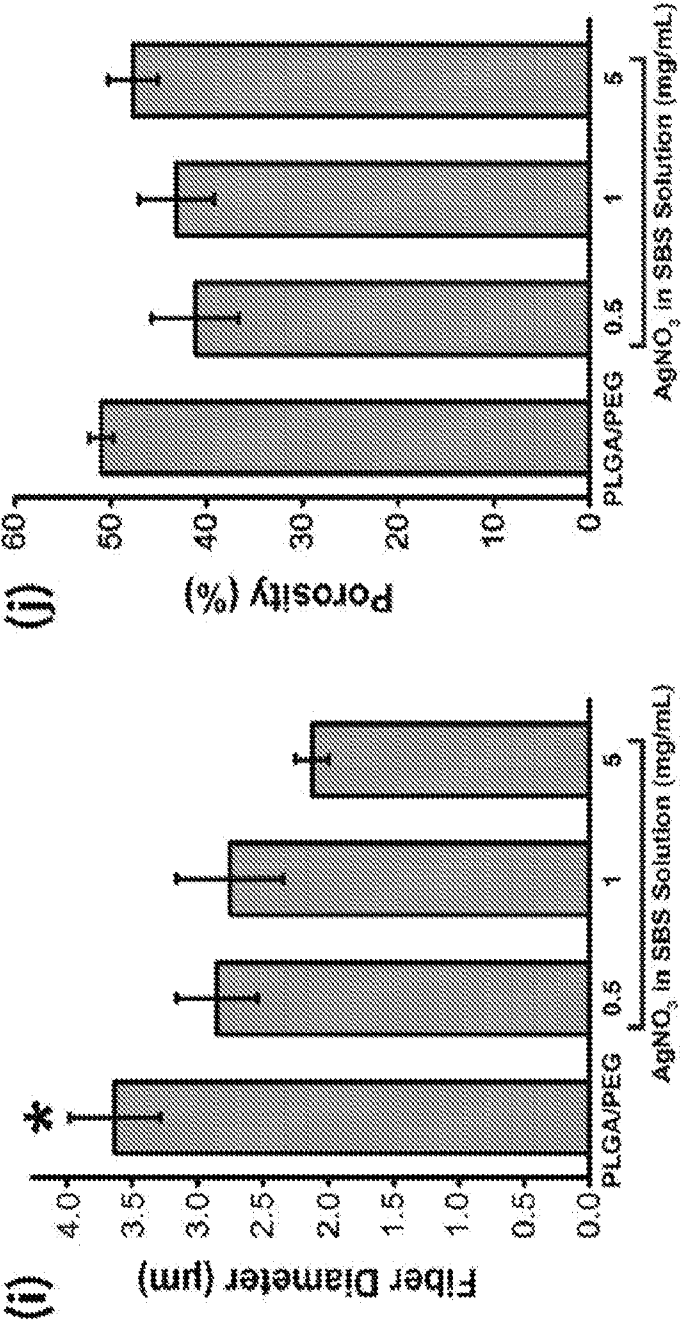
FIG. 24, Panels (a-h), are SEM images of PLGA/PEG fibers produced using solution blow spinning with increasing concentrations of AgNO3 added to the spinning solution. Fibers produced using acetone as the spinning solvent (Panels a-d) create a beads-on-a-string morphology when loaded with AgNO3, while those made with ethyl acetate (Panels e-h) have a consistent web-like fiber morphology. Scale bar=100 μm. When using ethyl acetate as the spinning solvent, there are decreases in fiber diameter with AgNO3 concentration (Panel i), while porosity (Panel j) is similar (n=2-4).

The pure PLGA/PEG samples for both acetone and ethyl acetate resemble each other in morphology (FIG. 24, Panels (a) and (e)). However, SBS from acetone produces fibers that exhibit an $AgNO_3$ dependent change towards a beads-on-a-string morphology (FIG. 24, Panels (b), (c) and (d)), which is characteristic of polymer solution jets that form spherical structures during the spraying process (Srinivasan S. et al. (2011) *Solution spraying of poly(methyl methacrylate) blends to fabricate microtextured, superoleophobic surfaces*, Polymer 52:3209-18). SBS from ethyl acetate continues to produce fibrous structures up to 5 mg/mL $AgNO_3$ (FIG. 24, Panels (f), (g) and (h)). Therefore, ethyl acetate was selected as the spinning solvent for the experiments.

Using ethyl acetate, fiber diameter decreases as silver content increases (FIG. 24, Panel (i)) while porosity remains constant (FIG. 24, Panel (j)). The difference in morphology may be related to the lower solubility of $AgNO_3$ in acetone, which evaporates quickly during spraying and may cause the aggregation of the silver salt. Ethyl acetate solubilizes much higher concentrations of $AgNO_3$ and has a lower evaporation rate than acetone, meaning that it is less likely to form the precipitates during spraying. The lower evaporation rate of ethyl acetate may also account for the high degree of branching or welding observed between fibers, a connection that has been observed in other SBS systems (A. M. Behrens et al. (2014) *In Situ Deposition of PLGA Nanofibers via Solution Blow Spinning*, ACS Macro Lett 3(3):249-254).

Figure 25:
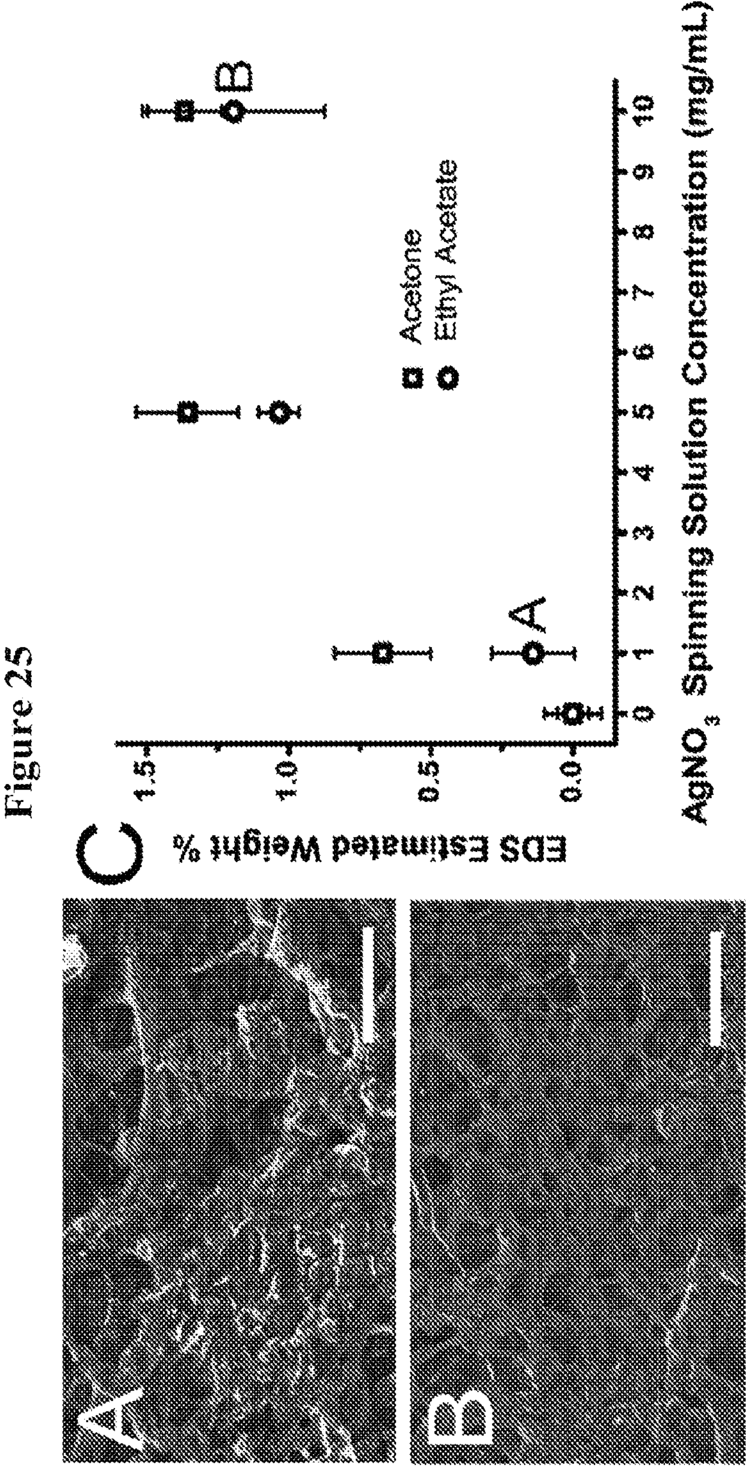
FIG. 25 are energy dispersive x-ray spectroscopy (EDS) images showing that PLGA/PEG fibers produced using solution blow spinning with ethyl acetate contains silver. EDS signal superimposed on scanning electron microscopy images of fibers produced from polymer solution containing 1 mg/mL (Panel A) and 10 mg/mL (Panel B) AgNO3. Scale bar=10 μm. Panel C is a plot of estimated weight percent of silver calculated from EDS for PLGA/PEG spinning solutions varying in AgNO3 concentration. Asterisks indicate statistical significance: *p<0.05; p<0.01; *p<0.001.

Energy Dispersive X-Ray Spectroscopy (EDS) was used to perform elemental analysis on blow spun samples of PLGA/PEG containing from 1 to 10 mg/mL of $AgNO_3$ in solution. From three 40 μm×40 μm images (FIG. 25, Panels A-B), we estimated the weight percent (wt %) of silver in blow spun fibers produced from three different PLGA/PEG/Ag solutions containing 1, 5, and 10 mg/mL of $AgNO_3$. The measured wt % varies from 0.67% to 2.4% when sprayed from acetone and from 0.14% to 1.19% when sprayed from ethyl acetate (FIG. 25, Panel C).

Figure 26:
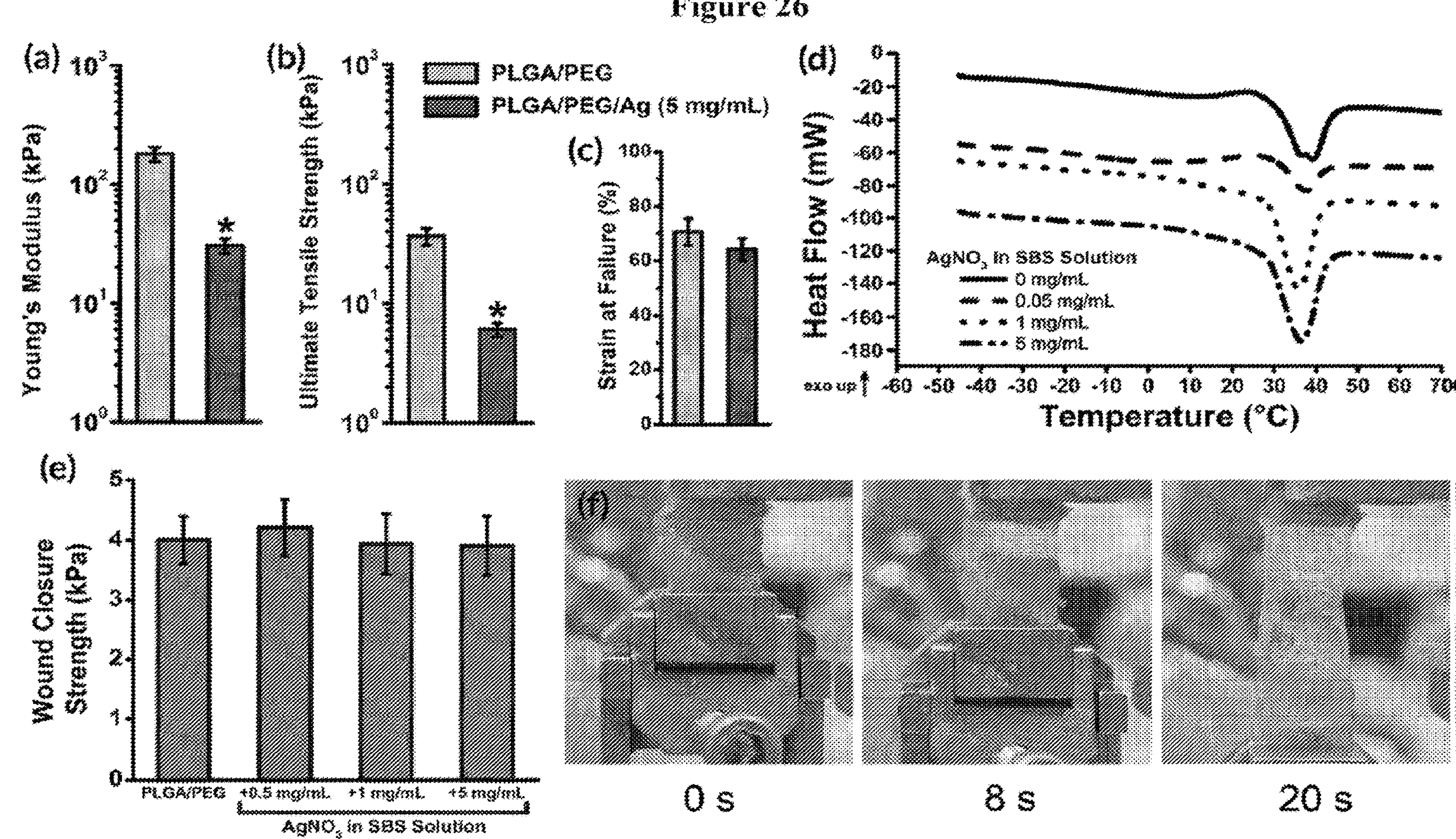
FIG. 26 shows mechanical testing data of PLGA/PEG/Ag wound dressings (n=5). Adding AgNO3 softens the wound dressing, producing lower Young's modulus (Panel A), lower ultimate tensile strength (Panel B), and comparable strain at failure (Panel C). Panel D shows that all polymer blends with AgNO3 exhibit a body temperature mediated melting event at approximately 35° C. using differential scanning calorimetry (DSC). Curves are shifted vertically for clarity. Panel E shows that wound closure strength of PLGA/PEG/Ag dressings is constant as AgNO3 concentration increases (n=5). Panel F shows images of PLGA/PEG/Ag (1 mg/mL) at 0, 8, and 20 s after the start of the wound closure strength test, showing the adhesive at high strain. Asterisks indicate statistical significance: *p<0.05; p<0.01; *p<0.001

Thermal and Mechanical Properties: The effect of $AgNO_3$ on the mechanical and thermal properties of PLGA/PEG was then evaluated. At the highest concentration tested (5 mg/mL), incorporating $AgNO_3$ significantly decreases the tensile strength and stiffness of PLGA/PEG/Ag fiber mats. Young's modulus (FIG. 26, Panel A) and ultimate tensile strength (FIG. 26, Panel B) each decrease by approximately one order of magnitude, while strain at failure is unchanged (FIG. 2C). Despite these decreases, our previous research has indicated that softer and more flexible polymer composites form a better interface with tissue and therefore can have greater adhesion strength and adhesion energy (Behrens A. M. et al. (2015) *Biodegradable-Polymer-Blend-Based Surgical Sealant with Body-Temperature-Mediated Adhesion*, Adv Mater 27:8056-61; Kern N. G. et al. (2017) *Solution blow spun polymer: A novel preclinical surgical sealant for bowel anastomoses*, J Pediatr Surg 52(8):1308-1312). PLGA/PEG undergoes a thermal transition while heating to body temperature triggered by PEG's melting, that allows the fibrous mat to become an intrinsically adhesive conformal film. This transition is consistent regardless of silver content (FIG. 26, Panel D). Wound closure strength was measured according to ASTM F2458-05 on porcine skin (FIG. 26, Panel E), showing PLGA/PEG's combination of adhesion and cohesion (FIG. 26, Panel F). Wound closure strength is unaffected by the addition of $AgNO_3$.

Silver Release Kinetics: The release rate of $Ag^+$ was studied by immersing samples of PLGA/PEG/Ag in 37° C. water for up to one month. Periodically over 28 days, the supernatant was collected and analyzed using inductively coupled plasma-atomic emission spectroscopy (ICP-AES) to determine the concentration of $Ag^+$. This study tested three different $AgNO_3$ concentrations in polymer solution (0.5-5.0 mg/mL). The objective of this study was to determine which formulations released an appropriate amount of $Ag^+$, guided by three benchmarks described in the literature: (1) The 24 hour cytotoxic limit, which is approximately 50 μM for fibroblasts (Srinivasan S. et al., (2011) *Solution*

*spraying of poly(methyl methacrylate) blends to fabricate microtextured, superoleophobic surfaces*, Polymer 52:3209-18; Hidalgo E. et al. (1998) *Silver nitrate: antimicrobial activity related to cytotoxicity in cultured human fibroblasts*, Skin Pharmacol Appl Skin Physiol 11(3):140-51). (FCC) and higher for keratinocytes, 500 μM (KCC) (Damour O. et al. (1992) *Cytotoxicity evaluation of antiseptics and antibiotics on cultured human fibroblasts and keratinocytes*, Burns 18(6):479-85; Teepe R. G. et al. (1993) *Cytotoxic effects of topical antimicrobial and antiseptic agents on human keratinocytes in vitro*, J Trauma 35(1):8-19). (2) The minimum bactericidal concentration (MBC), which is approximately 20 μM for a small model bacterial inoculation (Zhao G. and Stevens S. E., Jr. (1998) *Multiple parameters for the comprehensive evaluation of the susceptibility of Escherichia coli to the silver ion*, Biometals 11(1)27-32). (3) the minimum inhibitory concentration (MIC), which is about 5 μM for an inoculation of the same size.

Figure 27:
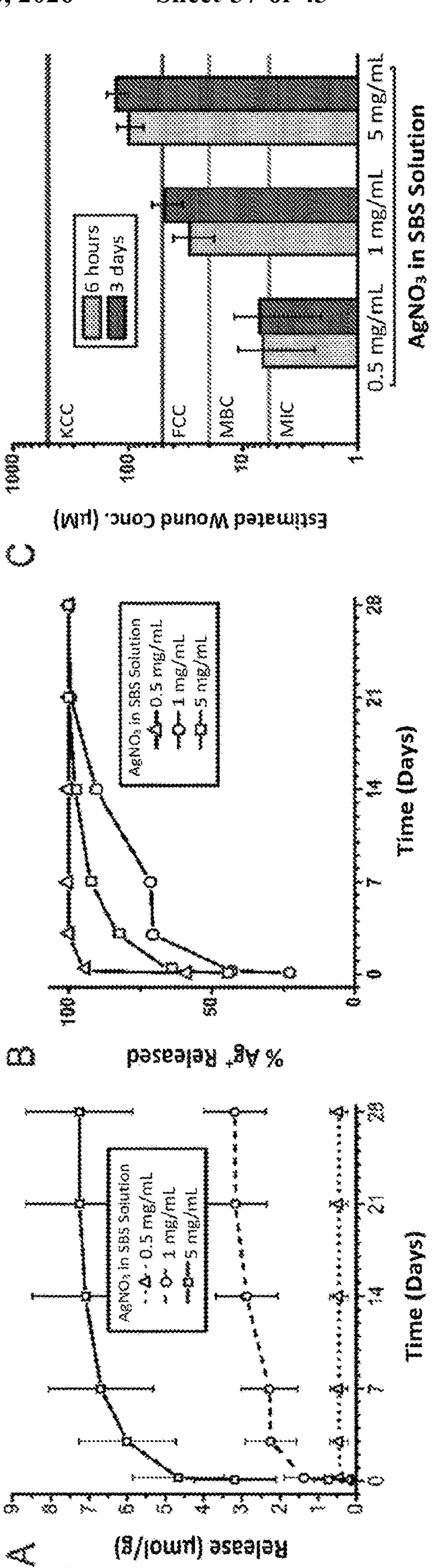
FIG. 27 shows the release of silver ions by solution blow spun (SBS) polymer fiber wound dressings over several days (n=3). Silver ions released in vitro are proportional to the concentration of silver in the SBS polymer solution (Panel A). The fraction of silver ions released over time varies based on how much silver is loaded into the wound dressing (Panel B). Panel C shows estimated concentration in a wound based on the amount of silver released by a wound dressing produced using 2 mL of polymer solution. Data from Panel A were fit to a logarithmic regression model, which was used to estimate concentration in the wound, accounting for projected first-order absorption kinetics of Ag+.

Depending on initial $AgNO_3$ loading concentration, PLGA/PEG/Ag releases between 0.5 μmol and 5 μmol per gram of wound dressing (FIG. 27, Panel A). When loaded with more $AgNO_3$, the release profile changes, with silver release extending over 7 days for 1 mg/mL and 5 mg/mL PLGA/PEG/Ag (FIG. 27, Panel B). $Ag^+$ release is nearly complete within 1 day for PLGA/PEG/Ag 0.5 mg/mL. Higher $AgNO_3$ concentrations had approximately 50% release at 1 day and reached 100% release after approximately 14 days. The differences in release kinetics are related to the size of the burst phase, which occurs during the first hours of drug release and typically accounts for a significant portion of drug release in PLGA devices (Cross S. E. and Roberts M. S. (1999) *Defining a model to predict the distribution of topically applied growth factors and other solutes in excisional full-thickness wounds*, J Invest Dermatol 112(1)36-41; Goetz V. et al. (2013) *A physiologically based pharmacokinetic model for ionic silver and silver nanoparticles*, Int J Nanomedicine 8(1):3365-3382; Barnett A. et al. (1983) *Comparison of Synthetic Adhesive Moisture Vapor Permeable And Fine Mesh Gauze Dressings for Split-Thickness Skin Graft Donor Sites*, Am J Surg 145(3): 379-381).

We estimated the $Ag^+$ concentration in a partial thickness wound sprayed with 2 mL of polymer solution, given a penetration depth of $Ag^+$ into the wound bed of 7.5 mm (FIG. 27, Panel C) (Cross S. E. and Roberts M. S. (1999) *Defining a model to predict the distribution of topically applied growth factors and other solutes in excisional full-thickness wounds*, J Invest Dermatol 112(1):36-41). Each data set was fit to a logarithmic model, which was then used to estimate absorption, distribution, metabolism, and excretion of Ag+ in the wound using previously described first order kinetics (Goetz V. et al. (2013) *A physiologically based pharmacokinetic model for ionic silver and silver nanoparticles*, Int J Nanomedicine 8(1):3365-3382). This model, which combines in vitro Ag+ release data with realistic approximations for wound volume and various clearance rates, is shown in FIG. 27, Panel C. With these design benchmarks, a $AgNO_3$ concentration of 1 mg/mL in the SBS solution was selected that produces a concentration in the wound that is greater than the MBC, but less than or does not greatly exceed the FCC. These SBS dressings could thus remain antimicrobial after application without strong cytotoxicity to the cells in the wound. This model likely overestimates the rate of Ag+ release due to the aqueous in vitro environment, which accelerates Ag+ release compared to the interface of the healing wound.

Figure 28:
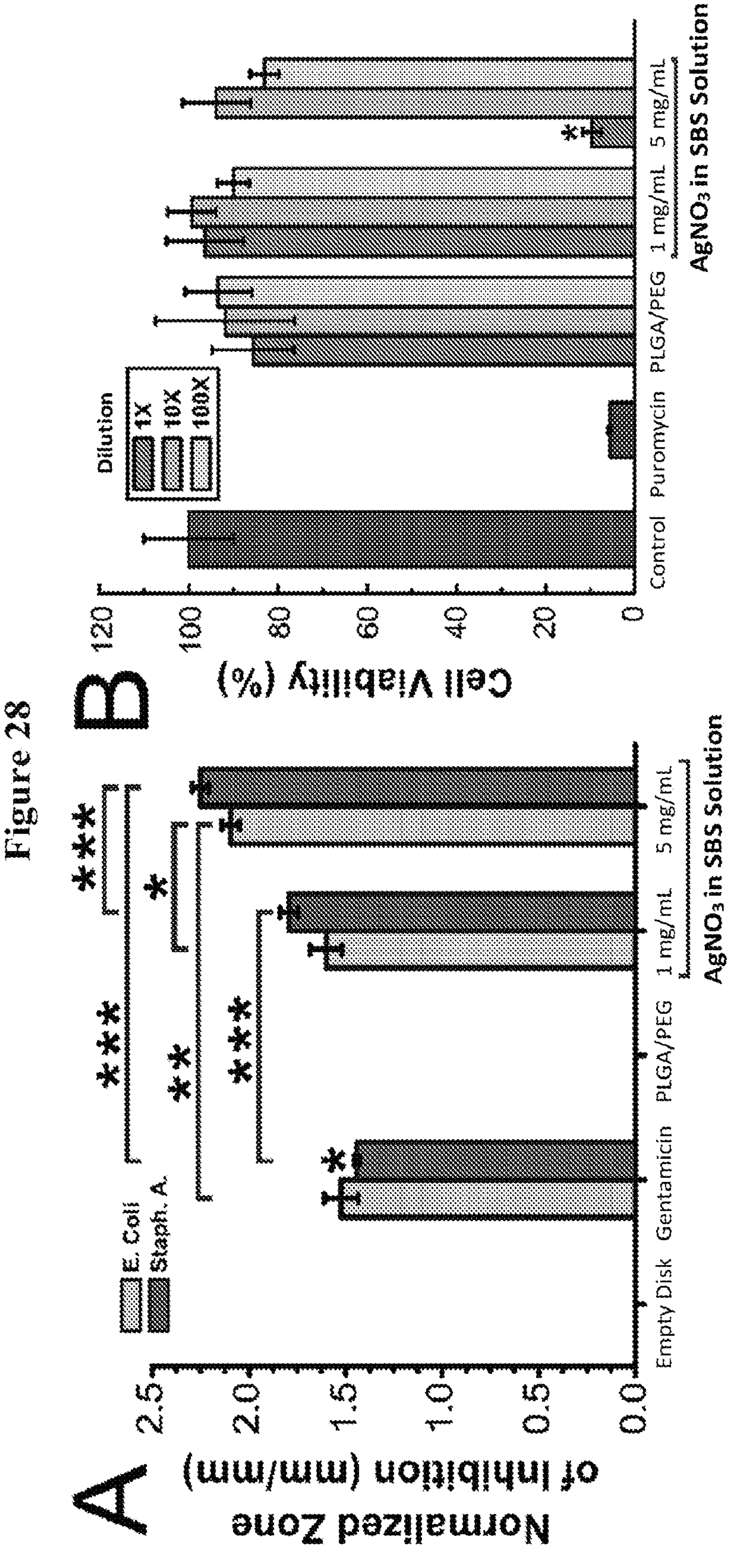
FIG. 28 illustrates the zone of inhibition (ZOI) produced by PLGA/PEG with varying amounts of silver (Panel A). Statistical significance was determined within bacteria type (n=3-5). Panel B shows cytotoxicity of sealants to L929 mouse fibroblasts (n=8). PLGA/PEG/Ag with moderate concentrations of $AgNO_3$ (1 mg/mL) produced a high ZOI with no cytotoxicity. Asterisks indicate statistical significance: *p<0.05; p<0.01; *p<0.001.

Antimicrobial Activity and L929 Cytotoxicity: Silver, while antimicrobial, can be cytotoxic at high concentrations. We aimed to determine a concentration of $AgNO_3$ to incorporate into the polymer mats that suppresses bacterial growth with minimal toxicity. Bacterial growth inhibition was measured by the method of Kirby-Bauer disk diffusion (FIG. 28, Panel A). This inhibition was tested using two commonly infectious Gram-negative and Gram-positive bacteria—*Escherichia coli* and *Staphylococcus aureus*. Concentrations greater than 1 mg/mL $AgNO_3$ produced a normalized zone of inhibition (ZOI) that was not significantly different than the gentamicin control. A greater $AgNO_3$ concentration of 5 mg/mL produced a larger ZOI, while PLGA/PEG alone produced no ZOI. Cytotoxicity towards L929 mouse fibroblasts was tested at the antimicrobial concentrations of $AgNO_3$ (FIG. 28, Panel B). As shown, a $AgNO_3$ concentration of 5 mg/mL led to significant cytotoxicity compared to 95% cell viability at 1 mg/mL. The optimal concentration of $AgNO_3$ of 1 mg/mL produced antimicrobial efficacy yet also allowed for sufficient cell viability.

Figure 29:
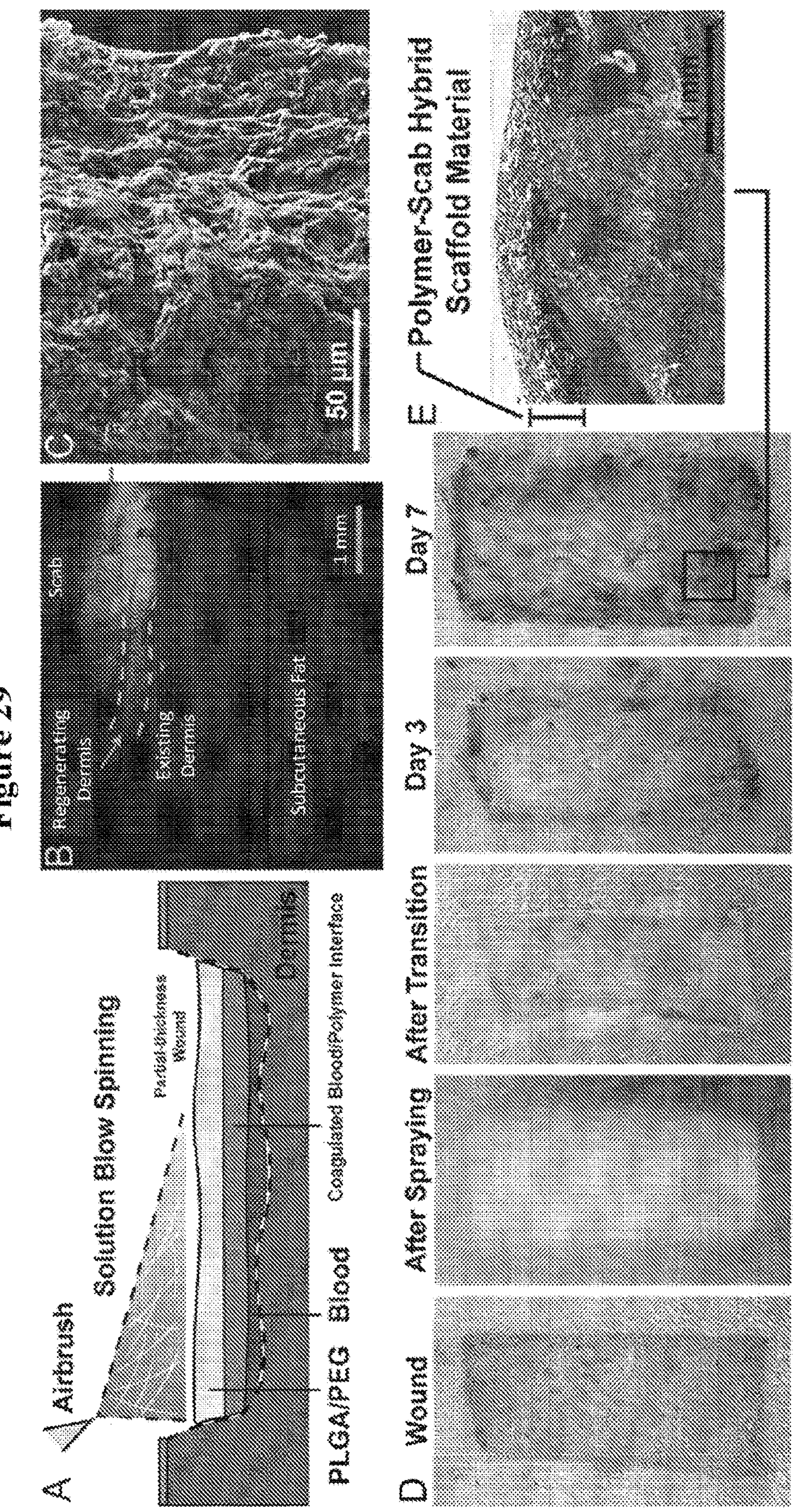
FIG. 29 shows a solution blow spinning process for creating a PLGA/PEG wound dressing in situ. Panel A shows schematically solution blow spun fibers deposited directly into a wound. Fluorescent PLGA is integrated into the scab (Panel B). Panel C shows scab cross section viewed using scanning electron microscopy. Panel D shows the progression of wound dressing before and after adhesive thermal transition, and at 3 and 7 days after use. Panel E is a histological cross section of wound biopsy, stained with Masson's trichrome, showing the polymer-scab hybrid scaffold material at day 7.

Porcine Wound Model: Demonstration of efficacy in wound care requires evaluating the SBS dressings in comparison to commercially available controls. Direct deposition of PLGA/PEG and PLGA/PEG/Ag wound dressings by SBS were investigated in a porcine partial-thickness wound model to characterize wound healing. The clinical control dressing was Tegaderm, an adhesive-coated, semipermeable polyurethane film often used in wound care specifically for skin harvest sites (Barnett A. et al. (1983) *Comparison of Synthetic Adhesive Moisture Vapor Permeable And Fine Mesh Gauze Dressings for Split-Thickness Skin Graft Donor Sites*, Am J Surg 145(3):379-81). Wounds were created with a Dermatome and were immediately dressed with PLGA/PEG, PLGA/PEG/Ag (1 mg/mL $AgNO_3$), or Tegaderm. In this model, PLGA/PEG and PLGA/PEG/Ag dressings were sprayed directly onto the wounds with an airbrush (FIG. 29, Panel A). Spraying 2 mL of polymer solution uniformly across the wound produced complete wound coverage. A polymer-scab composite material is formed as blood coagulates at the interface with the PLGA/PEG dressing, which was demonstrated utilizing fluorescent PLGA (FIG. 29, Panel B). The resulting cross-section of the entire scab at PWD 7 fluoresces, indicating that PLGA is incorporated throughout. Additionally, cross-sectional SEM shows the microfibrous network of fibrin, exudate and PLGA in detail (FIG. 29, Panel C). PLGA/PEG initially adheres to the wound due to the adhesive thermal transition characterized in FIG. 29, Panel D, where the porous SBS nanofiber mat becomes an adhesive thin film (FIG. 29, Panel D). Biodegradable and absorbable PLGA/PEG is then incorporated into the wound, where it forms a durable scaffold and barrier throughout the re-epithelialization process (FIG. 29, Panel E).

Figure 30:
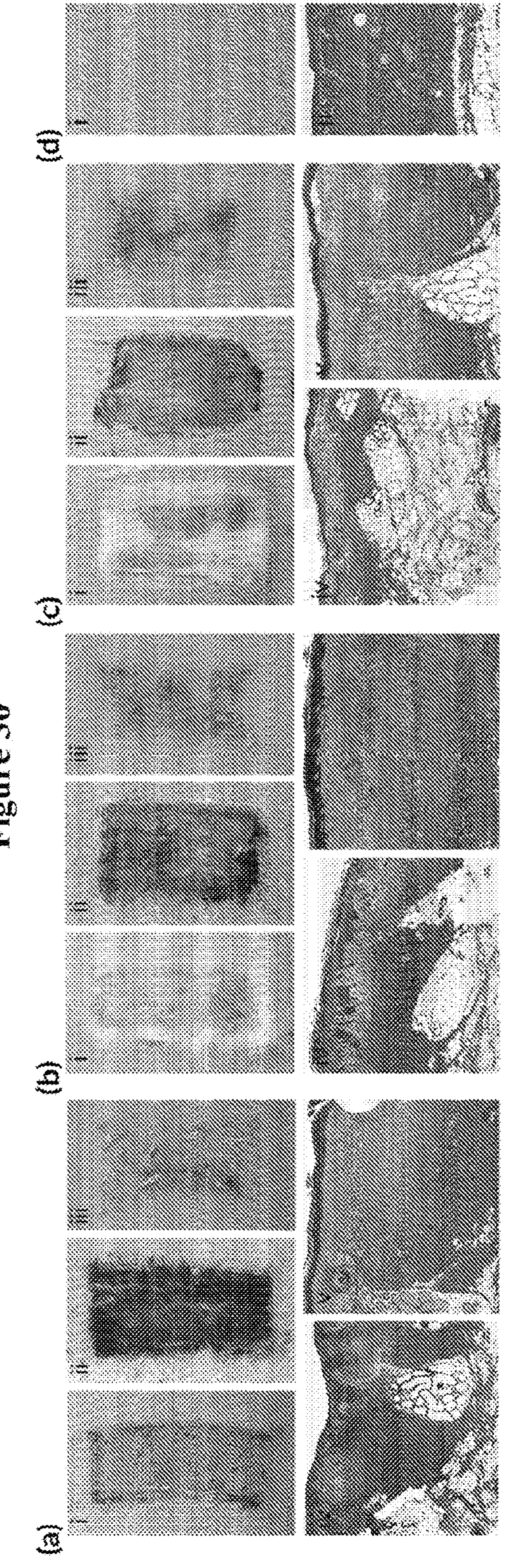
FIG. 30 show partial-thickness wounds dressed with Tegaderm (Panel A), PLGA/PEG (Panel B), PLGA/PEG/Ag (Panel C). Wounds are pictured immediately after creation (Ai, Bi, Ci), after 7 days (Aii, Bii, Cii), and after 35 days (Aiii, Biii, Ciii). Masson's trichrome stained histology of biopsies taken after 7 days (Aiv, Biv, Civ) and 35 days (Av, Bv, Cv). Healthy, unwounded skin is pictured (Panel Di) and shown in histology stained with Masson's trichrome (Dii) for comparison.

Partial-thickness wound healing is shown in FIG. 30. Wounds approximately 600 μm deep were created and immediately dressed with PLGA/PEG, PLGA/PEG/Ag, or Tegaderm (FIG. 30, Panel Ai). PLGA/PEG and PLGA/PEG/Ag are deposited as fibers that, at body temperature, transition to become adhesive and conformal to the wound bed (FIG. 30, Panels Bi and 6Ci). Compared to the polymer dressed wounds, scabs that develop over the Tegaderm-dressed wounds appeared darker (FIG. 30, Panels Aii, Bii, and 7Cii). Shedding of the scab began by the second week of wound healing with a shiny new layer of epidermis visible by PWD 14 on all wounds. At PWD 35, all wounds were healed with complete dermal regeneration and re-epithelialization (FIG. 30, Panels Aiii, 7Biii, and 7Ciii). No infections or other significant complications developed in any of the wounds.

Figure 31:
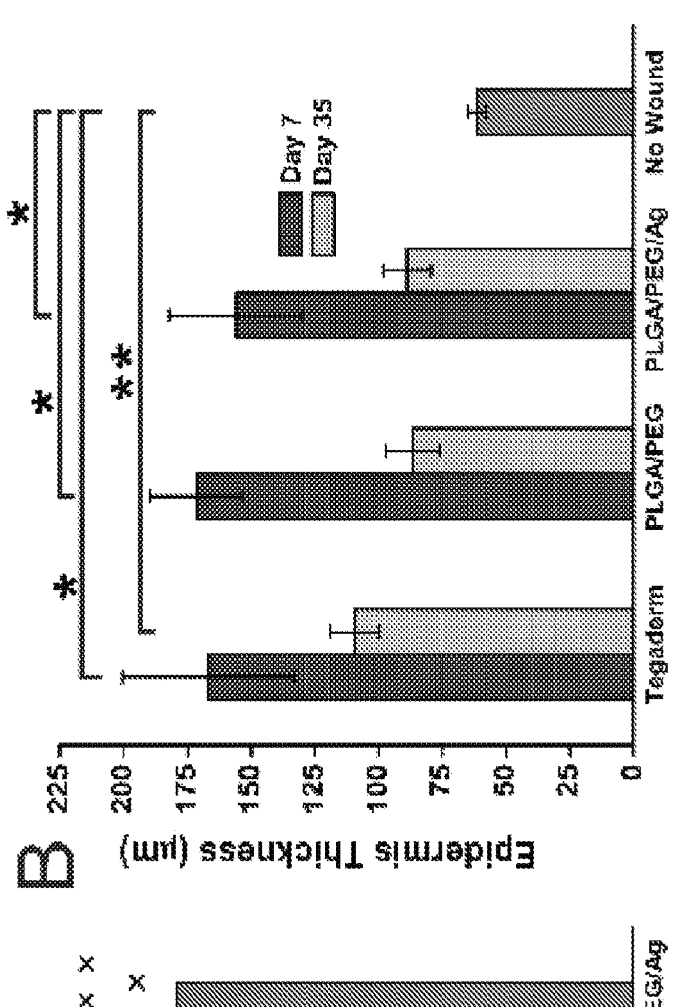
FIG. 31 shows histological characteristics of partial-thickness wound healing for PLGA/PEG, PLGA/PEG/Ag, and Tegaderm wound dressings on PWD 7 and 35 (n=8). Panel A show average surface coverage of the epidermis on the healing wound biopsied at PWD 7. Individual data points are overlaid. Panel B shows epidermis thickness of the healing wounds. Panel C shows ratio of neodermis thickness to total dermis thickness. Panel D shows blood vessel density in the dermis of the healing wound. Asterisks indicate statistical significance: *p<0.05; p<0.01; *=p<0.001.
Figure 31:
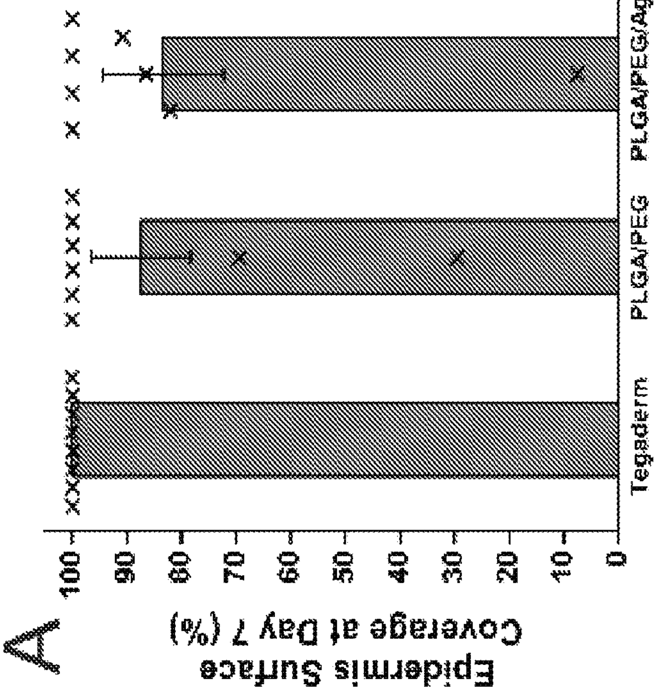
Figure 31:
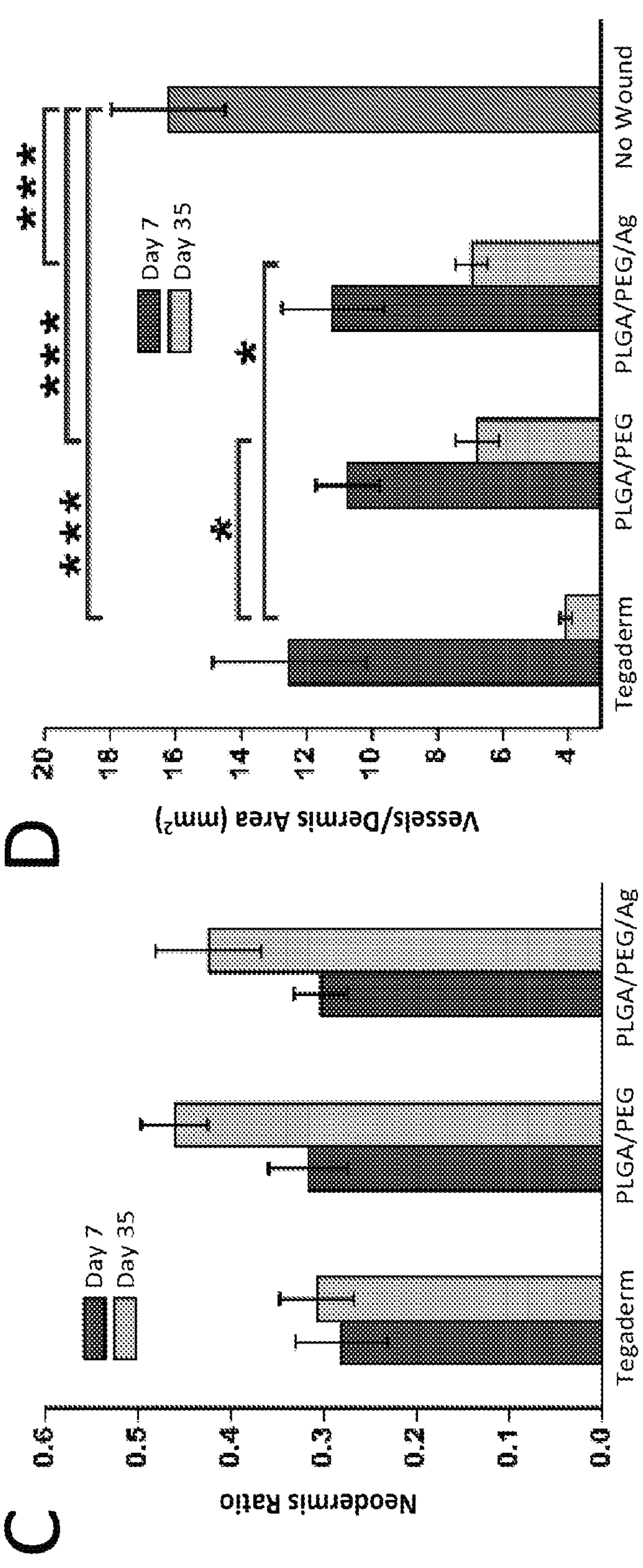

Dermal and Epidermal Tissue Regeneration: Wound healing was assessed by histology, which showed only slight differences in healing rates between the dressing groups. On PWD 7, Tegaderm-dressed wounds had complete epidermis coverage across the surface of the biopsy on histology (FIG. 31, Panel A). Two PLGA/PEG and four PLGA/PEG/Ag dressed wounds showed incomplete epidermal regrowth. However, total epidermal thicknesses were similar across the dressing groups on PWD 7 (FIG. 31, Panel B). At PWD 35, epidermis thickness was similar between PLGA/PEG-dressed wounds and healthy, unwounded skin, while Tegaderm was significantly thicker (FIG. 31, Panel B).

After injury, the regenerating dermis (neodermis) consists of loose collagen fibers that are remodeled into dense, mature bundles as the wound heals. Stained with Masson's trichrome, these collagen structures appear light grey, while uninjured organized collagen fibrils appear dark grey. The thickness of the neodermis was compared to the total thickness of the dermis, to determine how much neodermis was deposited relative to total dermis thickness (FIG. 31, Panel C). On PWD 7, the neodermis ratio was similar among all wounds. On PWD 35, wounds dressed with Tegaderm had the lowest neodermis ratio. Angiogenesis is an important factor in the early stages of wound healing that can be measured by the dermis blood vessel density (Richardson T. P. et al. (2001) *Polymeric system for dual growth factor delivery*, Nat Biotechnol. 19(11):1029-1034). Blood vessel density in the dermis and neodermis was also measured, normalizing for dermis cross-sectional area (Sun G. et al. (2011) *Dextran hydrogel scaffolds enhance angiogenic responses and promote complete skin regeneration during burn wound healing*, Proc Natl Acad Sci USA 108:20976-81). Despite initially being similar at PWD 7, blood vessel density is significantly increased at PWD 35 for PLGA/PEG and PLGA/PEG/Ag compared to Tegaderm (FIG. 31, Panel D). All wounds have decreased blood vessel density compared to unwounded skin at PWD 35.

Figure 32:
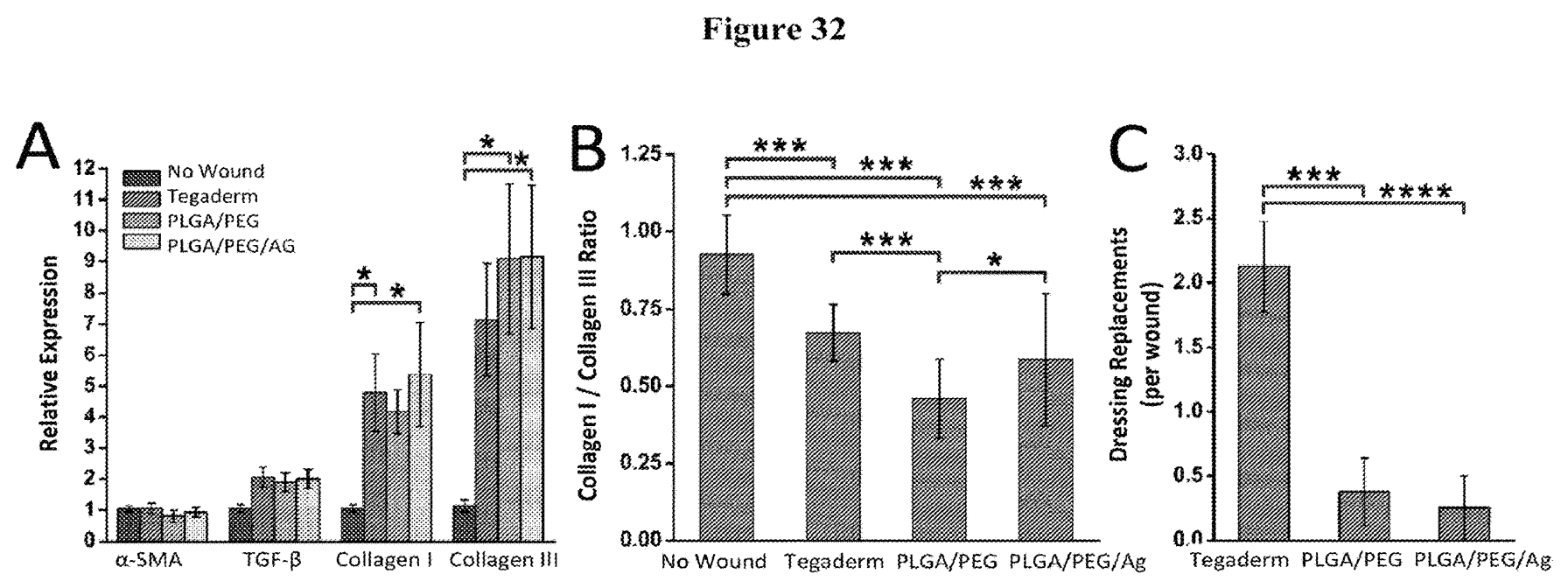

The gene expression of critical factors in wound healing and scarring was measured in the wound tissue at PWD 35. Expression levels of α-smooth muscle actin (α-SMA), vascular endothelial growth factor (VEGF), transforming growth factor β1 (TGF-β1), collagen type I, and collagen type III were measured using real-time PCR. Measurements were normalized to normal, unwounded skin taken from the upper and lower back. Overall, there were no statistically significant differences between the wounds dressed with Tegaderm, PLGA/PEG, and PLGA/PEG/Ag (FIG. 32, Panel A). Collagen I to collagen III ratio, which is indicative of how much disorganized, scar-forming collagen is deposited, is also similar between dressings (FIG. 32, Panel B).

Wound dressings must be replaced if exudate buildup causes the potential for maceration, or if the dressing comes off the wound. Over the first 14 days of wound healing, dressings were assessed for maintaining adherence to the wound bed. Wounds were checked daily, and dressings were replaced as needed. At PWD 14, all dressings were removed, and all wounds showed a visible layer of epidermis. Tegaderm dressings required a replacement at a significantly higher frequency than PLGA/PEG or PLGA/PEG/Ag (FIG. 32, Panel C). Tegaderm dressings rely on a pressure sensitive adhesive coating to maintain adherence, but normal movement and fluid accumulation resulted in separation and loss of dressing. As the wound heals, the SBS dressings become less flexible but adhere strongly as they are integrated into the scab, which contains exudate and blood. Ultimately, some PLGA/PEG is degraded, while other parts may be displaced by the eschar as the wound epithelializes and come off with the scab.

DISCUSSION

An ideal dressing is easy and painless to apply, antimicrobial, keeps a moist wound environment, and requires minimal dressing changes while still protecting the wound. Here, we demonstrate that SBS allows for in situ sprayable wound dressing deposition with minimal wound contact. This ensures consistency with "no-touch" technique, which is used in clinical practice to minimize transfer of infectious microorganisms and protect the wound (Wound O, Continence Nurses Society Wound C, Association for Professionals in Infection C, Epidemiology IGC. Clean vs. sterile dressing techniques for management of chronic wounds: a fact sheet. J Wound Ostomy Continence Nurs 39(2 Suppl): S30-4). A portable airbrush can deliver the initially fibrous sealant (FIG. 24) directly onto the wound bed. A biodegradable PLGA/PEG blend provides inherent adhesion and occlusion, and integrates into the wound, reducing the rate of dressing replacement. Adding $AgNO_3$ to the PLGA/PEG fibers gives the wound dressing antimicrobial properties (FIG. 28, Panel A) that do not compromise its mechanical properties (FIG. 26, Panels A-C), thermal characteristics (FIG. 26, Panel D), tissue adhesion strength (FIG. 26, Panel E) or biocompatibility (FIG. 28, Panel B).

The benefits of a moist wound environment provided by an occlusive dressing are established, with faster re-epithelialization and less scarring (Reish R. G. et al. (2009) *Modulation of scarring in a liquid environment in the Yorkshire pig*, Wound Repair Regen 17:806-16; Eming S. A. (2012) In: Jean L. Bolognia JVS, Lorenzo Cerroni, ed. Dermatology. 3rd ed: Elsevier; 2313-1325; Berman B. et al. (2017) *Keloids and Hypertrophic Scars: Pathophysiology, Classification, and Treatment*, Dermatol Surg 43 Suppl 1:S3-S18). Dry, solid polymer wound dressings such as Tegaderm provide a semipermeable barrier to pathogens and liquid flow, allowing air and water vapor in the wound to be exchanged. Tegaderm was thus chosen as the clinical control. Alternatives such as autologous keratinocyte grafts and bi-layered skin substitutes, which incorporate living cells to improve wound healing, may also be used in combination (Zaulyanov L. and Kirsner R. S. (2007) *A review of a bi-layered living cell treatment* (*Apligraf*®) *in the treatment of venous leg ulcers and diabetic foot ulcers*, Clinical interventions in aging 2:93; Auxenfans C. et al. (2015) *Cultured autologous keratinocytes in the treatment of large and deep burns: A retrospective study over* 15 *years*, Burns 41:71-9). However, synthetic options that incorporate both an effective scaffold for wound healing and a solid barrier to pathogens and liquid transport are limited. Hydrogel and silicone-based multi-layered dressings have been developed to provide both adequate hydration and an internal layer of synthetic matrix, often composed of polyurethane or nylon (Cassidy C. et al. (2005) *Biobrane versus duoderm for the treatment of intermediate thickness burns in children: A prospective, randomized trial*, Burns 31:890-3; Cheshire P. A. et al. (2016) *Artificial dermal templates: A comparative study of NovoSorb™ Biodegradable Temporising Matrix* (*BTM*) *and Integra® Dermal Regeneration Template* (*DRT*), Burns 42:1088-96). These devices are typically only used selectively due to difficulty of use or high cost (Greenwood J. E. et al. (2009) *Experience With Biobrane: Uses and Caveats for Success*, Eplasty 9:e25; Feldman D. L. et al.

(1991) *A prospective trial comparing Biobrane, Duoderm and xeroform for skin graft donor sites*, Surgery, Gynecology & Obstetrics 173:1-5).

PLGA/PEG and PLGA/PEG/Ag dressings adhere to the wound and absorb exudate, forming a durable polymer-scab hybrid scaffold that protects the wound and falls off after re-epithelialization and keratinization of the wound bed. PLGA/PEG and PLGA/PEG/Ag dressings can be easily applied (FIG. 29, Panel A) and require no dressing changes until the wound is healed. When fabricated with fluorescent PLGA, PLGA molecules are present in the regenerated dermis (FIG. 29, Panel B), indicating its absorbability and the close interface formed and allows for re-epithelialization and collagen regeneration (FIG. 29, Panel E). Unlike the thin film polyurethane dressings, the SBS dressings showed high adhesiveness to the raw wound bed and required fewer replacements (FIG. 32, Panel C). This study further supports existing evidence that biodegradable polyesters, although relatively uncommon in wound dressings, can produce excellent results as scalable, low cost alternatives for large TBSA wounds (Uhlig C. et al. (2007) *Suprathel®—An innovative, resorbable skin substitute for the treatment of burn victims*, Burns 33:221-9; Schwarze H. et al. (2007) *Suprathel, a new skin substitute, in the management of donor sites of split-thickness skin grafts: results of a clinical study*, Burns 33:850-4).

Wound healing is a complex and tightly regulated inflammatory process, during which excessive inflammation leads to greater scaring (Eming S. A. (2012) In: Jean L. Bolognia J V S, Lorenzo Cerroni, ed. Dermatology. 3rd ed: Elsevier; 2012:2313-1325; Berman B. et al. (2017) *Keloids and Hypertrophic Scars: Pathophysiology, Classification, and Treatment*, Dermatol Surg 43 Suppl 1:S3-S18; Caetano G. F. et al. (2016) *Comparison of collagen content in skin wounds evaluated by biochemical assay and by computer-aided histomorphometric analysis*, Pharm Biol 54:2555-9; Cannesso M. C. et al. (2014) *Skin wound healing is accelerated and scarless in the absence of commensal microbiota*, J Immunol 193:5171-80). Skin injury produces a cascade of events that includes infiltration of neutrophils, fibroblasts and endothelial cells (Sun G. et al. (2011) *Dextran hydrogel scaffolds enhance angiogenic responses and promote complete skin regeneration during burn wound healing*, Proc Natl Acad Sci USA 108:20976-81; Eming S. A. (2012) In: Jean L. Bolognia J V S, Lorenzo Cerroni, ed. Dermatology. 3rd ed: Elsevier; 2012:2313-1325; Sorrell J. M. and Caplan A. I. (2004) *Fibroblast heterogeneity: more than skin deep*, J Cell Sci 117:667-75). In a milieu of inflammatory cytokines and growth factors, new components of the dermis and epidermis are laid down throughout the stages of wound healing. All wounds healed at similar rates and with similar cosmetic results in terms of scarring (FIG. 30, Panels A-C). While the Tegaderm dressing was found to have more complete epidermal surface coverage on wound biopsies on PWD 7 (FIG. 31, Panel A), the slower rate of re-epithelialization with the PLGA/PEG/Ag dressings is not surprising given the known inhibitory effects of silver on keratinocyte, fibroblasts, and epidermal cells (Galandakova A. et al. (2016) *Effects of silver nanoparticles on human dermal fibroblasts and epidermal keratinocytes*, Hum Exp Toxicol 35:946-57; Toussaint J. et al. (2015) *Topical antibiotic ointment versus silver-containing foam dressing for second-degree burns in swine*, Acad Emerg Med 22(8):927-33) and did not have a negative effect on outcomes.

The PLGA/PEG dressed wounds showed similar dermal and epidermal thicknesses at PWD 7 (FIG. 31, Panel B) to wounds covered with thin-film polyurethane-based Tegaderm, indicating that dermal tissue regeneration was not affected by PLGA/PEG. Further, at PWD 35, epidermal thickness for PLGA/PEG and PLGA/PEG/Ag was 47 and 43% closer, respectively, to healthy skin than that of Tegaderm. Significant epidermal hypertrophy indicates greater levels of inflammation during the early stages of wound healing (O'Shaughnessy K. D. et al. (2009) *Homeostasis of the epidermal barrier layer: a theory of how occlusion reduces hypertrophic scarring*, Wound Repair Regen. 17(5): 700-708). Although similar at PWD 7, at PWD 35, blood vessel density is significantly increased for PLGA/PEG and PLGA/PEG/Ag compared to Tegaderm (FIG. 31, Panel D). This indicates greater levels of angiogenesis in the healing dermis during the proliferative stage of wound repair which is critical for healing (Gurtner G. C. et al. (2008) *Wound repair and regeneration*, Nature 453:314-321; Li J. et al. (2003) *Angiogenesis in wound repair: angiogenic growth factors and the extracellular matrix*, Microsc Res Tech. 60(1):107-114). Revascularization could be stimulated by the lactic acid supplied by the biodegradable PLGA scaffold, which has been shown to increase angiogenesis (Porporato P. E. et al. (2012) *Lactate stimulates angiogenesis and accelerates the healing of superficial and ischemic wounds in mice*, Angiogenesis 15(4):581-592; Chereddy K. K. et al. (2018) *PLGA: from a classic drug carrier to a novel therapeutic activity contributor*, J Control Release 289:10-13; Sun S. et al. (2017) *Lactic acid: no longer an inert and end product of glycolysis*, Phys Ther 32(6):453-463).

High expression of TGF-β leads to excess fibroblast activity, which contributes to the development of hypertrophic scars and keloids (Eming S. A. (2012) In: Jean L. Bolognia J V S, Lorenzo Cerroni, ed. Dermatology. 3rd ed: Elsevier; 2313-1325; Berman B. et al. (2017) Keloids and Hypertrophic Scars: Pathophysiology, Classification, and Treatment, Dermatol Surg 43 Suppl 1:S3-S18). The composition of collagen subtypes can also give insight into the degree of scarring that may ultimately develop in the wounds. Scarless healing has been linked to greater collagen III deposition, while hypertrophic and keloidal scars have increased collagen production and an increased ratio of collagen I to collagen III (Berman B. et al. (2017) *Keloids and Hypertrophic Scars: Pathophysiology, Classification, and Treatment*, Dermatol Surg 43 Suppl 1:S3-S18; Canesso M. C. et al. (2014) *Skin wound healing is accelerated and scarless in the absence of commensal microbiota*, J Immunol 193:5171-80). At PWD 35, there were no significant differences in the expression of these factors in the wounds treated with the three dressing groups (FIG. 32, Panel A), indicating that all wounds are past the inflammatory phase of wound healing. All wounds had greater expression of collagen III than collagen I (FIG. 32, Panel B), likely indicating similar amounts of scarring.

Pigs, which provide the best animal model for human skin, expose the wounds to unpredictable trauma and shear forces. Tegaderm dressed wounds suffered significantly greater dressing loss than those dressed with PLGA/PEG or PLGA/PEG/Ag (FIG. 32, Panel C). The most likely reason is the moist environment, which reduces the adhesiveness of the dressing. Ultimately, PLGA/PEG and PLGA/PEG/Ag have better adhesion to wounds because they form a durable protective interface with tissue that is reinforced with fibrin from coagulated blood and can absorb exudate. However, shear forces from animal movement and cage trauma led to some dressing retraction from the wound edges. This likely created a drier and less protected environment at the wound edge, delaying the rate of re-epithelialization seen at the biopsy sites.

Clinically, most partial thickness wounds with would be dressed with antimicrobial ointments dressing or ointment, like bacitracin or silver sulfadiazine, and gauze. These dressings are not occlusive and require daily dressing changes. They are often time-consuming and difficult to apply, and painful for the patient. By controllably releasing silver nitrate from solution blow spun PLGA/PEG/Ag, the requirements for a rapid, broad-spectrum antibiotic treatment and a highly adhesive wound dressing that absorbs exudate are met. Release of Ag+ can be tailored for lasting antimicrobial activity without incurring high cytotoxicity. The sprayable SBS process allows for simple application of a conformal dressing for wounds of any shape and size that does not need to be removed or changed. Overall, the use of PLGA/PEG-based dressings is simple, effective, and without significant wound complication or delay in healing, as demonstrated by the data herein.

All identified publications and references mentioned in this specification are herein incorporated by reference to the same extent as if each individual publication was specifically and individually indicated to be incorporated by reference in its entirety. While the disclosure has been described in connection with exemplary embodiments thereof, it will be understood that it is capable of further modifications and this application is intended to cover any variations, uses, or adaptations of the disclosure following, in general, the principles of the disclosure and including such departures from the present disclosure as come within known or customary practice within the art to which the disclosure pertains and as may be applied to the features hereinbefore set forth.

What is claimed is:

1. A composition comprising:

a solution comprising:

(i) between about 1% and about 20% weight per volume (w/v) low molecular weight (LMW) polymer; and (ii) between about 1% and about 20% (w/v) high molecular weight (HMW) polymer;

wherein said LMW polymer is PEG;

wherein said poly(ethylene glycol) (PEG) has a molecular weight of 950 to 1050 Da; and wherein said HMW polymer has a molecular weight of about 10000 Da to about 42000 Da.

2. The composition of claim 1, wherein said HMW polymer is poly(lactide-co-caprolactone) (PLCL) or poly (lactide-co-glycolide) (PLGA).

3. The composition of claim 1, which, after sprayed and dried, yields a solid adhesive comprising a ratio of the LMW polymer to the HMW polymer ranging from 90:10 to 20:80 by weight.

4. The composition of claim 3, wherein the weight ratio of the LMW polymer to the HMW polymer of the solid adhesive is about 50:50 by weight.

5. The composition of claim 3, wherein the weight ratio of the LMW polymer to the HMW polymer of the solid adhesive is about 70:30 by weight.

6. The composition of claim 1, wherein said solution further comprises between about 0.01% and about 1% w/v therapeutic agent based on the volume of the solution, wherein said therapeutic agent is selected from the group consisting of a protein, a peptide, an amine, an aliphatic compound, and an antibiotic.

7. The composition of claim 1, wherein the solution comprises one or more volatile solvent(s).

8. The composition of claim 1, wherein said HMW polymer is poly(lactide-co-caprolactone) (PLCL).

9. The composition of claim 8, wherein said PLCL is present in a molecular weight of about 35000 Da.

10. A biocompatible polymer fiber construct comprising blow spun polymer fibers formed from said composition of claim 1.

11. The construct of claim 10, which is a tissue sealant, adhesive, hemostatic or scaffolding material.

12. The construct of claim 10, wherein said polymer fibers have an average diameter of between about 1 micrometer (μm) and about 12 μm.

13. A method of forming a polymer fiber construct, comprising:

forming a plurality of polymer fibers using a solution blow spinning process, wherein said polymer fibers are formed from said composition of claim 1; and depositing said plurality of blow spun polymer fibers onto a target to form a conformal polymer fiber construct thereon.

14. The method of claim 13, wherein said target is a tissue surface, said polymer fiber construct formed on said tissue surface in vivo.

* * * * *